United States Patent
Lohmeier et al.

(10) Patent No.: US 10,258,421 B2
(45) Date of Patent: Apr. 16, 2019

(54) SURGICAL INSTRUMENT, ARRANGEMENT AND DRIVE TRAIN ARRANGEMENT FOR A SURGICAL INSTRUMENT, IN PARTICULAR A ROBOT-GUIDED SURGICAL INSTRUMENT, AND SURGICAL INSTRUMENT

(71) Applicant: KUKA Deutschland GmbH, Augsburg (DE)

(72) Inventors: Sebastian Lohmeier, Munich (DE); Wolfgang Schober, Pottmes (DE); Sven Brudniok, Langerringen (DE)

(73) Assignee: KUKA Deutschland GmbH, Augsburg (DE)

( * ) Notice: Subject to any disclaimer, the term of this patent is extended or adjusted under 35 U.S.C. 154(b) by 0 days.

(21) Appl. No.: 14/579,172

(22) Filed: Dec. 22, 2014

(65) Prior Publication Data
US 2015/0173726 A1    Jun. 25, 2015

Related U.S. Application Data

(63) Continuation of application No. PCT/EP2013/001917, filed on Jun. 28, 2013.

(30) Foreign Application Priority Data

Jul. 3, 2012 (DE) .................. 10 2012 013 242
Mar. 11, 2013 (DE) .................. 10 2013 004 230
(Continued)

(51) Int. Cl.
*A61B 17/00* (2006.01)
*A61B 34/00* (2016.01)
(Continued)

(52) U.S. Cl.
CPC .............. *A61B 46/10* (2016.02); *A61B 17/00* (2013.01); *A61B 34/30* (2016.02); *A61B 34/76* (2016.02);
(Continued)

(58) Field of Classification Search
CPC .............................................. A61B 2019/2292
(Continued)

(56) References Cited

U.S. PATENT DOCUMENTS 222,772 A     12/1879  Clark
1,939,905 A *  12/1933  Lee ................................ 477/181
(Continued)

FOREIGN PATENT DOCUMENTS

CN       1216454 A       5/1999
CN     101027010 A       8/2007
(Continued)

OTHER PUBLICATIONS

European Patent Office; Search Report in International Patent Application No. PCT/EP2013/001917 dated Dec. 3, 2013; 6 pages.
(Continued)

*Primary Examiner* — Lynsey C Eiseman
*Assistant Examiner* — Amanda L Steinberg
(74) *Attorney, Agent, or Firm* — Dorton & Willis, LLP

(57) ABSTRACT

A surgical instrument arrangement has a modular motor drive unit which has a drive arrangement having at least one output element, an instrument shaft that can be detachably connected to the drive unit, and a drive arrangement having at least one input drive element. The output drive arrangement and the input drive arrangement can be coupled to each other by a mechanical interface that has at least one single-sided linkage, a pin, and a cut-out, wherein the pin can be radially expanded in the cut-out. Alternatively, a gap may be formed between the pin and the cut-out, which gap is wavy (Continued)

in the radial direction, and in which a radially displaceable, axially fixed intermediate element arrangement is arranged. The surgical instrument arrangement may also include a sterile barrier, which is provided to envelop the drive unit and to be arranged between the drive unit and the instrument shaft.

17 Claims, 33 Drawing Sheets

(30) Foreign Application Priority Data

| Mar. 14, 2013 | (DE) | ........................ 10 2013 004 487 |
| Mar. 28, 2013 | (DE) | ........................ 10 2013 005 493 |
| May 6, 2013 | (DE) | ........................ 10 2013 007 761 |

(51) Int. Cl.
  *A61B 34/30* (2016.01)
  *A61B 46/10* (2016.01)
  *A61B 90/00* (2016.01)

(52) U.S. Cl.
  CPC ................ *A61B 2017/0046* (2013.01); *A61B 2017/00398* (2013.01); *A61B 2090/064* (2016.02); *F04C 2270/0421* (2013.01)

(58) Field of Classification Search
  USPC ................................................ 606/1; 74/490
  See application file for complete search history.

(56) References Cited

U.S. PATENT DOCUMENTS

| 2,227,727 | A | | 1/1941 | Leggiadro | |
| 4,055,185 | A | * | 10/1977 | Waldron | A61B 17/1633 |
| | | | | | 279/77 |
| 4,619,155 | A | * | 10/1986 | Futaba | B62D 3/123 |
| | | | | | 180/428 |
| 4,710,093 | A | * | 12/1987 | Zimmer | B25J 15/0491 |
| | | | | | 294/86.4 |
| 4,919,112 | A | | 4/1990 | Siegmund | |
| 5,047,952 | A | | 9/1991 | Kramer et al. | |
| 5,174,772 | A | * | 12/1992 | Vranish | B25J 15/04 |
| | | | | | 439/131 |
| 5,395,312 | A | | 3/1995 | Desai | |
| 5,741,113 | A | * | 4/1998 | Bacchi | B25J 9/042 |
| | | | | | 414/744.5 |
| 5,855,583 | A | | 1/1999 | Wang et al. | |
| 6,331,181 | B1 | | 12/2001 | Tierney et al. | |
| 6,443,973 | B1 | | 9/2002 | Whitman | |
| 6,594,552 | B1 | | 7/2003 | Nowlin et al. | |
| 6,601,468 | B2 | * | 8/2003 | Grover | B25J 9/042 |
| | | | | | 414/744.5 |
| 6,656,196 | B1 | | 12/2003 | Carriazo | |
| 6,723,106 | B1 | | 4/2004 | Charles et al. | |
| 7,608,083 | B2 | * | 10/2009 | Lee | A61B 17/0469 |
| | | | | | 606/1 |
| 7,955,321 | B2 | * | 6/2011 | Kishi | A61B 19/22 |
| | | | | | 600/410 |
| 8,551,116 | B2 | * | 10/2013 | Julian | A61B 17/00234 |
| | | | | | 606/130 |
| 2003/0216723 | A1 | | 11/2003 | Shinmura et al. | |
| 2004/0054353 | A1 | * | 3/2004 | Taylor | A61B 17/3423 |
| | | | | | 606/1 |
| 2006/0030840 | A1 | * | 2/2006 | Nowlin | A61B 19/22 |
| | | | | | 606/1 |
| 2006/0052664 | A1 | | 3/2006 | Julian et al. | |
| 2006/0161137 | A1 | * | 7/2006 | Orban, III | A61B 19/081 |
| | | | | | 606/1 |
| 2006/0161138 | A1 | * | 7/2006 | Orban, III | A61B 19/081 |
| | | | | | 606/1 |
| 2006/0206100 | A1 | * | 9/2006 | Eskridge | A61B 17/14 |
| | | | | | 606/1 |
| 2006/0235436 | A1 | * | 10/2006 | Anderson | A61B 19/081 |
| | | | | | 606/130 |
| 2007/0299427 | A1 | | 12/2007 | Yeung et al. | |
| 2008/0065100 | A1 | | 3/2008 | Larkin | |
| 2008/0065110 | A1 | | 3/2008 | Duval et al. | |
| 2008/0103492 | A1 | * | 5/2008 | Morley | A61B 17/062 |
| | | | | | 606/1 |
| 2008/0140088 | A1 | | 6/2008 | Orban, III | |
| 2009/0248039 | A1 | | 10/2009 | Cooper et al. | |
| 2010/0082041 | A1 | | 4/2010 | Prisco | |
| 2010/0170519 | A1 | | 7/2010 | Romo et al. | |
| 2010/0268349 | A1 | | 10/2010 | Stuart | |
| 2011/0004225 | A1 | | 1/2011 | Choi et al. | |
| 2011/0087238 | A1 | | 4/2011 | Wang et al. | |
| 2011/0106019 | A1 | | 5/2011 | Bagwell et al. | |
| 2011/0277775 | A1 | * | 11/2011 | Holop | A61B 17/3423 |
| | | | | | 128/849 |
| 2012/0065655 | A1 | | 3/2012 | Ross et al. | |
| 2013/0018304 | A1 | | 1/2013 | Bagwell et al. | |
| 2013/0205558 | A1 | | 8/2013 | Sporer et al. | |
| 2015/0173727 | A1 | * | 6/2015 | Lohmeier | A61B 19/081 |
| | | | | | 606/1 |
| 2015/0173728 | A1 | * | 6/2015 | Lohmeier | A61B 19/081 |
| | | | | | 606/1 |

FOREIGN PATENT DOCUMENTS

| CN | 101340848 A | 1/2009 |
| CN | 102171006 A | 8/2011 |
| CN | 102256550 A | 11/2011 |
| CN | 102630154 A | 8/2012 |
| DE | 3712929 A1 | 11/1988 |
| DE | 19954497 C1 | 4/2001 |
| DE | 10030114 A1 | 12/2001 |
| DE | 102006059165 A1 | 8/2007 |
| DE | 102009060987 A1 | 6/2011 |
| DE | 102010027248 A1 | 1/2012 |
| DE | 102012008535 A1 | 10/2013 |
| EP | 1015068 B1 | 7/2000 |
| JP | 2008519665 A | 6/2008 |
| KR | 19990087101 A | 12/1999 |
| KR | 100778387 B1 | 11/2007 |
| KR | 20090101532 A | 9/2009 |
| KR | 20110069114 A | 6/2011 |
| WO | 2001013802 A1 | 3/2001 |
| WO | 2009079301 A1 | 6/2009 |
| WO | 2010039387 A1 | 4/2010 |
| WO | 2010121117 A1 | 10/2010 |
| WO | 2010123231 A2 | 10/2010 |
| WO | 2011019878 A1 | 2/2011 |
| WO | 2011037394 A2 | 3/2011 |
| WO | 2011/069863 A1 | 6/2011 |
| WO | 2011143022 A1 | 11/2011 |

OTHER PUBLICATIONS

European Patent Office; Search Report and Written Opinion in International Patent Application No. PCT/EP2013/001917 dated Mar. 19, 2014; 24 pages.
European Patent Office; Published Search Report in International Patent Application No. PCT/EP2013/001917 (WO 2014/005689 A3) dated Jan. 9, 2014; 16 pages.
German Patent Office; Search Report in German Patent Application No. 10 2013 004 487.1 dated Nov. 5, 2013; 6 pages.
German Patent Office; Search Report in German Patent Application No. 10 2013 005 493.1 dated Nov. 26, 2013; 8 pages.
German Patent Office; Search Report in German Patent Application No. 10 2013 007 761.3 dated Jan. 2, 2014; 8 pages.
German Patent Office; Search Report in German Patent Application No. 10 2012 013 242.5 dated Mar. 28, 2013; 8 pages.
European Patent Office; Search Report in European Patent Application No. 14 004 414.0 dated May 12, 2015; 11 pages.
U.S. Patent and Trademark Office; Office Action in U.S. Appl. No. 14/579,296 dated Nov. 4, 2015; 33 pages.

(56) References Cited

OTHER PUBLICATIONS

U.S. Patent and Trademark Office; Office Action in U.S. Appl. No. 14/579,341 dated Nov. 5, 2015; 33 pages.
Korean Patent Office; Office Action in Korean Patent Application No. 2014-7036831 dated Jul. 8, 2016; 12 pages.
Korean Patent Office; Office Action in Korean Patent Application No. 2014-7036658 dated Jul. 8, 2016; 12 pages.
Chinese Patent Office; Examination Report in Chinese Patent Application No. 201510069359.9 dated Jun. 1, 2016; 19 pages.
Chinese Patent Office; Examination Report in Chinese Patent Application No. 201510069345.7 dated Jun. 1, 2016; 13 pages.
Chinese Patent Office; Office Action in Chinese Patent Application No. 201510069344.2 dated Jul. 1, 2016; 21 pages.
Chinese Patent Office; Office Action in Chinese Patent Application No. 201510069555.6 dated Jun. 29, 2016; 15 pages.
Chinese Patent Office; Office Action in Chinese Patent Application No. 201510069356.5 dated Jun. 27, 2016; 27 pages.
Korean Patent Office; Office Action in Korean Patent Application No. 2014-7036838 dated Jul. 18, 2016; 11 pages.
Korean Patent Office; Office Action in Korean Patent Application No. 2014-7036836 dated Jul. 18, 2016; 12 pages.
Chinese Patent Office; Examination Report in Chinese Patent Application No. 201510069525.5 dated Mar. 22, 2017; 13 pages.
Chinese Patent Office; Office Action in Chinese Patent Application No. 201380033727.3 dated Apr. 1, 2016; 17 pages.
Korean Patent Office; Office Action in Korean Patent Application No. 2014-7036835 dated Jul. 8, 2016; 12 pages.
Korean Patent Office; Office Action in Korean Patent Application No. 2014-7036833 dated Jul. 8, 2016; 12 pages.
Korean Patent Office; Office Action in Korean Patent Application No. 2014-7036839 dated Jul. 18, 2016; 12 pages.
U.S. Patent and Trademark Office; Office Action in U.S. Appl. No. 14/579,465 dated Jul. 29, 2016; 49 pages.
Korean Patent Office; Office Action in Korean Application No. 2014-7036837 dated Jul. 18, 2016; 10 pages.
Chinese Patent Office; Office Action in Chinese Patent Application No. 201510069342.3 dated Jun. 22, 2016; 27 pages.
U.S. Patent and Trademark Office; Office Action in U.S. Appl. No. 14/579,515 dated Jul. 27, 2016; 23 pages.
Wikipedia; Publication entitled "Pin Tumbler Lock" published Apr. 13, 2010; 1 page.
lock-picking.org; Publication entitled "Lock Picks for Cars" published May 17, 2008; 1 page.
European Patent Office; Examination Report in related European Patent Application No. 14 004 406.6 dated Mar. 12, 2018; 4 pages.

\* cited by examiner

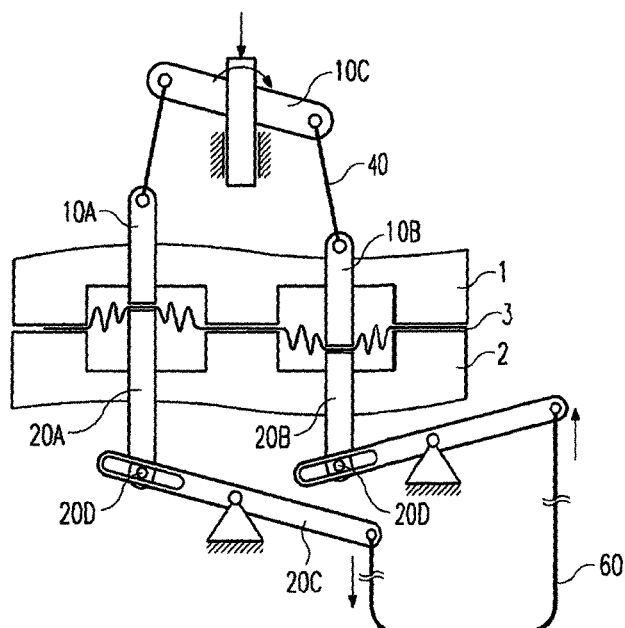
Fig. 15
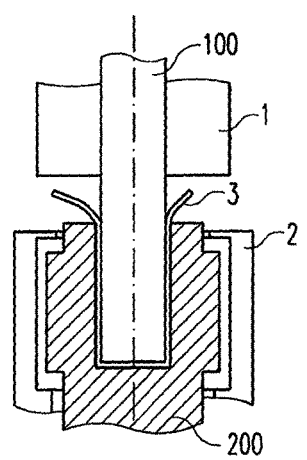
Fig. 16
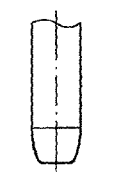 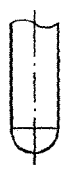 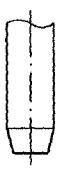 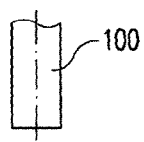
Fig. 17A   Fig. 17B   Fig. 17C   Fig. 17D
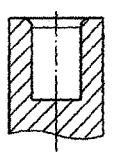   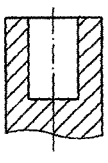
Fig. 18A   Fig. 18B   Fig. 18C   Fig. 18D

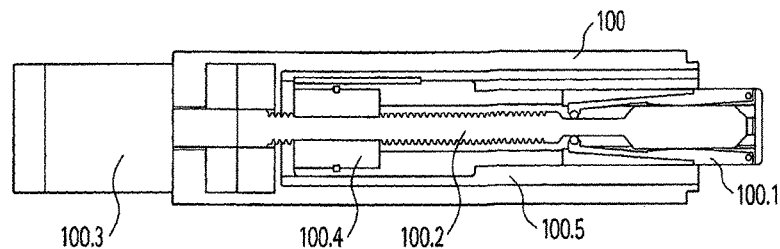
Fig. 22
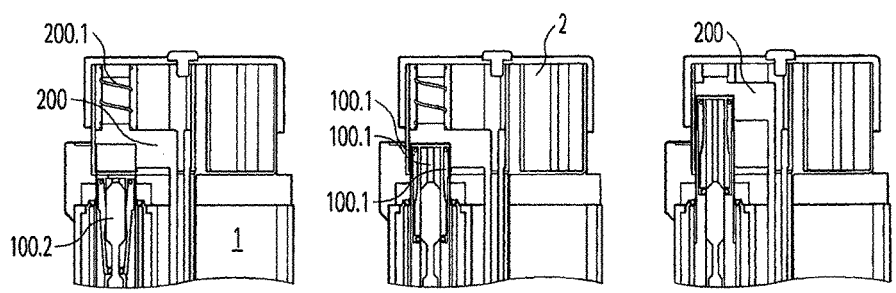
Fig. 23A  Fig. 23B  Fig. 23C
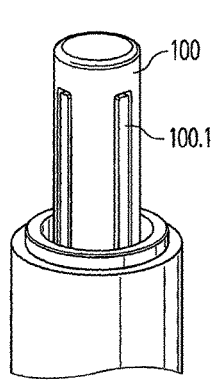 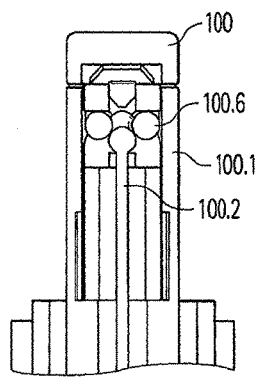
Fig. 24A  Fig. 24B

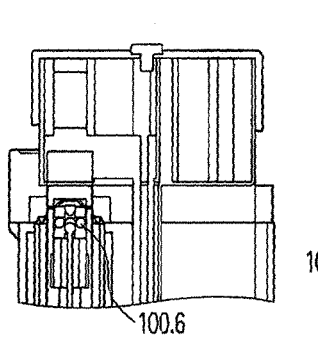 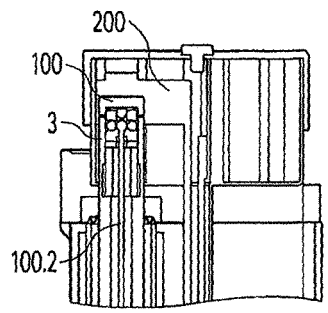 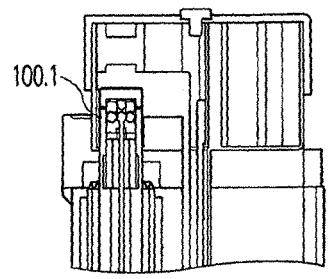
Fig. 25A     Fig. 25B     Fig. 25C
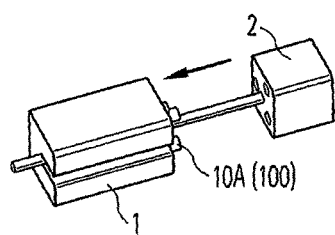 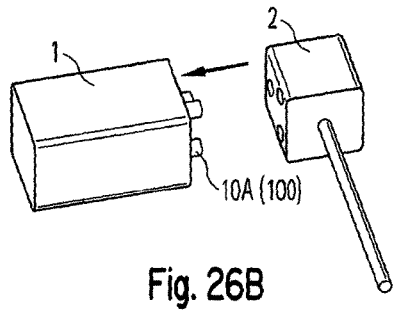
Fig. 26A     Fig. 26B
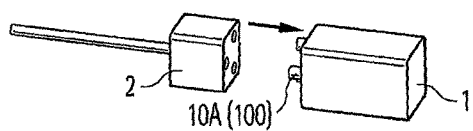
Fig. 26C

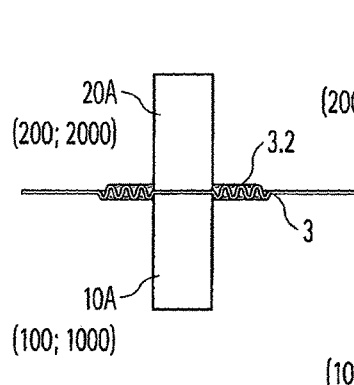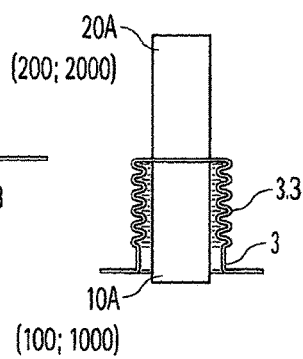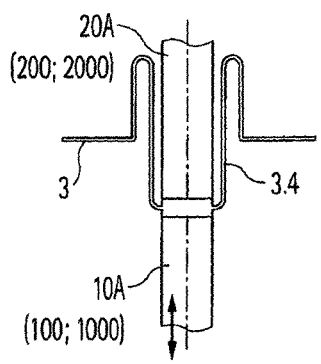
Fig. 30A     Fig. 30B     Fig. 30C
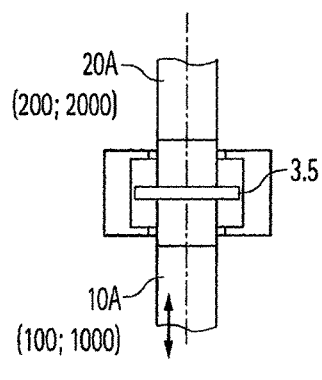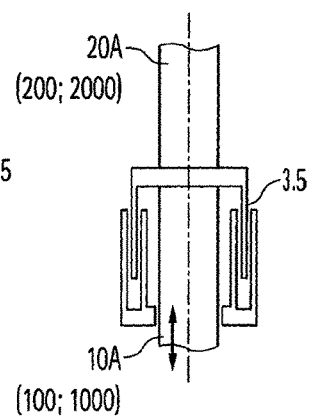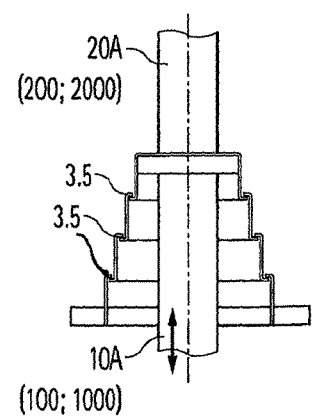
Fig. 31A     Fig. 31B     Fig. 31C

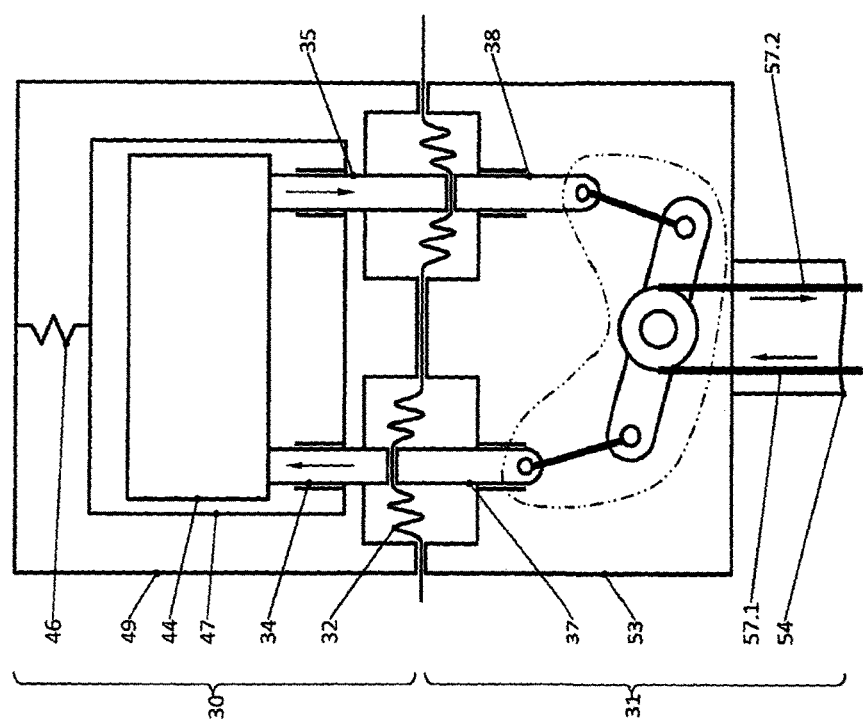

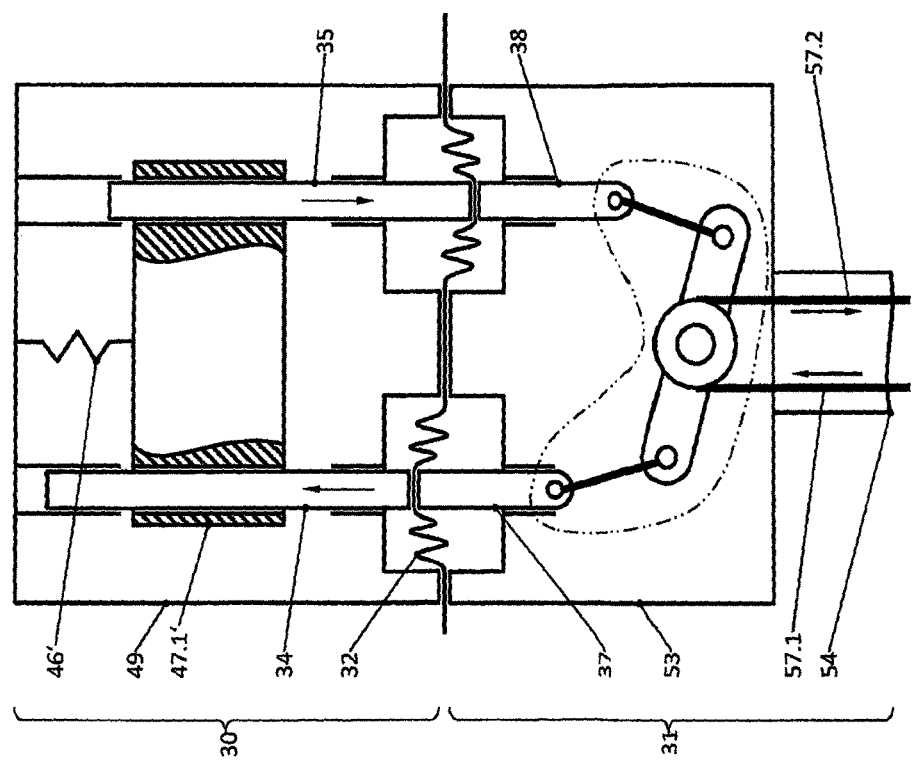

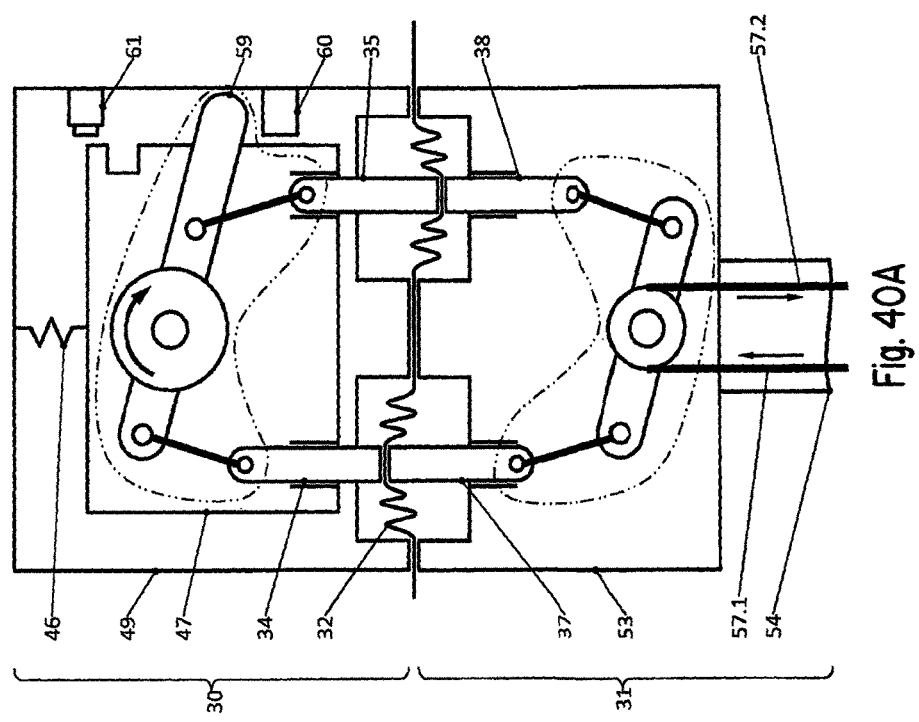

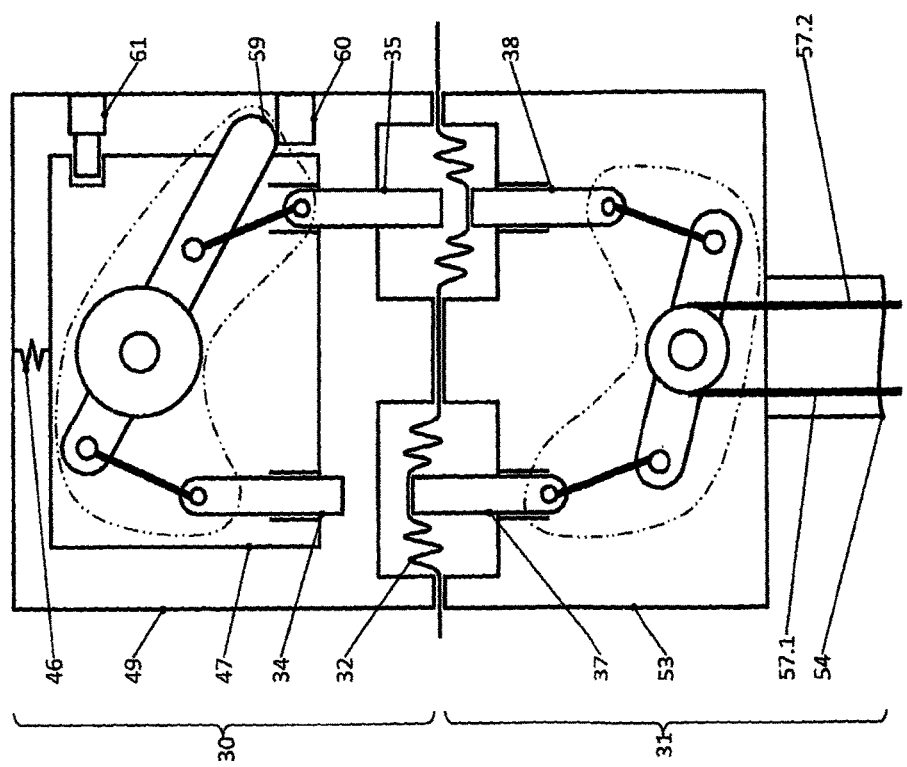

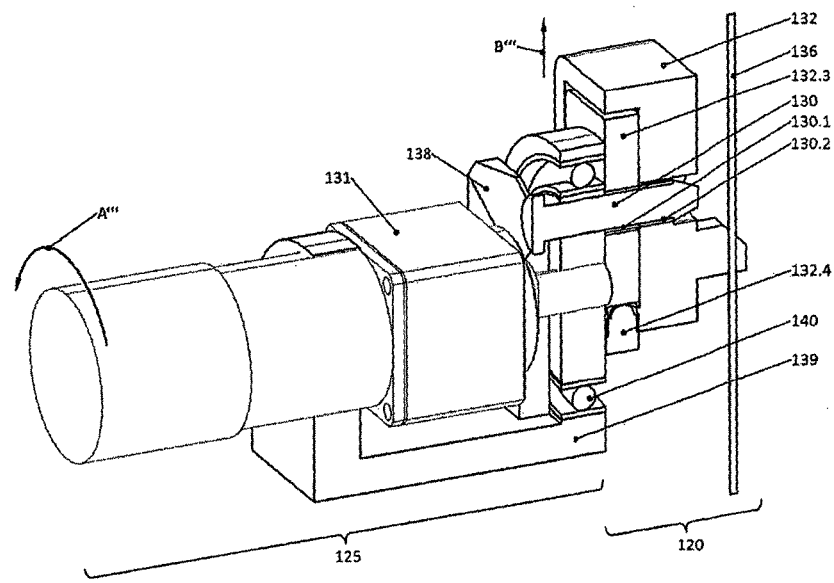
Fig. 50
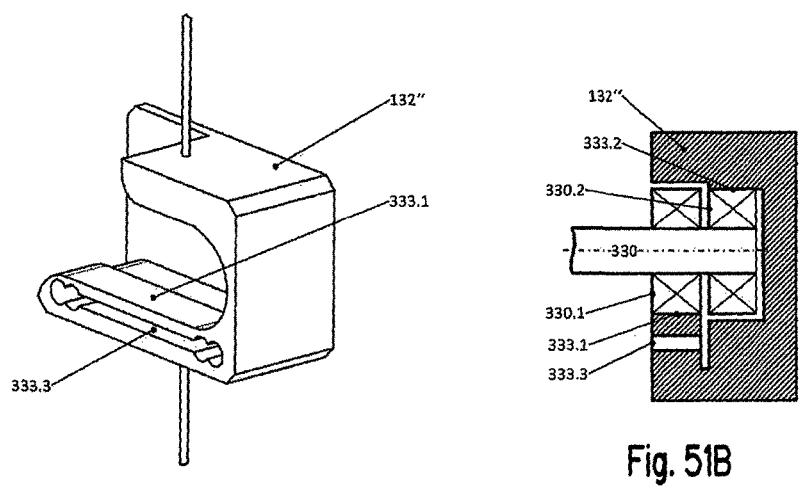
Fig. 51A
Fig. 51B

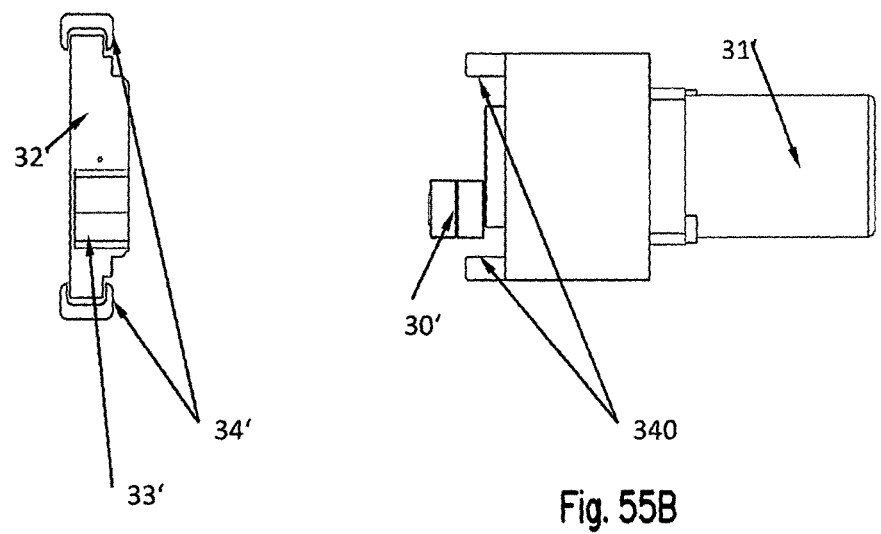
Fig. 55A
Fig. 55B
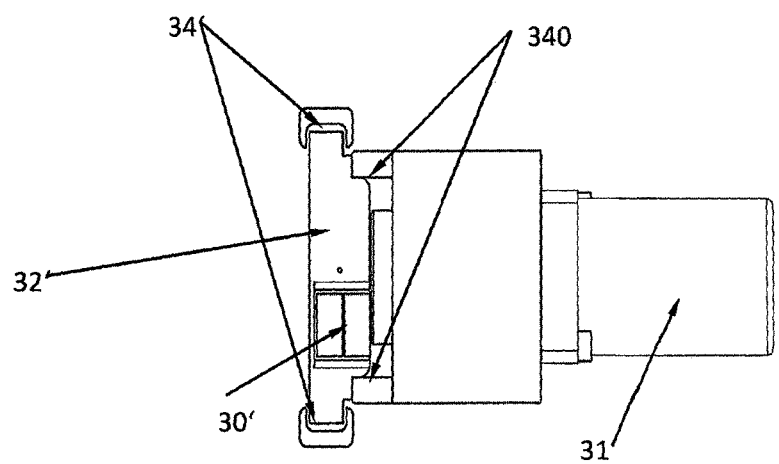
Fig. 55C

SURGICAL INSTRUMENT, ARRANGEMENT AND DRIVE TRAIN ARRANGEMENT FOR A SURGICAL INSTRUMENT, IN PARTICULAR A ROBOT-GUIDED SURGICAL INSTRUMENT, AND SURGICAL INSTRUMENT

CROSS-REFERENCE

This application is a continuation of International Patent Application No. PCT/EP2013/001917, filed Jun. 28, 2013 (pending), which claims priority to DE 10 2012 013 242.5 filed Jul. 3, 2012, DE 10 2013 004 230.5 filed Mar. 11, 2013, DE 10 2013 004 487.1 filed Mar. 14, 2013, DE 10 2013 005 493.1 filed Mar. 28, 2013, and DE 10 2013 007 761.3 filed May 6, 2013; and is related to U.S. patent application Ser. No. 14/579,221 (Pending), U.S. patent application Ser. No. 14/579,296 (Pending), U.S. patent application Ser. No. 14/579,341 (Pending), U.S. patent application Ser. No. 14/579,398 (Pending), U.S. patent application Ser. No. 14/579,465 (Pending), U.S. patent application Ser. No. 14/579,515 (Pending), and U.S. patent application Ser. No. 14/579,597 (Pending), each filed Dec. 22, 2014, the disclosures of which are incorporated by reference herein in their entirety.

TECHNICAL FIELD

One aspect of the present invention relates to a surgical instrument assembly, a manipulator surgical system with a manipulator-guided instrument assembly of this type, and a method for equipping a manipulator thereof.

BACKGROUND

By way of example, a manipulator surgical system having a manipulator-guided surgical instrument is known from EP 1 015 068 A1, the degrees of freedom of which are actuated by a drive train assembly in the manipulator, which, in particular, makes the attachment of the instrument to the manipulator more difficult with respect to sterility requirements.

DE 10 2009 060 987 A1 discloses a surgical manipulator instrument having its own drive unit for actuating degrees of freedom for the instruments, which has a mechanical interface with a coupling element that engages in an undercut protrusion of a further coupling element, without addressing sterility requirements.

SUMMARY

An object of one aspect of the present invention is to make available an improved surgical instrument.

A further aspect of the present invention relates to a drive train assembly for actuating at least one degree of freedom of an end effector of a surgical instrument, in particular a robot-guided surgical instrument, a drive module and an instrument shaft of such an instrument, an instrument having such an instrument shaft and/or drive module, a manipulator assembly having at least one such instrument, which is guided by a manipulator, and a method and a guidance means for guiding such an instrument, in particular its drive and/or a manual teleoperation means.

A robot-guided minimally invasive surgical instrument has, in general, an instrument shaft. With an instrument shaft partially inserted by a trocar, a distal, or intracorporeal instrument shaft end can still be moved by the robot in a maximum of four degrees of freedom (three axes of rotation by the trocar point and one translation in the direction of the shaft axis).

In order to have available more degrees of freedom in a minimally invasive operating field, the mounting of an end effector in an articulated manner on the distal end of the instrument shaft, and additionally, the actuation thereof by a drive train assembly, is known from WO 2009/079301 A1. By way of example, a clamp can be closed, or an endoscope optics can be reoriented, in this manner.

In order to give a teleoperator, who operates the surgical robot, a haptic feedback from the operating field, WO 2009/079301 A1 proposes that a force-torque sensor having six axes be disposed between the instrument shaft and the end effector bearing.

One disadvantage of this solution can be illustrated on the basis of FIG. 34: an instrument shaft 20 is shown there, as shall be described in greater detail below, on which an end effector, in the form of a clamp having two blades 2.1, 2.2, is disposed. The blade 2.1 can be adjusted in its rotational degree of freedom $q_1$ in relation to the instrument shaft by means of two drive trains 21, 22 running in opposite directions, the blade 2.2 can be adjusted in a corresponding manner. If the clamp engages with a lumen (not shown), the reaction forces $F_{E1}$ and $F_{E2}$, respectively, act thereon. These forces do not exert any forces in the instrument shaft 20 in the constellation depicted in FIG. 34, because their resultant force disappears. Accordingly, a force-torque sensor, such as that proposed in WO 2009/079301 A1, cannot transmit feedback pertaining to the forces exerted by the clamp to the teleoperator, because it does not register any forces or torques in the instrument shaft from the actual exerted clamping forces $F_{E1}$, $F_{E2}$.

An object of one aspect of the present invention is to make available an improved surgical instrument, and/or to improve the control thereof.

A further aspect of the present invention relates to a surgical instrument, in particular a robot-guided surgical instrument, having an instrument shaft with at least one degree of freedom and a drive unit for the actuation thereof, as well as an instrument shaft and a drive unit.

A robot-guided surgical instrument having four dive units is known from WO 2011/143022 A1, which are arranged on a base plate in the manner of pie slices, and each have numerous drive modules. The drive modules each have numerous displaceable or rotatable output drive links for actuating input drive links of an instrument shaft connected to the drive unit.

The drive units can each be actively telescoped in relation to the base plate, in order to retract or extend their instrument shaft through a common guide cannula. The output drive links are distal in relation to the input drive links, or are in front thereof in a coupling device, which is parallel to the longitudinal axis of the instrument shaft, and are elastically pre-tensioned in this distal direction, in order to ensure contact without play.

An object of one aspect of the present invention is to make available an improved surgical instrument.

A further aspect of the present invention relates to a surgical instrument, in particular a robot-guided and/or minimally invasive surgical instrument, as well as a drive module and an instrument shaft for such an instrument, and a method for the connection thereof.

By way of example, a robot-guided, minimally invasive instrument having an instrument shaft, is known from WO 2011/143022 A1, which is inserted into the patient by a robot through a natural or artificial little hole. In order to actuate intracorporeal degrees of freedom, in particular for an end effector, an extracorporeal drive module is releasably connected to the instrument shaft.

An object of one aspect of the present invention is to make available an advantageous surgical instrument.

According to one aspect of the present invention, a surgical instrument assembly, in particular a manipulator-guided surgical instrument assembly, has a modular motor drive unit, which has an output drive assembly with one or more output drive elements. In the present case, an output drive element is understood to be, in particular, a single- or multi-part element or component, which can be directly or indirectly actuated, or adjusted in an adjustment direction, respectively, by a motor, in particular an electric motor, of the drive unit, and is provided for actuating a degree of freedom of the instrument. The drive unit can be provided with power and/or controlled in an embodiment functioning in a wireless manner, or having wire connections.

The instrument assembly furthermore has an instrument shaft, which is provided in one embodiment for being partially inserted in a patient, in particular through a hole for minimally invasive surgery, in particular also for endoscopy. The instrument shaft can be designed such that it is partially or entirely stiff or flexible, and/or have an end effector, in particular a scalpel, a scissors, forceps, clamp, an optical recording and/or lighting means, in particular a fiber optics end, a CCD chip (a so-called "chip-on-the-tip" endoscope), an LED, or suchlike. In this respect, it can also represent an actuatable, in particular a bendable, endoscope of an instrument shaft, as set forth in the present invention. An instrument shaft as set forth in the present invention has, in general, one or more degrees of freedom, in particular one or more degrees of freedom for positioning, in particular for orienting, and/or for actuating, an end effector. In a further development it has two, three, or more degrees of freedom, in particular a rotational degree of freedom, for orienting and/or one or more, in particular a maximum of one, degree of freedom for actuating, in particular for opening or closing, an end effector. For the actuation, it has a drive assembly having one or more input drive elements. In the present case, an input drive element is understood to be, in particular, a single- or multi-part element or component, which can be directly or indirectly actuated, or adjusted in an adjustment direction, respectively, by means of an output drive element allocated thereto, and is provided for actuating a degree of freedom of the instrument. For this purpose it can be coupled to the end effector, in particular in a unidirectional or bidirectional manner, mechanically in one embodiment, in particular by means of one or more pull cables, rods, or gearwheels, hydraulically, pneumatically, or suchlike, wherein a unidirectional coupling is understood, in particular, to be such a coupling by means of which the degree of freedom can be actuated by an adjustment of the input drive element in only one sense of direction, by means of a pull cable in only one pulling direction, for example, and a bidirectional coupling is understood to mean, accordingly, a coupling, in particular, by means of which the degree of freedom can be actuated by an adjustment of the input drive element in opposite directions, by means of a push rod, for example, in a pulling and a pushing direction.

The instrument shaft can be releasably connected to the drive unit, and the output drive assembly and the drive assembly can be coupled to one another, by means of a mechanical interface. In a further development, the instrument shaft is releasably connected to the drive unit, and the output drive assembly and the drive assembly are coupled to one another by means of the mechanical interface. The instrument assembly is then also referred to, in short, as the instrument. In one embodiment, however, two or more different drive units and/or two or more different instrument shafts can also be provided, which can be selectively connected to an instrument shaft or a drive unit, and which can differ, in particular, in the number of actuatable degrees of freedom. For a more compact depiction, in the present case an instrument assembly is referred to in general as a set of one or more drive units and one or more instrument shafts, which can be, or are, releasably connected to one another.

The instrument assembly, or the instrument, respectively, in particular the drive unit or the instrument shaft, is releasably attached to a manipulator in one embodiment, and for this purpose, can have a corresponding attachment interface in a further development. Accordingly, one aspect of the present invention relates to a method for equipping a manipulator, wherein one drive unit and one instrument shaft are releasably connected to one another, and their output drive assembly and the drive assembly are coupled to one another by means of the mechanical interface. The manipulator can have one or more, in particular at least six, preferably seven or more, degrees of freedom in one embodiment, for guiding (redundantly) the instrument, in particular for positioning its end effector in a patient.

One factor of the present invention relates to the design of the mechanical interface, by means of which the output drive and drive assembly can be, or are, coupled to one another.

According to one aspect, this interface has, in each case, one one-sided linkage between one or more pairs of output and input drive elements allocated to one another. A one-sided linkage, or coupling, respectively, is understood in the present case to mean, in particular, as is typical in mechanical engineering, that a movement of the one of the output drive and input drive elements in one direction, or in one sense of direction, respectively, causes a positively driven movement of the other of the output drive and input drive elements, and a movement of the one of the output drive and the input drive elements in the opposite direction, or the opposing direction, respectively, conversely, does not cause positively driven movement of the other of the output drive and the input drive elements. In particular, a one-sided linkage can be characterized in that only pressure forces, and no tractive forces, can be directly or indirectly transferred between the output drive and the input drive elements, wherein in the present case, for a more compact depiction, anti-parallel pairs of forces, i.e. torques, are also referred to in general as forces. A one-sided linkage can accordingly be characterized in that only a torque in one direction can be directly or indirectly transferred between an output drive and an input drive element, whereas in the opposite direction, at least substantially, no torque can be transferred. Accordingly, a two-sided linkage is understood, in the present case, to mean, in particular, that movements in opposing directions of the output drive or input drive elements are transferred in a positively driven manner to the respective other element, in particular, direct or indirect pressure and tractive forces, or torques in opposing directions, respectively, can be transferred between the output drive and input drive elements.

A one-sided linkage can act advantageously via a sterile barrier. In particular, in one embodiment an output drive element and an input drive element allocated thereto can be disposed on opposite sides of a sterile barrier, and be in contact therewith, wherein at least one of the output drive and input drive elements is not connected to the sterile barrier, or can be detached therefrom, respectively. In this manner, a sterile barrier can be disposed between the drive unit and the instrument shaft in a simple and compact manner.

According to one aspect, the mechanical interface, by means of which the output drive and drive assembly can be coupled, or are coupled, respectively, to one another, has at least one cut-out in each case, that is formed in an element of one or more pairs of output drive and input drive elements allocated to one another, and one pin in each case, which is formed on the other element of this pair, and which can be, or is, respectively, inserted in this cut-out. In particular, one or more output drive elements can thus have one or more pins in each case, and the input drive elements allocated thereto can have corresponding cut-outs. Likewise, one or more input drive elements can each have one or more pins, and the output drive elements allocated thereto can have corresponding cut-outs.

According to one aspect, the pin, or pins, respectively, in the respective cut-outs can be, or are, respectively, expanded radially, in particular elastically and/or by separate bodies, such that the pin can be, or is, respectively, fixed, in particular axially and/or non-rotatably, in the cut-out. In one embodiment the pin can be, or is, fixed in the cut-out in a friction-locking manner, by means of the radial expansion. Additionally or alternatively, the pin can be, or is, fixed in the cut-out in a form-locking manner by the radial expansion. A sterile barrier can be disposed, in particular, between the pin and the cut-out, in particular, it can be, or is, clamped therebetween, and is thus disposed in a simple and compact manner between the drive unit and the instrument shaft.

In one embodiment a clamping means is provided for the radial expansion of one or more of each of the pins inserted in a cut-out in the mechanical interface. This clamping means can be manually or mechanically actuated in a further development, in particular by a separate, preferably electric motor powered, clamping means drive. It can be actuated, in particular, mechanically, hydraulically, pneumatically and/ or by electromagnetic means. By way of example, a clamping means drive can be path- or force-controlled such that, after an insertion of a pin in the cut-out, it expands radially, in particular by means of an adjustment or actuation of the drive assembly. The pin can be designed such that it is an integrated part, or a separate part, of the output drive or input drive element, respectively, in particular as a separate and/or elastic body, which is connected to the rest of the output drive or input drive element such that it can be released, or cannot be released, therefrom, in particular in a material-bonded manner, preferably by means of an adhesive.

For the elastically radial expansion, the pin, in particular its elastic body, can be made of plastic in a further development, in particular it can be made of polyurethane and/or silicone. For a non-elastic expansion, the pin can have one or more separate, in particular lamellar, bodies, that can be displaced radially, in particular that can be pivoted radially outward about an axis, or can be displaced in a translational manner in the pins, or guided into the rest of the output drive or input drive elements, respectively, and by radial displacement outward, in particular by pivoting, can radially expand the pin, as set forth in the present invention.

In one embodiment, the pin can have a through or blind internal bore, which is pressurized, for example, hydraulically or pneumatically, in order to expand the pin radially. A stud in the clamping means can be inserted in a through hole in the pin, and have a flange on a side lying opposite a clamping means drive, the diameter of which is greater than the through hole. By tensioning the flange against the hole by means of the clamping means drive, the pin can be axially compressed between the flange and the clamping means drive, such that the pin expands radially. Likewise, the stud can have a contour that expands radially in the axial direction, in particular a conical contour, such that an axial displacement of the stud in the pin expands the pin radially, in particular in an elastic manner, or radially outward by the displacement of separate bodies.

According to another aspect, a wavelike gap is formed in a radial direction between the cut-out and the pin inserted therein in which an intermediate element assembly, having one or more intermediate elements, is disposed, which can be—in particular by means of a cage permanently connected to the drive unit or the instrument shaft—displaced radially, and are guided such that they are axially fixed in place. If the pin (the cut-out) is then displaced axially, its (their) wavelike outer (inner) wall facing the cut-out (the pin) is displaced in a corresponding manner. This adjusts the corresponding intermediate element in the radial direction in a form-locking manner, which causes, on its part, a corresponding axial displacement of the cut-out (the pin) in a form-locking manner. In this manner, an axial displacement, in particular, of the pin, or the cut-out, respectively, can be transferred, in a positively driven manner, to the cut-out, or the pin, respectively, such that it is form-locking. A sterile barrier can be disposed, in turn, in particular between the pin and the cut-out, in particular between the pin and the intermediate element assembly, or between the intermediate element assembly and the cut-out, in particular such that it is, or will be, clamped therein, and thus, be disposed in a simple and compact manner between the drive unit and the instrument shaft.

According to one aspect, the mechanical interface, in each case, has a tilt lever for coupling one or more pairs of output drive and input drive elements. In the present case, a tilt lever is understood to be, in the typical manner, in particular, a lever, which is rotatably supported at one location, in particular on an end, and at a location axially spaced apart therefrom, in particular at an opposite end, is positively driven in a form-locking manner by a rotatable or displaceable connecting member. A sterile barrier can be disposed, in particular, between the tilt lever and the connecting member, in particular, it is, or can be, clamped therebetween, and thus disposed in a simple and compact manner between the drive unit and the instrument shaft. In particular, an output drive element can be designed as the tilt lever, and an input drive element allocated thereto can be designed as the connecting member. Likewise, an input drive element can be designed as the tilt lever, and an output drive element allocated thereto can be designed as the connecting member.

In an embodiment of one of the aforementioned aspects, one or more output drive elements of the output drive assembly can be guided or actuated such that it can be adjusted in a translational manner. By way of example, an output drive element can form an output drive axle of a linear motor, or can be coupled to such. Additionally, or alternatively, one or more input drive elements of the drive assembly can be guided or actuated such that it can be adjusted in a translational manner. By way of example, an input drive element can form, or be coupled to, a rod, which is connected in an articulated manner to an end effector. Likewise, an input drive element can also, by way of example, be connected to a pull cable for actuating a degree of freedom of an instrument.

Likewise, one or more output drive elements of the output drive assembly can be guided or actuated such that it can be adjusted in a rotational manner. By way of example, an output drive element can form, or be coupled to, an output drive axle of a rotation motor. Additionally, or alternatively, one or more input drive elements of the drive assembly can be guided, or actuatable, such that it can be rotationally adjusted. By way of example, an input drive element can be a shaft, on which a pull cable is wound for actuating a degree of freedom of an instrument.

In an embodiment of one of the aforementioned aspects, one or more output drive elements are coupled to a coupling means such that a translational movement by the coupling means is converted to a rotational movement by the element. Likewise, one or more output drive elements can be coupled to a coupling means such that a rotational movement by the coupling means is converted to a translational movement by the element.

Additionally or alternatively, one or more input drive elements can be coupled with a (further) coupling means, such that a translational movement by the element is converted to a rotational movement by the coupling means. Likewise, one or more input drive elements can be coupled with a (further) coupling means, such that a rotational movement by the element is converted to a translational movement by the coupling means.

In a further development a coupling means can have a rotating-thrust bearing, in particular a pivot joint that can be displaced in the connecting member in a translational manner. Additionally or alternatively, a coupling means can have a rotatably mounted lever or a rotatably mounted rocker, or a lever with a pivot bearing point, which is disposed between two pickups, such as further pivot bearing points, cable attachments or suchlike, for example. In particular, a rotational movement of the coupling means can be mechanically converted to a translational movement of an output drive or input drive element in this manner. Additionally or alternatively, a coupling means can have gear teeth, in particular two sets of gear teeth that engage in one another, or mesh with one another, respectively, of which, in a further development, one is moveably mounted in a rotational manner, and the other is likewise mounted in a rotational manner, in particular as a combing spur gear, or in a translational manner, in particular as a worm gear, or a pinion gear.

In an embodiment of one of the aforementioned aspects, the instrument shaft has a flange, wherein the mechanical interface is disposed on a surface of this flange facing an end effector. In a further development the drive unit has a corresponding cut-out through which the instrument shaft is inserted, which in the present case is also referred to as a back-loading assembly. Likewise, the mechanical interface can be disposed on a surface of this flange facing away from the end effector, such that drive unit can likewise be disposed on a surface of the instrument shaft facing away from the end effector, which in the present case is also referred to as a front-loading assembly. In an alternative design, the mechanical interface can be disposed on a lateral surface of the flange on the instrument shaft, which in the present case is also referred to as a side-loading assembly.

In particular when the mechanical interface has a one-sided linkage, one or more output drive elements and/or one or more input drive elements can be pre-tensioned counter to their respective adjustment directions in an embodiment, in particular by means of a spring. In this manner, also with a one-sided linkage, an element of the other drive element can also be displaced counter to the linkage direction by means of the spring. Also with two-sided linkages, such as a radially expanded pin, an intermediate element assembly, or a tilt lever, for example, a pre-tensioning of an output drive or input drive element counter to its adjustment direction can advantageously reduce play.

Likewise, when a one-sided linkage is formed between an output drive element and an input drive element allocated thereto, in particular, a further output drive element and an input drive element allocated thereto can be provided, the one-sided linkage of which is in the opposite direction of a one-sided linkage to the one output drive and input drive element. In other words, for actuation in opposing directions, or actuation of a degree of freedom in two opposite directions, respectively, a pair of output drive or input drive elements acting in opposite directions can be provided in each case. This is understood in the present case to mean, in particular, that an actuation of an output drive element in a pair actuates, or adjusts, respectively, the other output drive element of this pair, in particular in a positively driven manner, in the opposite direction. Also with two-sided linkages, such as a radially expanded pin, an intermediate element assembly, or a tilt lever, for example, a further output drive and input drive element acting in the opposite direction can be provided, in order to advantageously present a redundant and precise actuation of the degree of freedom.

In particular, when there is a static over-determination as a result of a pair of output drive or input drive elements acting in opposing directions, a compensation means can be provided in an embodiment of the present invention, in order to compensate for tolerances. A tolerance compensation means of this type can exhibit, in particular, an elastic resiliency in an output drive or input drive element, in particular in its adjustment direction. Additionally or alternatively, a coupling means coupled to an output drive or input drive element can also exhibit an elastic resiliency in the adjustment direction of the element. Additionally or alternatively, a sterile barrier, disposed between the output drive and input drive element, can also exhibit an elastic resiliency. An elastic resiliency can be defined or formed, in particular, by an elastic material, which displays macroscopic deformations in normal operation, and/or by a corresponding shaping or flexible composition, respectively, in particular a local material weakening, preferably a constriction thereof. Likewise, a compensation means can also have a bearing or bearing axle, respectively, in particular pretensioned, that can be displaced in an adjustment direction, in particular for a coupling means coupled to an output drive or input drive element. Even without a static over-determination, a tolerance compensation of this type can be advantageous, in order to compensate for assembly or manufacturing tolerances, for example, in a kinematic chain.

In an embodiment of one of the aforementioned aspects, a front surface of an output drive element and/or a front surface of an input drive element can be flat, in particular in order to present, advantageously, a larger contact surface. Likewise, a front surface of an output drive element and/or a front surface of an input drive element can be convex, in particular in order to present, advantageously, a well-defined contact region. Additionally or alternatively, a front surface of an output drive or input drive element can have at least one projection, and a front surface, facing this element, of an input drive or output drive element that can be, or is, coupled thereto can have a corresponding cut-out, in which this projection engages.

A further aspect of the present invention relates to the sterility of the instrument. For this, according to one aspect, which can be combined with one or more of the preceding aspects or embodiments, the instrument assembly, or the instrument, respectively, has a sterile barrier, which is provided in order to encase the drive unit, in particular in an airtight manner, and is to be disposed between the drive unit and the instrument shaft, or, respectively, which encases the drive unit in a sterile manner, and is disposed between the drive unit and the instrument shaft. The sterile barrier can be designed in the manner of a foil and/or as a single use, or disposable, article in a further development.

According to one aspect, the sterile barrier has a cuff in the region of the mechanical interface, in an adjustment direction of the output drive and input drive assembly. The cuff can be formed by a sleeve in one embodiment, which extends in an axial adjustment direction, which rolls up or rolls out, or is inverted when the output drive or input drive element is adjusted axially. In general, the cuff is understood, in particular, to be a excess material of the sterile barrier, in order to compensate for, or to accompany, respectively, in particular translational, actuations of the output drive or input drive elements, which is stored in a folded or rolled-up manner during one adjustment state, and is unfolded or unrolled in another adjustment state.

In one embodiment, the cuff can be designed such that it is pre-tensioned. In this case, this means that the cuff becomes elastically deformed counter to the pre-tensioning during an adjustment movement, or actuation, respectively, of the output drive or input drive element, and with a movement in the opposite direction, returns to the pre-tensioned state. In this regard, in the present case, for a more concise explanation, an excess of material, in particular, which is provided to compensate for an actuation of an output drive or input drive element, is referred to in general as the cuff, which can either be pre-tensioned or without tension, or loose, respectively. In a further development, the cuff has a bellows, the pleating of which induces a pre-tensioning in a fundamental configuration. The pleating, or the bellows, respectively, can extend in one embodiment in an adjustment direction and/or transverse thereto, by means of which corresponding fundamental configurations and deformations can be depicted.

According to one aspect, the sterile barrier has at least one seal in the region of the mechanical interface that can be displaced without contact in a translational manner. This can be designed, in particular, in the manner of a gap seal or a labyrinth seal, and is preferably telescopic, i.e. it comprises two or more components that can be axially displaced relative to one another, and which form a seal, in particular races, preferably concentric races. Advantageously, actuations with weaker dissipation can be depicted by means of such contact-free translational seals. In a further development, in a contact-free translational seal, a transference of forces is dissipated via the sterile barrier instead of being conveyed thereby.

As has already been explained above, the sterile barrier can have a compensation means to compensate for tolerances, in particular an elastic resiliency. In a further development this can, in particular, exhibit a local thickening of the walls for this purpose, in a contact region of an output drive and/or input drive element, in particular a one-sided linkage, in order to make available a more elastic path. In a further development the elastic resiliency, in particular a local thickening of the walls, can exhibit a greater stiffness than a surrounding region of the sterile barrier, in order to improve the transference behavior. For this, the sterile barrier can have a local material modification in an embodiment of the present invention in a contact region of an input drive and/or output drive element, in particular, locally, a material having a greater or lesser stiffness than in a surrounding area of the contact region.

According to one aspect, the sterile barrier has at least one element extension in the region of the mechanical interface. This is can be, or is, respectively, attached in a releasable manner to an output drive base in one embodiment, which penetrates the sterile barrier in a destructive manner, and forms, together with the element extension, an output drive element. Likewise, an element extension can be, or is, respectively, releasably attached to an input drive element base, which penetrates the sterile barrier in a destructive manner, and, together with the element extension, forms an input drive element. By way of example, a sterile, in particular a sterilized, input drive element base of the drive assembly for the sterile instrument shaft can penetrate the sterile barrier in a destructive manner, and be connected to the element extension on the side facing away from the instrument shaft, which is then coupled inside the sterile barrier, or sterile casing, respectively, to the output drive element allocated thereto. Likewise, a sterile element extension can be disposed on the sterile barrier on the instrument shaft side, such that it makes contact in a sterile manner, before an output drive element base penetrates the sterile barrier in a destructive manner, and is connected to the element extension on the side facing the instrument shaft. In this manner, the sterility, in each case, of the instrument shaft can be ensured when coupled to a drive unit that is not sterile, which is encased by the sterile barrier.

A further aspect of the present invention relates to the attachment of a drive unit and an instrument shaft to one another. For this, according to one aspect, which can be combined with one or more of the preceding aspects or embodiments, respectively, the instrument assembly, or the instrument, respectively, has an attachment element for establishing a releasable connection to the drive unit, which is provided such that is can be disposed, preferably exclusively from the outside, on one of the surfaces of the sterile barrier facing away from the drive unit, or which is disposed exclusively on a surface of the sterile barrier facing away from the drive unit. The attachment element can be connected to the instrument shaft in a releasable manner, in particular in a form-locking or friction-locking manner, or it can be connected in a non-releasable manner, such that it is clipped thereto, or is an integral part thereof. The sterile barrier is closed in one embodiment, at least in the contact region with the attachment element, preferably in the region of the entire mechanical interface; in particular, it can be clamped between locking projections and/or cut-outs by the drive unit and the attachment element without damage thereto, or without forming holes therein. In this manner, no sealing is necessary when attaching the instrument shaft to the encased drive unit. In a further development, the attachment element is designed accordingly without seals.

The attachment element can, in particular, be designed separately as a sterile disposable article, or an adapter that can be sterilized, and can be, or is, respectively, attached to the drive unit in a friction-locking and/or form-locking manner, in particular by means of a clip connection. In particular in combination with a one-sided linkage, the attachment and coupling functionalities can thus be separated, and divided between the attachment element and the interface.

According to one aspect of the present invention, a surgical instrument has an instrument shaft, on which an end effector is disposed, and a drive module having a drive for actuating one or more degrees of freedom of the end effector in relation to the instrument shaft. The instrument shaft and drive module can be, or are, respectively, connected, in particular in a releasable manner, to one another in one embodiment. In a further development, a sterile barrier is disposed between the instrument shaft and the drive module, in particular in order to shield a drive that is more poorly sterilizable, or not sterilizable, against a surgical environment. The surgical instrument is a minimally invasive surgical instrument in one embodiment, the instrument shaft of which is provided, or designed, for the partial insertion in a patient, in particular by means of a trocar and/or a local access point, the circumference of which, in one embodiment, corresponds at most to twice the outer circumference of the instrument shaft part that is to be inserted.

The instrument can, in particular, be a manipulator-guided instrument. For this, the instrument shaft and/or the drive module has, in one embodiment, a mechanical and/or signal-based interface for the coupling thereof to a manipulator. Accordingly, according to one aspect of the present invention, a manipulator assembly having one or more manipulators, in particular robots having six or multiple axes, which guide an inventive surgical instrument, is placed under protection.

The end effector has one, two or more translational degrees of freedom, and/or one, two or more rotational degrees of freedom with respect to, or in relation to, the instrument shaft. In one embodiment, the single-piece end effector has a translational or rotational degree of freedom, and is designed, by way of example, as an extendable needle or a rotatable scalpel blade. In another embodiment, the two-piece end effector has two rotational degrees of freedom, and is designed, by way of example, as a scissors, a clamp, or suchlike. Likewise, the end effector can, in particular, have an optics system for transmitting and/or receiving electromagnetic radiation, in particular a laser emission or endoscope lens, and/or an opening for suctioning off and/or removing gas and/or fluids, which can be rotated about one or more axes of degrees of freedom and/or can be retracted or extended.

The drive has one or more motors in one embodiment, in particular electric motors, for actuating the degree(s) of freedom of the end effector. Additionally or alternatively, the drive can also have electromagnetic, hydraulic and/or pneumatic actuators.

In order to actuate an end effector, in particular by means of a drive, a drive train assembly is provided according to one aspect of the present invention. This can be disposed in one embodiment as an instrument shaft-side drive train assembly on, in particular in, an instrument shaft of an, in particular, minimally invasive and/or manipulator-guided, surgical instrument. Additionally or alternatively, an inventive drive train assembly can be disposed as a drive module-side drive train assembly on, in particular in, a drive module of an, in particular, minimally invasive and/or manipulator-guided, surgical instrument. Accordingly, according to one aspect of the present invention, an instrument shaft and a drive module having an inventive drive train assembly are placed under protection.

A drive train assembly according to one aspect of the present invention has one or more drive trains for actuating one or more degrees of freedom of an end effector of a surgical instrument in relation to an instrument shaft by means of a drive.

A drive train can, in one embodiment, at least substantially, transfer only tractive forces, or, respectively, be designed as a flexible drive train, in particular as a pull cord, or cable, respectively. In another embodiment, a drive train can transfer pressure forces, in particular, at least substantially, only pressure forces or both tractive and pressure forces, in particular as a push bar or rod, or as a tappet. Likewise, a drive train can also, in one embodiment, at least substantially, transfer only torques and/or exhibit a gear ratio and/or a gearing. In one embodiment, a drive train is designed as a solid shaft or a hollow shaft, or as a solid rod or a hollow rod. In general, a drive train, as set forth in the present invention, transfers forces and/or movements, in particular mechanically, between the drive and the end effector, in particular in order to actuate these in a degree of freedom in relation to the instrument shaft.

According to one aspect of the present invention, a metering assembly is disposed on the drive train assembly for registering a load to one or more, in particular all, of the drive trains.

As a result, one or more so-called active, or generalized loads that act on the degree(s) of freedom of the end effector can be registered, preferably directly. A generalized or minimal force is understood to mean, in the present case, in particular in the normal manner, a load that, in the case of a, potentially virtual, movement in the degree of freedom provides physical, or potentially virtual, work. By way of example, the generalized force in a rotational degree of freedom is a torque about the axis of the rotational degree of freedom. Accordingly, a load as set forth in the present invention can, in particular, comprise, in particular be, a force, an anti-parallel pair of forces, or a torque, respectively, a tension, in particular a tractive, pressure, and/or bending tension, and/or an, in particular elastic, deformation resulting from such forces, torques, or tensions, respectively, in particular an elongation or compression.

This in turn can be explained in an illustrative manner, using FIG. 34 as an example: the clamping force $F_{E1}$ causes a torque about the pivot bearing axis of the blade 2.1 having the rotational degree of freedom $q_1$. This in turn results in corresponding loads $F_{S1}$, $F_{S2}$ in the instrument shaft-side drive trains 21, 22, and this in turn results in loads $F_1$, $F_2$ in the drive module-side drive trains 21, 22. One can see that the active, or generalized, loads are registered directly by a metering assembly on the drive trains 21, 22 and/or on the drive trains 11, 12, which act on the degrees of freedom of the end effector, and thus, in particular, can transmit an advantageous feedback from the operating field to the teleoperator. As a matter of course, in one embodiment, the surgical instrument can additionally have a metering assembly for registering a load in the instrument shaft, in particular between the instrument shaft and the end effector (bearing), and/or between the instrument shaft and the drive module, in order to register so-called passive loads as well, in addition to the active loads, in particular support or bearing loads. If, for example, the clamp in FIG. 34, in the depicted constellation, pushes its tips vertically downward, then pure bearing loads result in the pivot joints of the blades 2.1, 2.2 thereby, which are registered via such an additional metering assembly for registering a load in the instrument shaft 20, and these loads are further processed; in particular they can be transmitted to the teleoperator.

In one embodiment, there may be a further advantage in that the metering assembly for registering at least one load in the drive train assembly is disposed on the drive train assembly, and thus preferably in the interior of the instrument shaft, or on, in particular in, a drive module, and thus an advantageous, in particular a protected, metering location and/or a metering location that is removed from the operating field, or the end effector, in particular an extracorporeal metering location and/or a metering location in the proximity of the drive, can be made available.

In one embodiment of the present invention, the drive train assembly has two or more drive trains, in particular in opposing directions, for actuating the same degrees of freedom of the end effector. This is illustrated in an exemplary manner in FIG. 34: there, the blade 2.1 is actuated in its degree of freedom $q_1$ by the drive trains 21, 22 acting in opposing directions, these being, for example, two pull cables or push rods, which in turn are actuated in a translational manner by the drive trains 11, 12 acting in opposing directions, these being tappets, for example, which are actuated in opposing directions by an electric motor 13.

In one embodiment example, the metering assembly has at least one metering means, which is disposed on one of the drive trains for registering a load in this drive train. In a further development, the metering assembly has a first metering means, which is disposed in a first drive train for registering a load in this drive train, and a second metering means, which is disposed in a second drive train, in particular a drive train acting in the opposite direction, for registering a load in this drive train, wherein the same degree of freedom of the end effector can be actuated by the first and the second drive train.

In one embodiment, the drive train assembly has a first drive train for actuating a first degree of freedom of the end effector, and another first drive train for actuating another degree of freedom of the end effector. In a further development, the drive train assembly can have a second drive train for actuating the first degree of freedom of the end effector and/or another second drive train for actuating the other degree of freedom of the end effector. As a matter of course, the end effector can have further degrees of freedom and corresponding first and, potentially, second drive trains.

In a further development, the metering assembly has a first metering means, which is disposed on the first drive train for actuating the first degree of freedom of the end effector, for registering a load in this drive train. Additionally or alternatively, the metering assembly has a second metering means, which is disposed on the second drive train for actuating the first degree of freedom of the end effector, in particular acting in the opposite direction, for registering a load in this drive train. Additionally or alternatively, the metering assembly has another first metering means, which is disposed on the other first drive train for actuating the other degree of freedom of the end effector, for registering a load in this drive train. Additionally or alternatively, the metering assembly has another second metering means, which is disposed on the other second drive train for actuating the other degree of freedom of the end effector, in particular acting in the opposite direction, for registering a load in this drive train.

In one embodiment there are two or more metering means, which are disposed on two drive trains for actuating the same degrees of freedom of the end effector, in particular in opposing directions, coupled together by signal-based technology. They can be connected to one another in particular by means of electric lines, or, in particular in a control means, they are, or can be, linked by means of a computer, in particular in an additive or subtractive manner.

As a result, in one embodiment, in particular a shared load, in particular a pre-tensioning, can be compensated for by means of signals, at least substantially, in two drive trains for actuating the same degree of freedom, and thus, preferably, the resulting active, or generalized, load can be determined in a direct manner. In general, in one embodiment a first and a second metering means, which are disposed on two drive trains for actuating the same degree of freedom of the end effector, in particular in opposing directions, are linked to one another in a compensatory manner. A compensatory linking is understood to mean a linking of the signals from the first and second metering means, such that a predefined load, in particular a load in a predefined direction, is compensated for at least substantially, or, respectively, the common, linked signal of the first and second metering means, at least substantially, is independent of the load, which is registered by both the first as well as the second metering means.

In particular for this, the first and second metering means, which are disposed on a first or second drive train for actuating the same degree of freedom, can be linked to one another in two branches of a Wheatstone bridge circuit, in particular in two branches of a Wheatstone half-bridge circuit, which preferably lie in a series between a bridge input or supply voltage. In a further development, the metering assembly can have a third metering means, which, in particular, is disposed opposite the first metering means on the first drive train for registering a load in this drive train, and a fourth metering means, which is disposed, in particular, opposite the second metering means, on the second drive train for registering a load in this drive train, wherein the first metering means in a first branch, the second metering means in a second branch, in particular interposed in a bridge input or supply voltage in a series with the first metering means, the third metering means in a third branch, interposed in the supply or excitation voltage, in particular in parallel to the second metering means, and the fourth metering means in a fourth branch, interposed in the supply voltage, in particular in parallel to the first metering means, are linked to one another in an electric circuit, in particular a Wheatstone full-bridge circuit. As a result, in one embodiment, not only shared loads, but also different types of loads, in particular bending loads, in the same drive train can already be compensated for, at least substantially, by means of signal-based technology. Additionally or alternatively, loads that have been registered can be amplified in terms of their signals, in particular in that load components corresponding to one another, which are registered by different metering means, are combined through the linking.

One metering means of the metering assembly can, in one embodiment, have one or more strain meters for registering a mechanical load, in particular by electrical, magnetic, optical and/or acoustic means. These meters can, in particular, be, preferably foil-type, strain meter strips, the resistances of which preferably change with their elastic elongation, semi-conductor strain meters, optical, preferably fiber type, strain meters, in particular strain meters based on Bragg or Fabry-Perot technology, such as FBG strain meters ("Fiber Bragg Grating"), acoustic strain meters, such as, in particular, so-called SAW strain meters ("Surface Acoustic Wave"), piezoelectric or magnetoelastic signal transmitters, or suchlike.

In one embodiment, one or more metering means of the metering assembly are disposed on a drive train for registering, at least substantially, an axial tractive and/or pressure load in this drive train. By way of example, a strain meter strip can be, at least substantially, disposed, or oriented, respectively, in the longitudinal direction on a pull cable or push rod.

In one embodiment, one or more metering means of the metering assembly are disposed, at least substantially, in a cut-out in a drive train. As a result, the metering assembly can be protected in one embodiment. Additionally or alternatively, a protrusion of the metering assembly over the outer edge of the drive train(s) can be reduced, in particular it can be prevented, which can facilitate the manipulation, in particular the operation and/or assembly, thereof.

Additionally or alternatively, the wall thickness of the drive train can be reduced in the region of one or more metering means, in particular by the cut-out described above. As a result, the sensitivity of the metering assembly can be increased in one embodiment. In one embodiment, in order to reduce the thickness of the wall, the drive train can have a hollow chamber in the region of one or more metering means, in particular an expansion of a hollow chamber. In a further development, the drive train can have a, preferably thin-walled, sleeve, which has one or more metering means of the metering assembly disposed on the outer and/or inner surface thereof. The sleeve can be connected to the drive train with other components, in particular rods or shafts having a solid cross-section, in a material bonded manner, in particular by means of welding or adhesive.

In one embodiment, an inventive drive train assembly is disposed on, in particular in, a drive module of a surgical instrument, to which an instrument shaft, which has an end effector, can be connected, in particular in a releasable manner. The drive module-side drive train assembly can have, in particular, a mechanical interface for the coupling of an instrument shaft-side drive train assembly, for actuating an end effector, thereto. A drive module-side drive train can have, in particular, a shaft of an electric motor of the drive, or be coupled to this shaft, in particular in an articulated manner. Loads that are spaced far apart from the end effector, in particular extracorporeal loads, preferably behind a sterile barrier, or in a sterile housing of the drive module, respectively, can be registered in an advantageous manner by means of a drive module-side metering assembly.

Additionally or alternatively, an inventive drive train assembly can be disposed in one embodiment on, in particular in, an instrument shaft of a surgical instrument having an end effector, with which a drive module, which has a drive, can be connected, in particular in a releasable manner. The instrument shaft-side drive train assembly can have, in particular, a mechanical interface, for coupling a drive module-side drive train assembly thereto, which is coupled to the drive. Preferably, loads in the proximity of the end effector can be registered directly by means of an instrument shaft-side metering assembly.

A drive module-side drive train assembly and an instrument shaft-side drive train assembly, on at least one of which a metering assembly is disposed for registering loads in this drive train, are coupled, or releasably coupled, respectively, to one another in one embodiment of the present invention.

They can be coupled, or are coupled, respectively, to one another, in one embodiment, in a translational manner. In the present case, in particular, this is understood to mean that a drive module-side drive train, and an instrument shaft-side drive train coupled thereto, are moveable, or are moved, respectively, in a translational manner on the interface, in order to actuate a degree of freedom of the end effector, wherein this translational movement is, or can be, converted to a rotational movement in other drive module-side and/or instrument shaft-side drive trains. Likewise, a drive module-side drive train, and an instrument shaft-side drive train coupled thereto, can be, or are, coupled to one another in a rotational manner on the interface, wherein this rotational movement in the interface is, or can be, converted to a translational movement in other drive module-side drive train and/or instrument shaft-side drive train.

In one embodiment, a drive module-side drive train assembly and an instrument shaft-side drive module assembly, on at least one of which a metering assembly is disposed for registering loads in this drive train, can be coupled, or are releasably coupled, respectively, in a one-sided manner via an interface. In the present case, this is understood to mean that a drive module-side drive train, and an instrument shaft-side drive train coupled, or that can be coupled, thereto, have a so-called one-sided linkage, or, respectively, that only forces or torques in one direction can be transferred, in particular, only pressure forces. In a further development, a drive module-side drive train and an instrument shaft-side drive train that is, or can be, coupled thereto, have tappets lying opposite one another, preferably flush, on the interface, which are mounted such that they can be displaced, and only transfer, at least substantially, pressure forces to one another.

In one embodiment, a drive module-side drive train assembly, and an instrument shaft-side drive train assembly that is, or can be, coupled thereto, are coupled via a, preferably foil-type and/or flexible, sterile barrier. The sterile barrier can, in one embodiment, accompany translational movements of the drive train assembly on the interface with, preferably elastic, deformation thereof, and/or have moveable, in particular displaceably and/or rotatably mounted coupling elements.

As explained above, in one embodiment, preferably an active or generalized load can be directly registered by means of an inventive metering assembly, and thus improve a feedback to a teleoperator. Accordingly, according to one aspect of the present invention, a manual teleoperation means for a surgical instrument is controlled on the basis of one or more loads registered by the measurement assembly, wherein, for a more compact depiction, a regulating is also referred to in general as controlling as set forth in the present invention. A manual teleoperation means can have, in particular, one or more levers, handles, gloves, joysticks, or a so-called mirroring-instrument, the movements of which are coupled, preferably in a control manner, to the movements of the surgical instrument. Based on the loads registered by the metering assembly, a teleoperation means of this type can be actuated, in particular by means of a motor, in order to transmit a haptic feedback pertaining to the surgical process to the teleoperator. In particular, forces acting on the end effector can be exerted on the teleoperation means on the basis of loads that have been registered by the metering assembly, in order to transmit a force-feedback to the teleoperator.

Additionally or alternatively, loads registered by the metering assembly can also be used to control, in particular to regulate, the drive. By way of example, a target force that is to be exerted by a motor can be compared with an actual force in a drive train, and the motor can be regulated based on this comparison.

Accordingly, according to one aspect of the present invention, a control means for controlling a surgical instrument is configured to further process one or more loads registered by the metering assembly, in particular to control the drive and/or a manual teleoperation means on the basis of loads registered by the metering assembly. A means as set forth in the present invention can be designed in the manner of hardware and/or software, in particular it can have a central processing unit (CPU), in particular a microprocessor, preferably connected to a memory and/or bus system for transferring signals or data, in particular in a digital manner, and/or it can have one or more programs or program modules. The CPU can be configured to process commands, which are implemented in the form of a program stored in a memory system, to detect input signals from a data bus, and/or to transmit output signals to a data bus. A memory system can have one or more, in particular different, storage media, in particular optical, magnetic, solid state and/or other nonvolatile media. The program can be created such that it embodies the method described herein, or is capable of executing said method, such that the CPU can execute the steps of such a method, and can thus control the drive and/or the teleoperation means.

According to one aspect of the present invention, a surgical instrument has an instrument shaft and a drive unit that can be connected, in particular is connected, thereto in a releasable manner. The instrument is a robot-guided instrument in one embodiment. For this, in a further development, the instrument shaft and/or the drive unit have/has an interface, in particular a mechanical, signal and/or energy based, in particular electric, hydraulic and/or pneumatic, interface, for the attachment thereof to a robot. In one embodiment, the instrument is a minimally invasive surgical instrument, the instrument shaft of which is provided for partial insertion in a patient through a local, natural or artificial, hole, in particular through a body orifice, or through a trocar.

An instrument shaft according to one embodiment of the present invention has one or more degrees of freedom. In one embodiment, the instrument shaft exhibits a tube, in particular an at least substantially cylindrical tube. A degree of freedom of the instrument shaft can then, in particular, be an articulation degree of freedom for a joint between two tube sections, or an elastic degree of freedom for a flexible tube. In one embodiment, the instrument shaft has an end effector, in particular a forceps, clamp or clips, a scalpel, a drill, a needle or cannula for removing and/or introducing gases and/or fluids, and/or an optics system for transmitting and/or receiving electromagnetic radiation, in particular a fiber optics end of an endoscope or a laser. A degree of freedom of the instrument shaft can then be, in particular, a degree of freedom of the end effector, in particular a translational or rotational degree of freedom with respect to the tube, or a functional degree of freedom, in particular for opening or closing a forceps, clamp, clip, cannula and/or optics system, or suchlike. A functional degree of freedom as set forth in the present invention can, in particular, describe a movement possibility for two parts of an end effector in relation to one another. In one embodiment, the tube can have a rotational degree of freedom with respect to a proximal instrument housing of the instrument shaft.

In order to actuate a degree of freedom, the instrument shaft has one or more input drive links, in particular acting in opposing directions. An input drive link, in one embodiment, is mounted in an interface of the instrument shaft such that it is translational, or can be displaced, respectively, and/or is rotational, or can be rotated, respectively, in order to actuate a translational or rotational movement of a degree of freedom of the instrument shaft. For this purpose, it can be coupled to a tube (part) or end effector of the instrument shaft, in particular by a push rod, a pull cable or cable drum, and/or a gearing, in particular for converting translational and rotational movements into one another. In one embodiment, the instrument shaft, in particular an interface of the instrument shaft for coupling with the drive unit, has an input drive link assembly with numerous input drive links. In a further development, at least one degree of freedom of the instrument shaft can be actuated in opposing directions by two input drive links, in particular acting in opposing directions, for example a pivotable end effector can be pivoted up and down by means of two push rods running in opposite directions.

A drive unit according to one embodiment of the present invention has a housing and one or more drive modules. At least one drive module, preferably all drive modules, exhibits, in each case, a drive and an output drive link assembly having one or more moveable output drive links. The drive can have, in particular, an electromagnetic, hydraulic, or pneumatic rotational or linear motor, in particular, it can be an electric motor.

In one embodiment, the drive actuates exactly one output drive link. In another embodiment, the drive actuates two output drive links, in particular in opposing directions. One or more output drive links are mounted in one embodiment in an interface of the drive module, such that they are translational, or can be displaced, respectively, and/or rotational, or can be rotated, respectively, in order to actuate a degree of freedom of the instrument shaft by means of a translational or rotational movement. The output drive link and input drive link assemblies can be, or are, directly, or via a coupling, coupled in a one-sided manner in one embodiment. This is understood to mean, in the normal sense, that forces can only be transferred in one actuation direction from the output drive link to the input drive link, while the output drive link and the input drive link can distance themselves from one another in opposite directions. In a further development, one output drive link assembly has two output drive links that are actuated in opposing directions, in particular two push rods, which can be, or are coupled, directly or by means of a coupling, at one end to corresponding input drive links running in opposite directions. In another embodiment, the output drive link assembly and the input drive link assembly can be, or are, coupled directly or via a coupling, in a two-sided manner. This is understood to mean, accordingly, that forces in two opposing actuation directions can be transferred from the output drive link to the input drive link. In a further development, one output drive link assembly has a rotatable output drive link, in particular an output drive shaft of an electric motor or gearing, which can be, or is, non-rotatably coupled to a corresponding rotatable input drive link. For a more compact depiction, in the present case an anti-parallel pair of forces, i.e. a torque, is also referred to in general as a force.

According to one aspect of the present invention, one or more drive modules in the, in particular closed, housing of the drive unit are each moveably mounted and pre-tensioned in a coupling direction, or against the input drive link assembly. The coupling directions of two, preferably all, drive modules can be, at least substantially, parallel. Likewise, the coupling directions of two drive modules can form an angle, which is preferably less than 90 degrees, and in particular is less than 45 degrees.

In that the individual output drive links are not pre-tensioned, or not only the individual output drive links are pre-tensioned, as is proposed in WO 2011/143022 A1, specified in the introduction, but rather, according to this aspect, exclusively, or additionally, the drive module in the housing, and as a result, its output drive link assembly as a whole, is pre-tensioned, the coupling between the output drive assembly and the input drive assembly can be improved in one embodiment.

Additionally or alternatively, the weight, the installation space, and/or the expenditure can be reduced, and/or the operation thereof can be improved.

In one embodiment, a drive module has a hydraulic, pneumatic and/or elastic tensioning means, in particular at least one hydraulic or pneumatic cylinder and/or one compression and/or tractive spring, for pre-tensioning, which restrains the drive module in the housing, and is pre-tensioned in the coupling direction, or against the input drive link assembly, respectively. A hydraulic or pneumatic tensioning means can be designed such that it is switched on and off in a further development, in particular in a pressure-less state, in which it, at least substantially, exerts no force.

Advantageously the adjustment of the drive module in the housing, after removal of the excess pressure in a hydraulic or pneumatic tensioning means, does not require any appreciable operating force.

Additionally or alternatively, in one embodiment, a drive module can have a magnet assembly for pre-tensioning the drive module. The magnet assembly can have one or more permanent magnets or electromagnets, which are disposed on either the housing or the drive module. The other, either the drive module or the housing, can have one or more additional electromagnets and/or magnetically hard or soft regions, in particular at least one further permanent magnet, preferably lying opposite the permanent magnets or electromagnets, and which are magnetically attracted or repelled by these, either permanently, or when they are subjected to current.

In one embodiment, at least one permanent magnet or electromagnet is disposed on the housing on a side facing away from the instrument shaft, and, preferably lying opposite this, at least one further electromagnet or a magnetically hard or soft region, in particular at least one further permanent magnet, is disposed on the drive module. Additionally or alternatively, at least one permanent magnet or electromagnet can be disposed on the housing on a side facing the instrument shaft, and, preferably lying opposite this, at least one further electromagnet or a magnetically hard or soft region, in particular at least one further permanent magnet, can be disposed on the drive module. Additionally or alternatively, at least one permanent magnet or electromagnet can be disposed on the drive module on a side facing away from the instrument shaft, and, preferably lying opposite this, at least one further electromagnet or a magnetically hard or soft region, in particular at least one further permanent magnet, can be disposed on the housing. Additionally or alternatively, at least one permanent magnet or electromagnet can be disposed on the drive module on a side facing the instrument shaft, and, preferably lying opposite this, at least one further electromagnet or a magnetically hard or soft region, in particular at least one further permanent magnet, can be disposed on the housing. The drive module can be pre-tensioned in the housing against the input drive link assembly by means of the magnetic attraction or repulsion occurring between them.

While the pre-tensioning force decreases as the number of adjustments to the drive module in the housing increases with a pre-tensioning by a tensioning means, for example as a result of the relaxing of a mechanical spring or an increase in volume in a hydraulic or pneumatic volume, an (electro)magnetic pre-tensioning can advantageously increase with the increasing number of adjustments to the drive module in the housing.

In a further development, the magnet assembly has one or more electromagnets that can be, selectively, in particular in a controlled manner, subjected to current. In this manner, the pre-tensioning can be exerted selectively, in particular in a controlled manner. For the purpose of a more compact depiction, in the present case a regulation, i.e. the specification of a control variable on the basis of a registered actual variable, is also referred to in general as a control thereof.

In one embodiment, the magnet assembly has one or more, preferably non-magnetic, spacer elements, which prevent a direct contact between an electromagnet or a permanent magnet, on either the housing for the drive unit or the drive module, and a magnetically soft or hard region, in particular a (further) permanent magnet on the other of either the housing of the drive unit or the drive module, in order to thus avoid a magnetic short circuit, the release of which would require excessive force.

During or after the coupling of the output drive assembly and the input drive assembly, or the drive unit and the instrument shaft, respectively, according to the aspect explained above, the pre-tensioning of the drive module must be built up.

This can result, in one embodiment, as explained above, from selectively subjecting one or more electromagnets in the magnet assembly to a current. In this manner, an operator advantageously, particularly with the high demands in running an operating theater, need only exert a small amount of force in order to couple the drive unit to the instrument shaft.

Additionally or alternatively, in one embodiment, a retraction assembly, in particular a mechanical and/or magnetic retraction assembly, can be provided for retracting the drive module against the pre-tension. Thus, in one embodiment, a magnet assembly can be selectively activated, in order to remove the drive module from the input drive assembly when it is subjected to (further) pre-tensioning by a tensioning means. If the current that the magnet assembly is subjected to is reduced, preferably selectively, in a linear manner, for example, the tensioning means builds up the pre-tensioning.

A further development is based on the idea of dividing the work range of the drive for the drive module into an actuating field, in which the drive actuates the output drive link assembly for actuating a degree of freedom of the instrument shaft, and a retraction field, differing therefrom, in which the drive actuates the retraction assembly. Both fields can be separated from one another, in particular, by a mechanical stop for an output drive means of the drive, wherein the output drive means of the drive module is displaced against the pre-tensioning when it is not resting against the mechanical stop.

In that the drive can be adjusted beyond the actuating range, the drive module can thus be retracted against the pre-tensioning, preferably by means of a motor, by means of a corresponding control of the drive, which, as explained above, advantageously facilitates the coupling of the instrument shaft and the drive unit.

In an advantageous further development the drive unit has a drive module locking assembly for locking the retracted drive module in place. This can be, in particular, designed to be mechanical, preferably form- and/or friction-locking, and/or (electro)magnetic and/or pneumatic. In an exemplary design, a catch can be adjusted and secure the drive module against a pre-tensioning induced adjustment in the coupling direction. In this manner, the (more strongly pre-tensioned) drive module, or its output drive assembly, respectively, in one embodiment, can be spaced apart from the input drive assembly, also when the drive unit and instrument shaft will be, or are, connected to one another.

According to one aspect of the present invention, the coupling direction, in which the drive module is moveably mounted and pre-tensioned in the housing of the drive unit, forms an angle with the longitudinal axis of the instrument shaft, which is greater than 0 degrees, in particular is greater than 45 degrees. In one embodiment, the angle is, at least substantially, 90 degrees, or the coupling direction is, at least substantially, perpendicular, or orthogonal, respectively, to the longitudinal axis of the instrument shaft.

In that the coupling direction is not parallel to the longitudinal axis of the instrument shaft, as is the case in WO 2011/143022 A1, specified in the introduction, but rather, according to this aspect, forms an angle with the longitudinal axis that is not zero, in particular is a right angle, in one embodiment, the deformations of the instrument shaft advantageously do not interfere with the pre-tensioning, or they only interfere to a small extent therewith, because the force directions thereof are not aligned with one another. In this manner, a longitudinal oscillation in the instrument shaft, in particular, can preferably be decoupled from the pre-tensioning of the drive module, at least in part, thus improving it.

The coupling direction can, in one embodiment, at least substantially, be aligned with an actuation direction of the output drive link assembly and/or the input drive link assembly. A coupling direction is understood to mean, in particular, a direction of movement in which an output drive link or an input drive link is, or will be, moveably mounted and pre-tensioned, in order to be coupled to a corresponding input drive link or an output drive link. An actuation direction is understood to mean, in particular, a direction of movement in which an output drive link or an input drive link can move in order to actuate a degree of freedom of the instrument shaft. If, for example, an output drive link and an input drive link coupled thereto are designed as push rods, or tappets, coupled in a one-sided manner, the direction of the longitudinal axis of the pair of tappets, in which the output drive tappet is pre-tensioned against the input drive tappet, represents the coupling direction. This also represents the actuation direction in which the pair of tappets is moved by the drive in order to actuate a degree of freedom of the instrument shaft. If, in another example, an output drive link and an input drive link coupled therewith are designed as two-sided, non-rotatably, coupled shafts, the longitudinal axis direction of the shaft pair, about which the pair of tappets is rotated by the drive in order to actuate a degree of freedom of the instrument shaft, represents the actuation direction. This also represents the coupling direction in which the output drive shaft is pre-tensioned against the input drive shaft.

In one embodiment of the present invention, the instrument shaft has a mounting element for the releasable attachment, in particular in a form-locking manner, of a drive unit thereto.

The drive unit can, in one embodiment, be attachable, or attached, or will be releasably attached in a form-locking manner by means of a bayonet coupling in the mounting element. For this, either the drive unit or the mounting element can have one or more projections, which, as the result of a rotating of the drive unit in the mounting element, engage in corresponding cut-outs in the other of either the drive unit or the mounting element. Likewise, either the drive unit or the mounting element can have one or more projections, which, as the result of a displacement of the drive unit inside the mounting element, preferably by exerting a pre-tensioning force, engage in corresponding cut-outs in the other of either the drive unit or the mounting element, and/or are pushed into these. In one embodiment, a cut-out extends in a transverse direction, in particular perpendicular, to an insertion direction of the drive unit in the mounting element, such that a projection can be displaced transverse to the insertion direction in the cut-out after the insertion of the drive unit in the mounting element, and secures the drive unit in a form-locking manner against removal from the mounting element in this displaced position. Preferably this displacement occurs through the application of the pre-tensioning force, such that the displacement can be reversed after the pre-tensioning force has been released, in order to be able to remove the drive unit from the mounting element.

The mounting element can have a guide in one embodiment, that is a single-piece or multi-piece, in particular form-locking, guide for inserting the drive unit in an insertion direction. The guide can, in particular, have one or more guide grooves and/or ribs, which are designed to work together with corresponding projections or cut-outs on the drive unit. In this manner, the connecting and releasing of the drive unit and instrument shaft can be improved.

Additionally or alternatively, the mounting element in one embodiment can have an insertion opening for inserting the drive unit in an insertion direction. The insertion opening can, in a further development, be displaceable, in particular by means of a pivotable and/or displaceable lid, in order to secure the drive unit in the insertion direction, in particular to define the insertion direction.

Additionally or alternatively, the instrument shaft can have a drive unit locking assembly for locking the drive unit, in particular in a form- and/or friction locking manner, in the mounting element, in particular a moveable, preferably pre-tensioned, catch, which locks in place in the drive unit when it is placed in the mounting element.

Additionally or alternatively, the mounting element can be moveable in relation to a longitudinal axis of the instrument shaft, in particular it can be pivotable. This enables, in one embodiment, the drive unit to be first, at least in part, inserted into the mounting element, which has been moved, in particular pivoted, into a mounting position, and then to move, in particular to pivot, the mounting element into a locking position, wherein the drive unit is preferably fixed in place in a form-locking manner when the mounting element is in the locking position. In this manner the access, in particular, to the mounting element can be improved, and at the same time, an anchoring function for the drive unit in the mounting element can be integrated therein.

In one embodiment, the insertion direction can be, at least substantially, perpendicular to the longitudinal axis of the instrument shaft. The insertion opening can then be disposed, in particular, on the side facing away from the instrument shaft, in particular in order to facilitate a change in drive units when the instrument shaft is partially inserted in a patient. Likewise, the insertion opening can, in one embodiment, be disposed on the side facing the instrument shaft, in particular in order to avoid an interference between numerous cooperating surgical instruments.

In another embodiment example, the insertion direction can be, at least substantially, parallel to the longitudinal axis of the instrument shaft. The insertion opening can then in turn be disposed, in particular, on the side facing away from the instrument shaft, in particular in order to facilitate a change in drive units when the instrument shaft is partially inserted in a patient.

According to one aspect of the present invention, one or more moveable input drive links of an input drive link assembly for actuating a degree of freedom of an instrument shaft are at least substantially perpendicular to a longitudinal axis of the instrument shaft extending to a mounting element of the instrument shaft for a drive unit. In one embodiment, an interface, or a contact plane of the input drive link assembly is, at least substantially, parallel to the longitudinal axis.

In that the input drive links do not extend parallel to the longitudinal axis of the instrument shaft, as is the case in WO 2011/143022 A1 specified in the introduction, but rather, are perpendicular thereto, at least substantially, according to this aspect, deformations of the instrument shaft, in an embodiment, do not interfere, or interfere only slightly with the coupling of the output drive assembly and the input drive assembly. In this manner, a longitudinal oscillation, in particular, in the instrument shaft can preferably be decoupled therefrom, at least in part.

In particular in order to improve an insertion of a drive unit in a mounting element of an instrument shaft, in one embodiment of the present invention, an input drive link assembly of the instrument shaft and/or an output drive link assembly of the drive unit can be disposed in a recess, in particular in a coupling direction. Additionally or alternatively, the drive unit can have a displacement means, in particular a convergent and/or moveable displacement means, for displacing an input drive link assembly of the instrument shaft while inserting the drive unit in the mounting element of the instrument shaft. The moveable displacement means can have, in particular, one or more rotatable rollers, which retract input drive links of an input drive link assembly that protrude further than average, and thus level the input drive link assembly. Additionally or alternatively, the displacement means can have surfaces that converge in an insertion direction, which are chamfered or convex, in particular, for retracting the longer than average protruding input drive links. After passing over the roller(s) and/or convex surfaces, the input drive links extend, at least substantially, in a uniform manner toward the mounting element of the instrument shaft. In a further development, a surface diverging in the insertion direction, in particular such that it is chamfered or convex in the opposite direction, can adjoin a surface converging in the insertion direction, in particular a chamfered or convex surface, in order to also retract protruding input drive links when removing the drive unit from the mounting element.

A surgical instrument according to one aspect of the present invention has a drive module with one or more rotatable output drive links. In one embodiment an output drive link is an output drive shaft of an actuator for the drive module, in particular an electric motor, or a gearing coupled thereto. In one embodiment, an output drive link can rotate without limits, in another embodiment it can rotate a maximum of 360 degrees, preferably a maximum of 215 degrees.

The surgical instrument also has an instrument shaft, which can be, in particular is, releasably connected to the drive module. The instrument shaft has one or more, in particular intracorporeal, degrees of freedom.

In one embodiment, the instrument shaft has a rigid, articulated or flexible tube, on the distal end of which an end effector can be disposed, in particular a scalpel, a forceps, scissors, clamp, needle, pipette or suchlike. The end effector can have an opening for emitting or receiving electromagnetic radiation, in particular a lens for a camera or a laser, and/or for gaseous and/or liquid fluids, in particular a suction or rinsing nozzle.

The end effector can have one or more functional degrees of freedom, such as the opening and closing of a forceps or opening. Additionally or alternatively, the end effector can have one or more kinematic degrees of freedom, such as the rotation and/or displacement of a forceps or opening. An intracorporeal degree of freedom of the instrument shaft can be, in particular, a functional or kinematic degree of freedom of the end effector, or an articulated or elastic degree of freedom of the articulated or flexible tube. In one embodiment, the tube has one or more degrees of freedom about its longitudinal axis. These can be implemented by intra- and/or extracorporeal pivotal joints. For a more compact depiction, rotational degrees of freedom about the longitudinal axis of the tube are also referred to as intracorporeal degrees of freedom of the instrument shaft, because they represent a rotatability of an intracorporeal shaft end, in particular an end effector. In order to actuate one or more degrees of freedom of the instrument shaft by means of the drive module connected thereto, the instrument shaft has one or more displaceably guided input drive links, which will be, or are, coupled to the output drive link of the drive module when the drive module and instrument shaft are coupled to one another. In one embodiment, an input drive link actuates one or more degrees of freedom of the instrument shaft. Likewise, numerous input drive links can actuate the same degree of freedom. In one embodiment, an input drive link is connected to the tube or the end effector of the instrument shaft by one or more pulling and/or pushing means, such as pull cables or push rods, in particular in opposing directions, wherein the pulling and/or pushing means is preferably, at least substantially, parallel to a displacement axis of the input drive link. In one embodiment, an input drive link is displaceably guided in a form-locking manner and/or between two end stops.

According to one aspect of the present invention, a rotational movement of at least one output drive link in an interface between the drive module and the instrument shaft is thus converted to a translational, in particular linear, movement of an input drive link coupled to the output drive link.

For this, the output drive link and the input drive link can be, or are, coupled, according to one aspect, in the interface in the manner of a crossing thrust crank. According to one aspect of the present invention, the interface has a groove, in particular a straight or linear groove, and a guide element that is guided in the groove in a displaceable manner, when the output drive link and the input drive link are coupled to one another.

In one embodiment, the groove is disposed on, in particular in, the input drive link. In a further development, the groove can be transverse, in particular at least substantially perpendicular, to a displacement axis of the displaceably guided input drive link, or, respectively, it can form an angle therewith that is preferably between 45 degrees and 90 degrees. The guide element is disposed, preferably eccentrically, on the rotatable output drive link. In a further development, the axis of rotation for the rotatable output drive link is transverse, preferably at least substantially perpendicular, to a displacement axis of the displaceably guided input drive link and/or the groove. In one embodiment, in particular the rotational axis can form an angle with the displacement axis and/or the groove, in each case between 45 degrees and 90 degrees.

Likewise, the groove can conversely be disposed on the output drive link, and the guide element can be disposed accordingly on the input drive link.

The input drive link is displaceably guided, in one embodiment, on the instrument shaft. Additionally or alternatively, it can be displaceably guided on the drive module connected to the instrument shaft. In particular, the input drive link can be displaceably guided on the instrument shaft with greater play, in particular loosely, and can be displaceably guided on the drive module with less play, in particular substantially without play, when the drive module is connected to the instrument shaft. As a result, the more complex, precise guidance can be shifted to the drive module, thus allowing for the instrument shaft to be designed such that it is simpler and/or more cost-effective, in particular such that it can be more readily sterilized and/or is designed as a disposable article. As soon as the instrument shaft and the drive module are connected, the drive module assumes the—precise—guidance of the input drive link. In one embodiment the input drive link is secured to the instrument shaft such that it cannot be lost, in particular in a form-locking manner.

In one embodiment, the guide element has one or more rotatably mounted roller elements, for establishing contact with the groove. As a result, in one embodiment, the friction between the guide element and the groove can advantageously be reduced. In a further development, the guide element has a pin, on which at least one roller element is mounted in the form of a ball race on floating bearings, which can likewise represent a roller element as set forth in the present invention. For a more compact depiction, one or more concentric races, the inner(most) of which is disposed on the pin, and the outer(most) of which makes contact with the groove, and of which at least one is mounted on floating bearings on its radial inner and/or outer surface, are also referred to in general as roller elements, even if they do not execute a rolling or shifting movement. In another embodiment, numerous roller elements are disposed, distributed in the circumferential direction, between the pin and the ball race, in particular a ball, needle, or cylinder roller bearing. In another embodiment, one or more roller elements, in particular a ball, needle or cylinder roller bearing, have no outer race, are disposed on the pin, which make contact with the groove when the output drive and input drive element are coupled.

In order to couple the output drive element and the input drive element, play between the groove and the guide element in the displacement axis can be advantageous. On the other side, for the precise actuation of the instrument shaft by the drive module, a coupling in this axis without play, to the greatest extent possible, is advantageous. For this reason, a tolerance element is provided in one embodiment of the present invention, which pre-tensions the output drive link and the input drive link in the displacement axis of the input drive link when the output drive link and the input drive link are coupled to one another. In a further development, the tolerance element tensions the guide link disposed on the output drive link against the input drive link, or the tolerance element disposed on the input drive link tensions the guide element against the output drive link. In one embodiment, this tolerance element can affect a precise transference of movements between the output drive link and the input drive link, and furthermore, during coupling and decoupling, can be displaced against its pre-tensioning, thus improving the coupling and decoupling. In one embodiment, the tolerance element has a tolerance element groove, which is preferably at least substantially parallel to the groove in the interface, and in which the guide element engages when the output drive element and the input drive element are coupled.

In a further development, the tolerance element is displaceably guided on the input drive link and/or the guide element, and elastically pre-tensioned against these. Likewise, it can be designed as an integral part of the input drive link or the guide element, in particular by means of a hollow chamber, in which an integral leg can be inserted, which is supported on one or both sides.

In one embodiment, the tolerance element is displaceably guided and pre-tensioned parallel to a displacement axis of the displaceably guided input drive link. Additionally or alternatively, the tolerance element can be axially guided and pre-tensioned on the guide element. In one embodiment, the groove and the guide element, in particular a roller element of the guide element, and/or the tolerance element, exhibit complementary chamfers, in particular in opposing directions. In particular by means of the axial alignments of such chamfers, in one embodiment, the tolerance element can likewise (also) be pre-tensioned in displacement axes, and thus improve the guidance of the guide element in the groove. One or more of the chamfers can be designed to be convex, in particular arched, in a further development, preferably in the manner of an axial spherical roller bearing having asymmetrical barrel rollers.

In order to couple the output drive link and the input drive link during or after connecting the drive module and the instrument shaft, or prior to, or to decouple them from one another during the releasing of the drive module and instrument shaft, in one embodiment, the guide element is mounted such that it is axially displaceable. As a result, it can be axially inserted in, or removed from, the groove.

In a further development, the guide element, which is mounted such that it can be axially displaced, is axially pre-tensioned. In this manner, in one embodiment it can be automatically inserted in the groove, and/or be elastically secured therein.

In one embodiment, a connecting member is provided for the axial displacement of the guide element. In this manner, by rotating the output drive link, the guide element can first be displaced via the connecting member, and thus be brought into, or out of, engagement with the groove. The connecting member can have, in particular, one or more chamfers in the direction of rotation, on which a projection, preferably a collar, of the guide element slides up, by means of rotating the output drive link, and thus axially displaces the guide element. In a further development, the connecting member has two chamfers in opposing directions, spaced apart from one another in the direction of rotation, on which the projection slides up in rotational positions spaced apart from one another in the direction of rotation, and in this manner, axially displaces the guide element in opposing directions in the various rotational positions.

The rotational range for axial displacement of the guide element adjoins, in one embodiment, a rotational range of the output drive link for actuating the input drive link coupled thereto. In this manner, by (further) rotating the output drive link, the input drive link can be coupled thereto or decoupled therefrom, and subsequently, or prior thereto, respectively, the input drive link can be actuated.

The guide element can be axially displaceably mounted and pre-tensioned on the output drive link or the input drive link. Likewise, the guide element can be axially displaceably mounted and pre-tensioned together with the output drive link or the input drive link. In particular, for this purpose the output drive link can be displaceably mounted and pre-tensioned on the drive module and/or the input drive link on the instrument shaft, preferably parallel to the rotational axis of the output drive link.

In order to couple the output drive link and the input drive link to one another during or after the connection of the drive module and instrument shaft, or to decouple them, before or during the releasing of the drive module and instrument shaft, in one embodiment a guide wall of the groove has an opening for inserting the guide element by rotating the output drive link. As a result, the guide element can be rotated into the groove, or rotated out of the groove, respectively. The opening can be formed, in particular, by a shortened leg of an open, or U-shaped, or otherwise closed or O-shaped pair of legs, which in turn can define the groove.

It can be advantageous, in particular for detecting a coordinate of a degree of freedom of the instrument shaft on the basis of the rotational position of the output drive link coupled thereto, if the output and input drive links, or the guide element and groove, respectively, are coupled to one another, at least substantially, in a one-to-one correspondence, such that each position of the input drive link in its displacement axis precisely corresponds to a rotational position of the output drive link.

In particular, in one embodiment, the groove is therefore designed such that it is asymmetrical to the rotational axis of the output drive link and/or a displacement axis of the input drive link. In a further development it extends, a least substantially, only as far as this rotational axis.

In one embodiment, the input drive link is connected to exactly one pulling or pushing means, which is, at least substantially, parallel to a displacement axis of the input drive link. As a result, a movement of the input drive link can be precisely and readily converted to an actuation of a degree of freedom of the instrument shaft.

A surgical instrument according to the present invention can be used, in particular, as a minimally invasive and/or robot-guided instrument. For this, in one embodiment, the instrument, in particular the instrument shaft and/or the drive module, has an interface for connecting to a robot. According to one aspect of the present invention, a robot having an instrument connected to it, preferably releasably, via an interface, is placed, accordingly, under protection, as it is disclosed here. Likewise, a drive module, or an instrument shaft, respectively, for a surgical instrument of this type is placed under protection, which has one or more grooves or guide elements of the interface disclosed here for the surgical instrument in order to couple corresponding guide elements, or grooves, respectively of the instrument shaft, or drive module, respectively.

According to one aspect of the present invention, during or after a connecting of the drive module and the instrument shaft of a surgical instrument of the type described above, the guide element(s) is/are rotated into or axially inserted in the corresponding groove(s), in order to couple the output drive link(s) and input drive link(s). To decouple these, during or prior to the releasing of the drive module and the instrument shaft, the guide element(s) is/are rotated out of the corresponding groove(s), or axially removed therefrom.

BRIEF DESCRIPTION OF THE FIGURES

Further advantages and features can be derived from the dependent claims and the embodiment examples. Shown are, in part schematically:

FIGS. 11 to 15: various couplings of an instrument shaft-side drive train and an inventive mechanical interface;

FIG. 16: mechanical interfaces of instrument assemblies according to further embodiments of the present invention;

FIGS. 17A-17D, 18A-18D, 19A-19D: various embodiments of pins and cut-outs of the interface in FIG. 16;

FIG. 22: a pin and a clamping means of the instrument assembly in FIG. 21;

FIGS. 23A-23C: the steps of the strain-controlled coupling process for the instrument assembly in FIG. 21;

FIGS. 24A-24B: mechanical interfaces of instrument assemblies according to further embodiments of the present invention;

FIGS. 25A-25C: the steps of the strain-controlled coupling process for the instrument assembly in FIGS. 24A-24B;

FIGS. 26A-26C: various assemblies or joining directions, respectively, of an instrument shaft on a drive unit for an instrument assembly according to further embodiments of the present invention;

FIGS. 30A-30C: mechanical interfaces of instrument assemblies according to further embodiments of the present invention, with a sterile barrier, having a cuff in the adjustment direction;

Figures 32A, 32B:
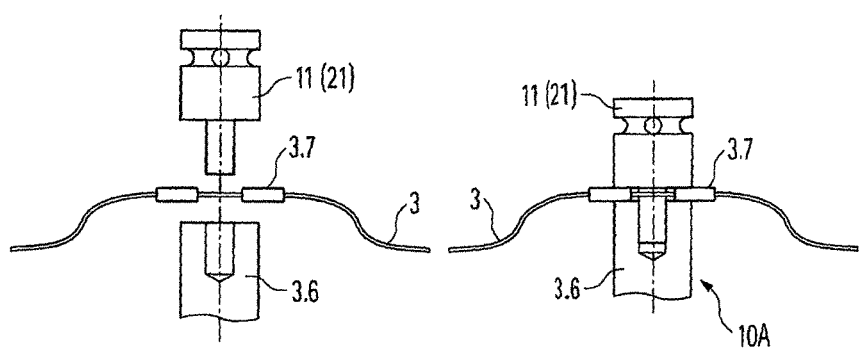
Figure 33A:
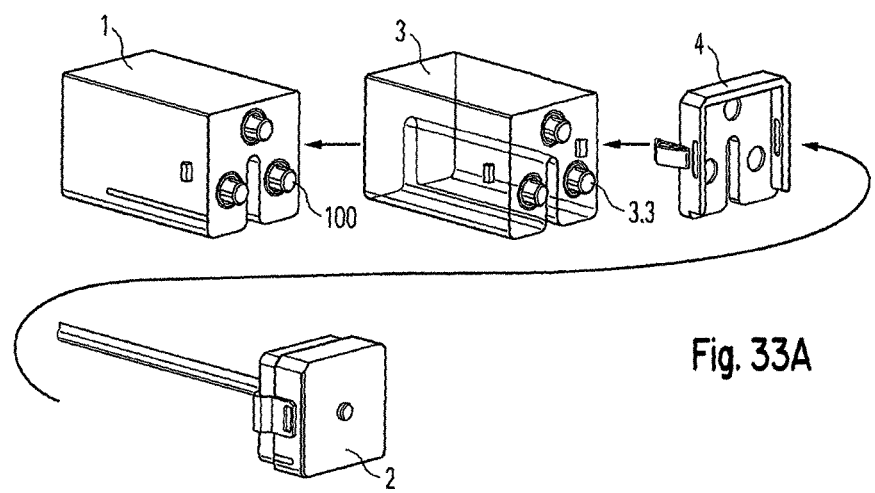
Figure 33B:
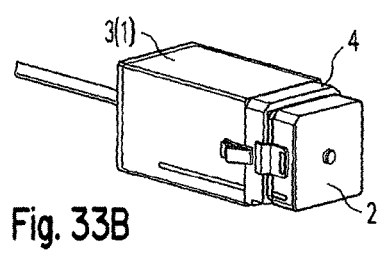
Figure 34:
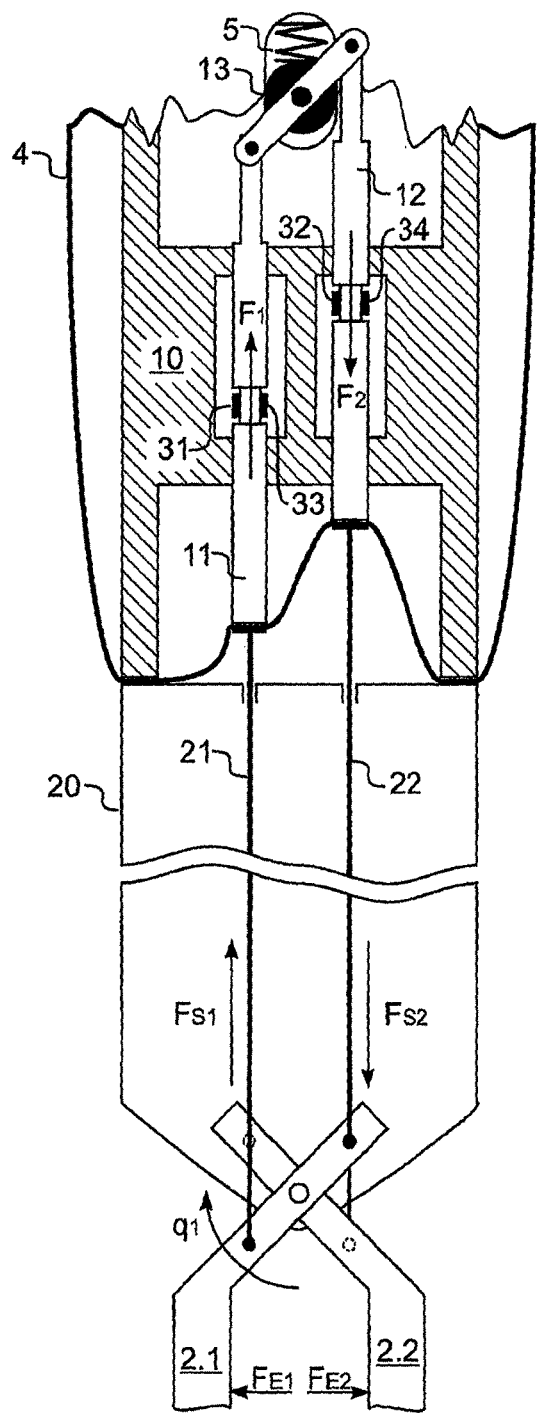
Figure 35:
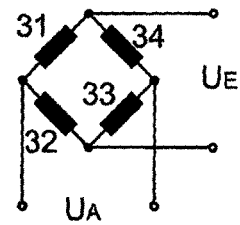
Figure 36:
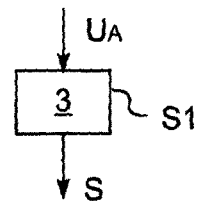
Figure 37:
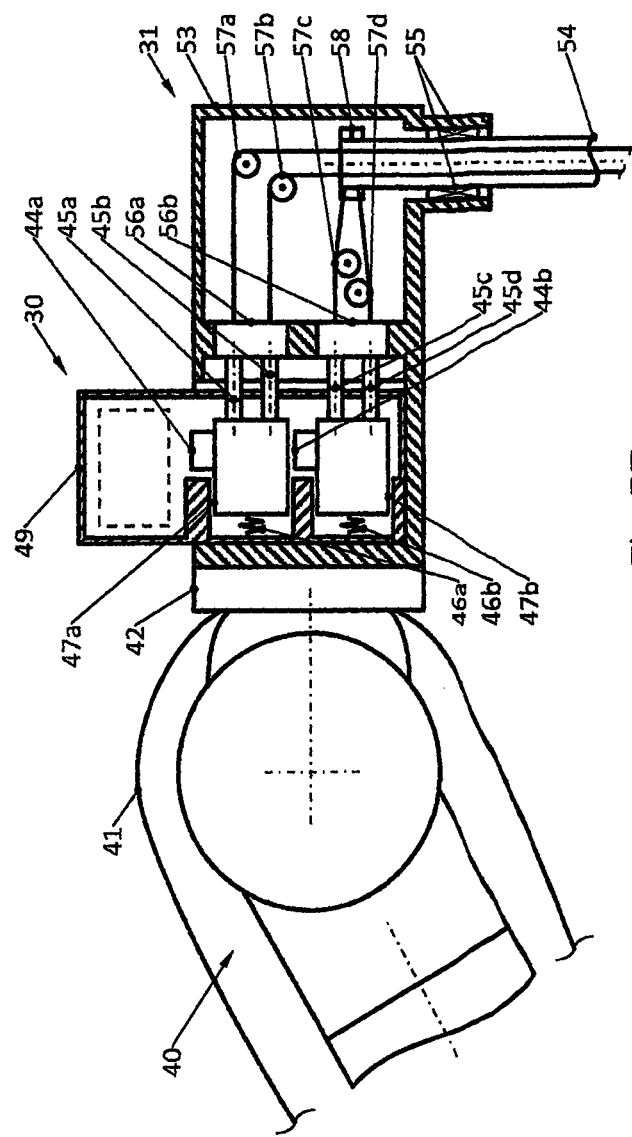
Figure 41:
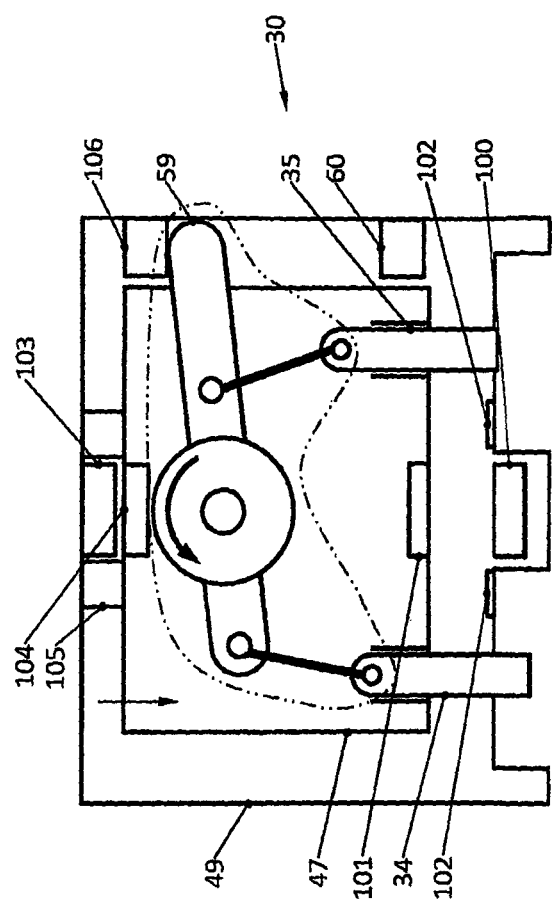
Figure 42A:
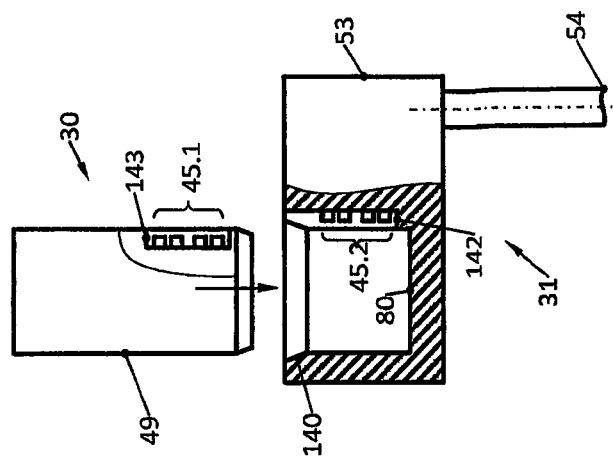
Figure 42B:
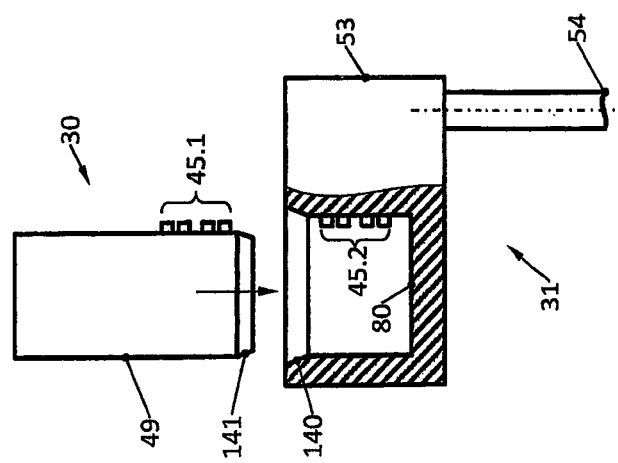
Figure 43A:
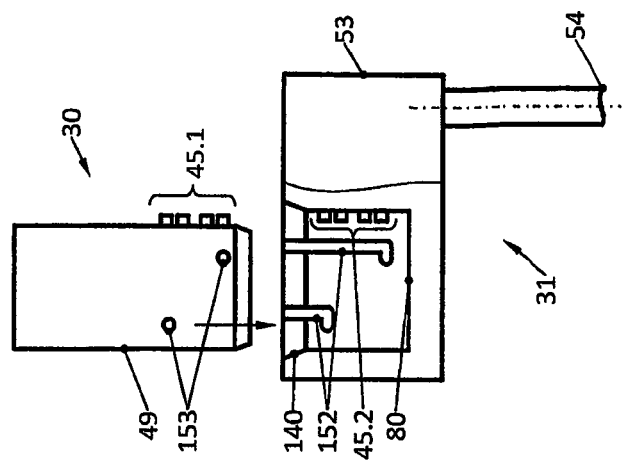
Figure 43B:
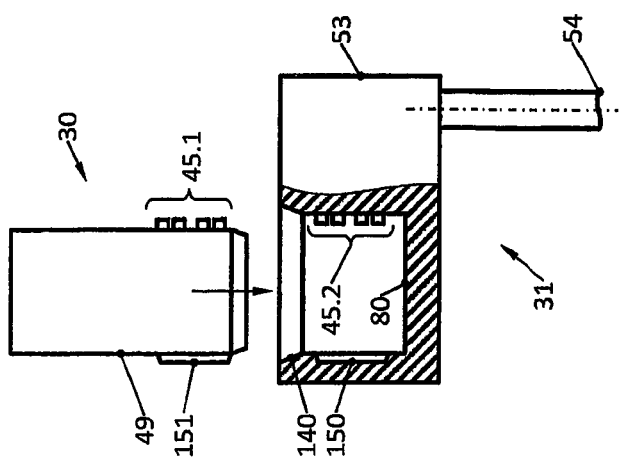
Figure 44B:
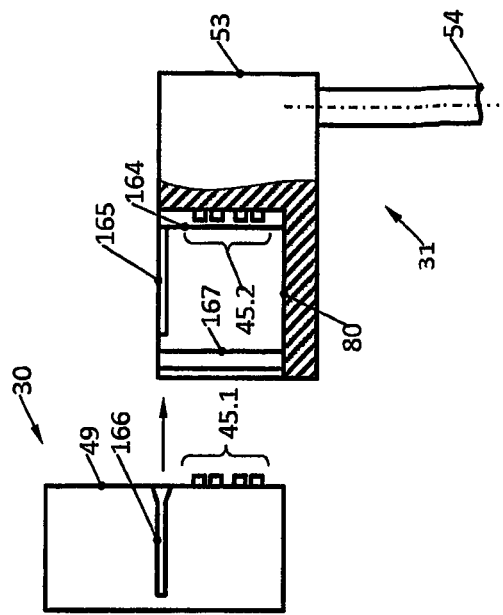
Figure 44A:
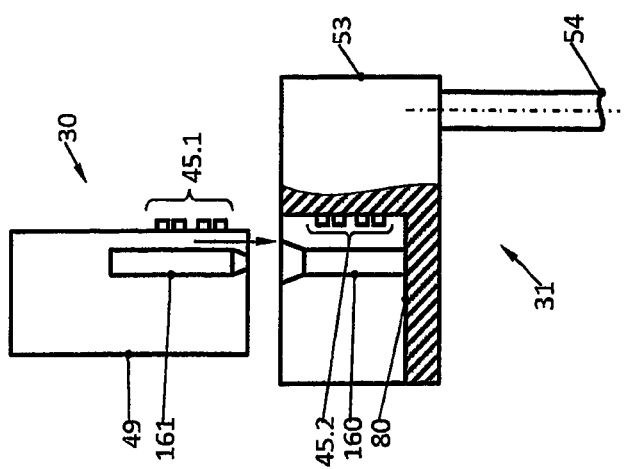
Figure 45B:
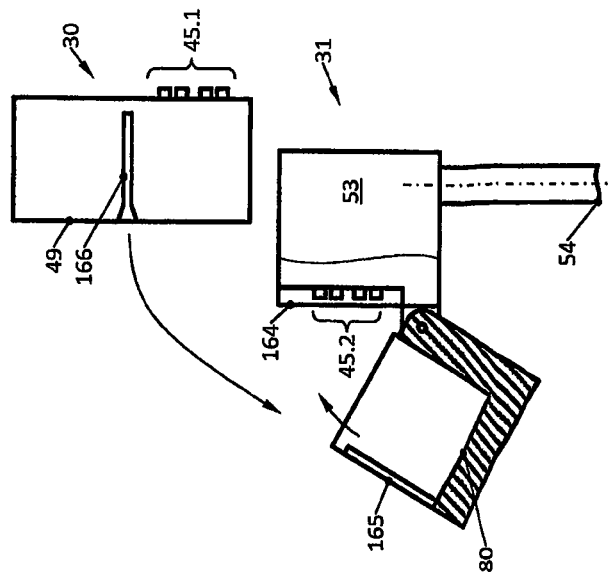
Figure 45A:
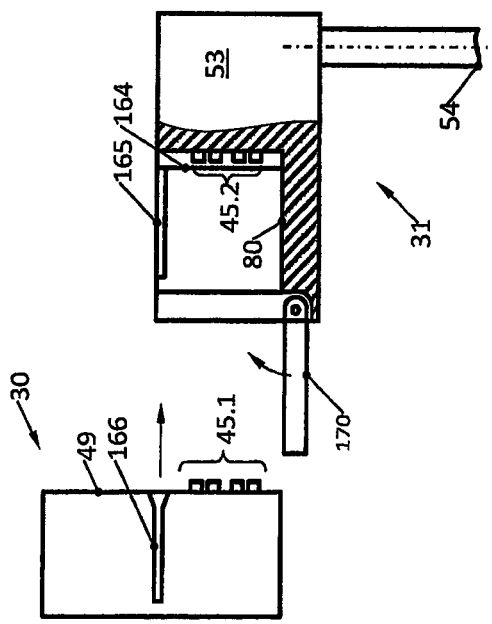
Figure 46A:
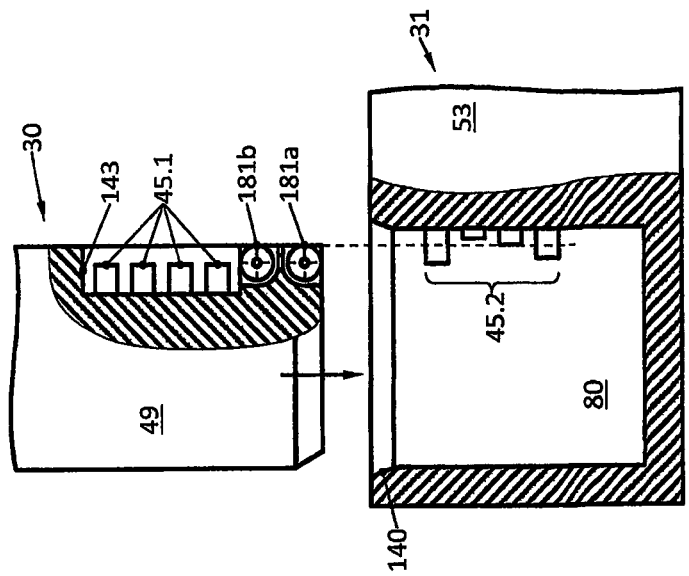
Figure 46B:
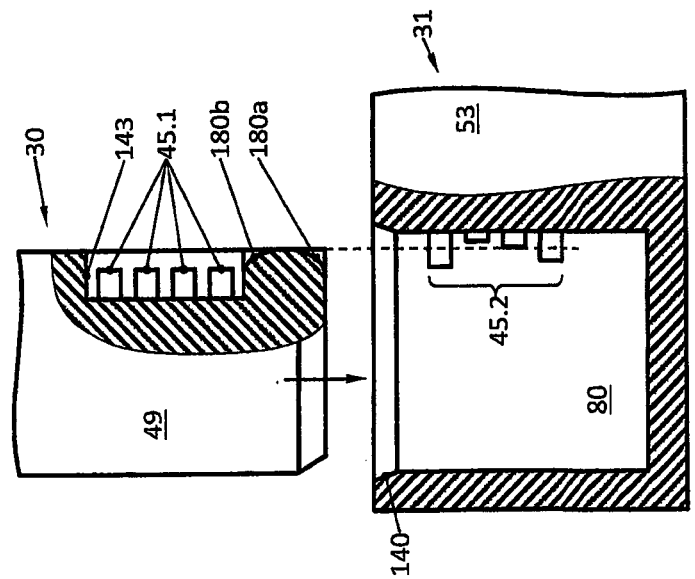
Figure 47:
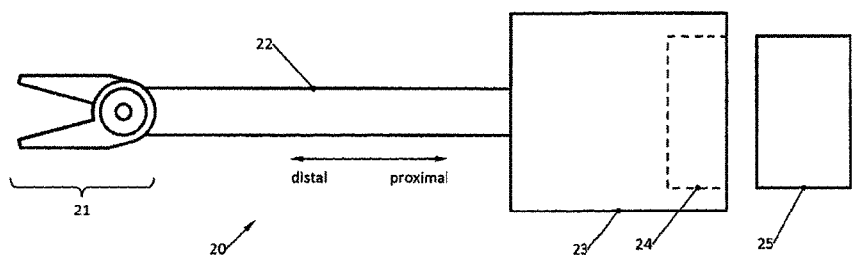
Figure 48A:
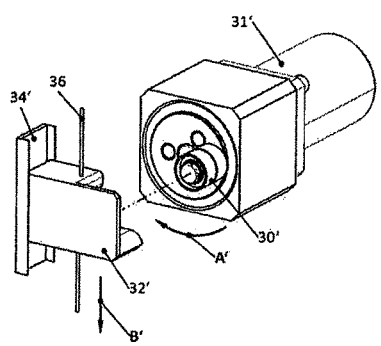
Figure 48B:
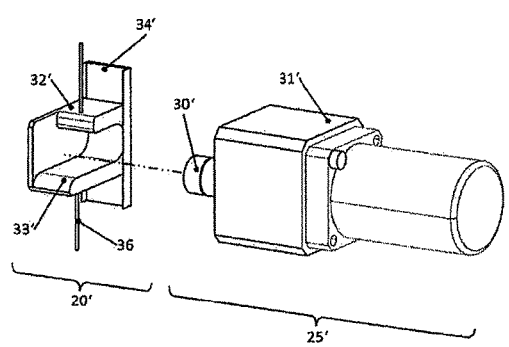
Figure 49A:
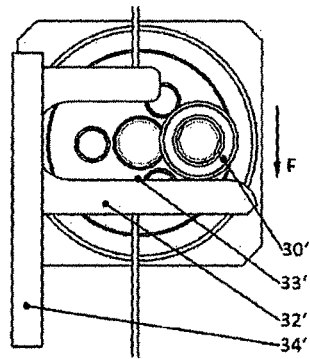
Figure 49B:
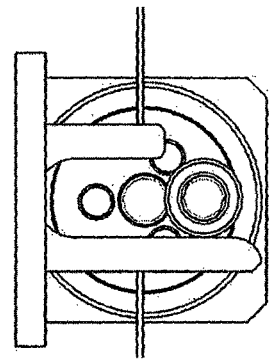
Figure 49C:
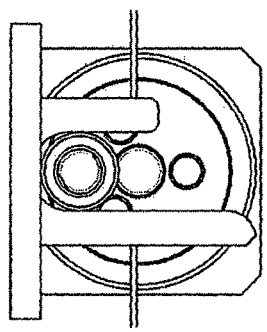
Figure 52:
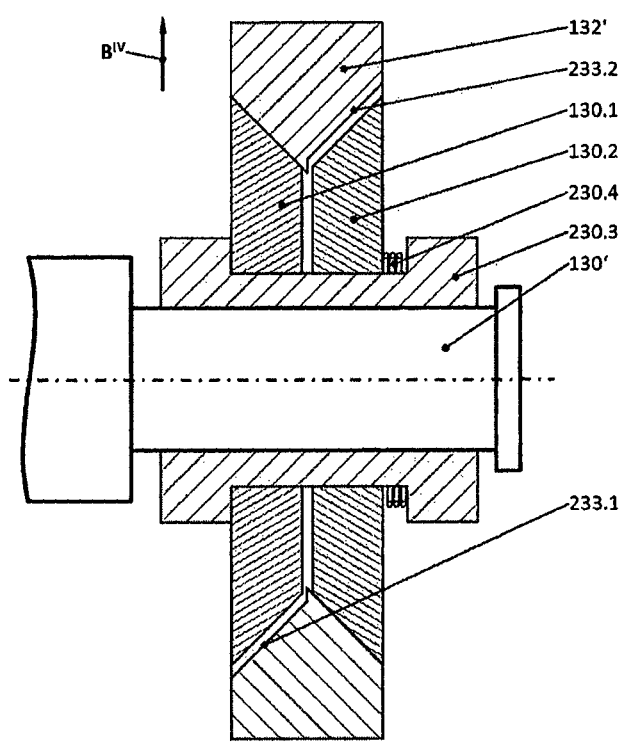
Figure 53A:
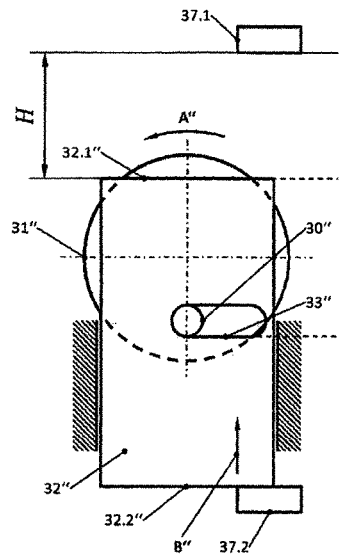
Figure 53B:
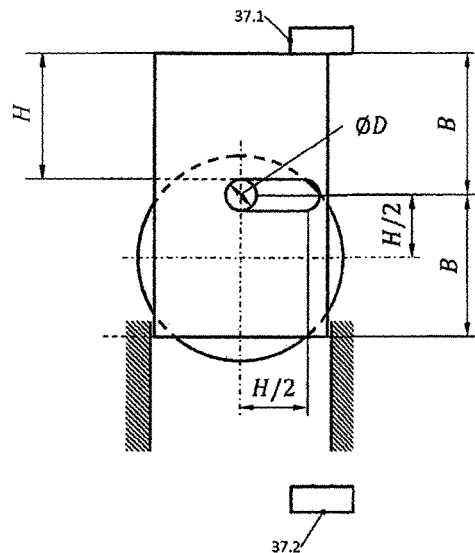
Figure 54:
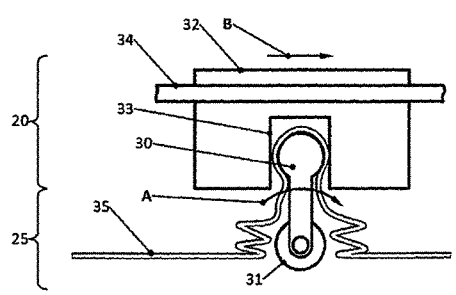
Figure 55D:
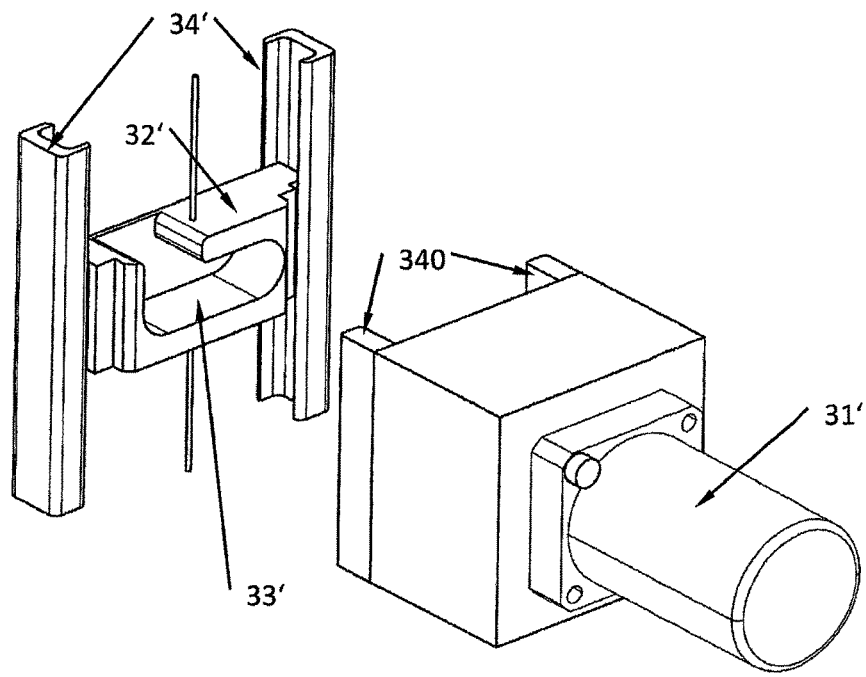
Figure 55E:
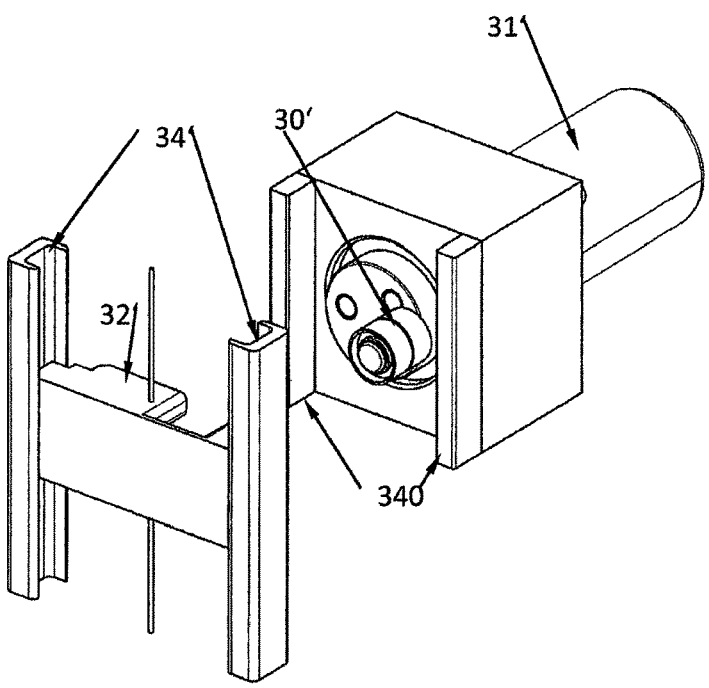

31A-31C: mechanical interfaces of instrument assemblies according to further embodiments of the present invention, with a sterile barrier, have a seal that can be displaced translationally without contact thereto;

FIGS. 32A-32B: a mechanical interface of an instrument assembly according to a further embodiment of the present invention, with a sterile barrier, which has an element extension that is releasably connected to an output drive element base or input drive element base;

FIGS. 33A-33B: an instrument assembly according to a further embodiment of the present invention, with an attachment element in the form of a sterile adapter 4;

FIG. 34: a part of a surgical instrument according to one embodiment of the present invention;

FIG. 35: a signal-based linking of metering means in a metering assembly for the surgical instrument in FIG. 34;

FIG. 36: a control means, or method, respectively, according to one embodiment of the present invention;

FIG. 37: a part of a robot-guided surgical instrument according to one embodiment of the present invention in a partial section;

FIG. 38: a drive module and an input drive link assembly coupled thereto, of the surgical instrument in FIG. 37;

FIG. 39: a drive module and an input drive link assembly coupled thereto, according to a further embodiment of the present invention depicted in FIG. 38;

FIG. 40A: a drive module with a retraction assembly according to a further embodiment of the present invention depicted in FIG. 38, in a state in which it is coupled to an input drive link assembly;

FIG. 40B: the retracted and locked down drive module in FIG. 40A;

FIG. 41: a drive module according to a further embodiment of the present invention depicted in FIG. 38;

FIG. 42A: a drive unit and an instrument shaft of a surgical instrument according to a further embodiment of the present invention in a partial section;

FIG. 42B: a drive unit and an instrument shaft of a surgical instrument according to a further embodiment of the present invention depicted in FIG. 42A;

FIG. 43A: a drive unit and an instrument shaft of a surgical instrument according to a further embodiment of the present invention depicted in FIG. 42A;

FIG. 43B: a drive unit and an instrument shaft of a surgical instrument according to a further embodiment of the present invention depicted in FIG. 42A;

FIG. 44A: a drive unit and an instrument shaft of a surgical instrument according to a further embodiment of the present invention depicted in FIG. 42A;

FIG. 44B: a drive unit and an instrument shaft of a surgical instrument according to a further embodiment of the present invention depicted in FIG. 42A;

FIG. 45A: a drive unit and an instrument shaft of a surgical instrument according to a further embodiment of the present invention depicted in FIG. 42A;

FIG. 45B: a drive unit and an instrument shaft of a surgical instrument according to a further embodiment of the present invention depicted in FIG. 42A;

FIG. 46A: a drive unit and an instrument shaft of a surgical instrument according to a further embodiment of the present invention depicted in FIG. 42A;

FIG. 46B: a drive unit and an instrument shaft of a surgical instrument according to a further embodiment of the present invention depicted in FIG. 42A;

FIG. 47: a surgical instrument according to one embodiment of the present invention;

FIGS. 48A-48B: an interface of the surgical instrument in FIG. 47, in a perspective view;

FIGS. 49A-49B: steps for coupling a guide element to a groove in the interface in FIGS. 48A-48B;

FIGS. 49C-49F: steps for actuating an input drive link by means of an output drive link of the surgical instrument in FIG. 47;

FIG. 50: an interface of a surgical instrument according to a further embodiment of the present invention, in a partial section;

FIGS. 51A, 51B: an interface of a surgical instrument according to a further embodiment of the present invention in a perspective view (FIG. 51A) and a partial section (FIG. 51B);

FIG. 52: an interface of a surgical instrument according to a further embodiment of the present invention in FIG. 51B in a corresponding manner;

FIGS. 53A, 53B: an interface of a surgical instrument according to a further embodiment of the present invention in various positions;

FIG. 54: an interface of a surgical instrument according to a further embodiment of the present invention; and FIGS. 55A-55E: an interface of a surgical instrument according to a further embodiment of the present invention in a view from above, in the direction of a displacement axis (FIGS. 55A-55C), or in a perspective view (FIGS. 55D-55E), wherein an output drive link and an input drive link are not coupled to one another (FIGS. 55A, 55B, 55D, 55E) or are coupled to one another (FIG. 55C).

DETAILED DESCRIPTION

Figure 1:
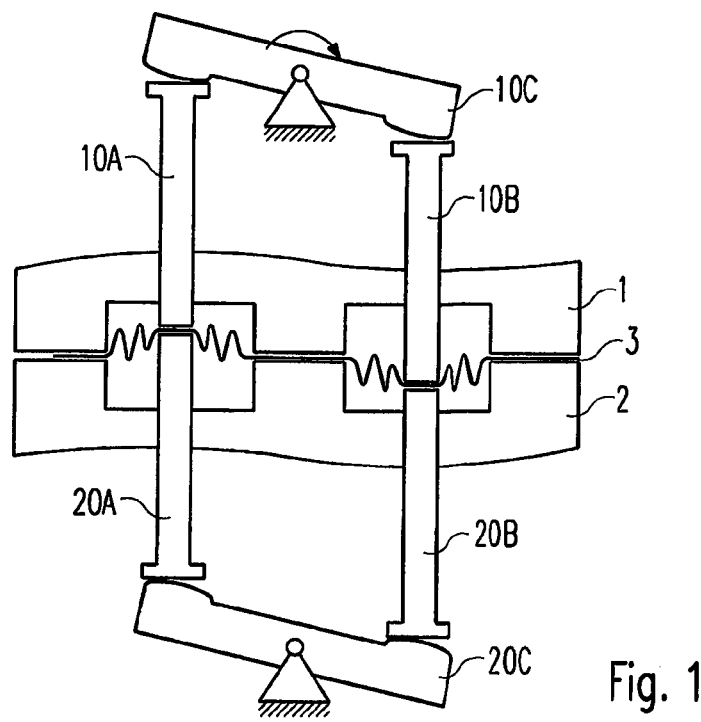
FIG. 1: a mechanical interface of an instrument assembly according to one embodiment of the present invention.

FIG. 1 shows a mechanical interface of an instrument assembly according to one embodiment of the present invention, having two output drive elements 10A, 10B of an output drive assembly running in opposite directions, and a modular motor drive unit 1. These are coupled to two input drive elements 20A or 20B, respectively, of an input drive assembly for an instrument shaft 2. A sterile barrier 3 encases the drive unit 1 and is disposed between this drive unit and the instrument shaft 2.

Output drive and input drive elements 10A, 10B, and 20A, 20B, respectively, are inserted in the drive unit 1, or the instrument shaft 2, respectively, such that they can be translationally displaced.

The output drive elements 10A, 10B are coupled to a coupling means designed as a rocker 10C, such that a rotational movement by the coupling means 10C, indicated by circular arrow in FIG. 1, is converted to a translational movement of the elements 10A, 10B. The coupling means 10C can be connected, for example, to an output drive shaft of an electric motor for the drive unit 1, or can be coupled via a gearing (not shown).

In a similar manner, the input drive elements 20A, 20B are coupled to a further coupling means designed as a rocker 20C, such that a translational movement of the elements 20A, 20B is converted to a rotational movement by the coupling means 20C. Pull cables or push rods of the instrument shaft 2, which are axially spaced apart from one another, can be attached to the coupling means 20C, for example, by means of which a degree of freedom of an end effector is actuated, such that, for example, a scissors is opened, or a scalpel is rotated (not shown). Likewise, the rotational movement of the coupling means 20C can be transferred, for example, via gearwheels, or—by means of a worm gearing—again converted into a translational movement.

Both output drive elements and input drive elements allocated thereto 10A, 20A, and 10B, 20B, respectively, between themselves, as well as the output drive elements 10A, 10B and the coupling means 10C, as well as the input drive elements 20A, 20B and the further coupling means 20C, are each coupled to one another by means of a one-sided linkage. One can see that only pressure forces can be transferred by the coupling means 10C to the output drive elements 10A, 10B, and by these to the input drive elements 20A, 20B, and by these, in turn, to the further coupling means 20C.

The output drive and input drive elements are designed as tappets in the embodiment, which are displaced along their longitudinal axes by means of a linear actuator or a joint kinematic. The sterile barrier 3 is located between the tappets. Because only pressure forces can be transferred with a pair of tappets, a closed kinematic loop is formed by the second pair of tappets. The second pair of tappets is moved in the opposite direction of that of the first pair, such that drive forces can be transferred in both directions. In general, therefore, in one embodiment of the invention, a parallelogram kinematic is provided in the mechanical interface.

The coupling of the instrument shaft to the drive unit has a simple design, and can, alternatively, occur along, or transverse to, the movement, or adjustment direction of the tappets 10A-20B. The tappets 10A, 10B for the drive unit 1 are covered by the sterile barrier. The instrument shaft 2 is joined to the drive unit 1 such that the tappets 10A, 20A, or 10B, 20B, respectively, are initially opposite one another, at a certain spacing. Subsequently the output drive-side is pushed to the input drive-side. The angular position of the tilt lever, or rocker 10C, 20C, is arbitrary thereby, because the positions of both sides align during the coupling process.

Figure 2:
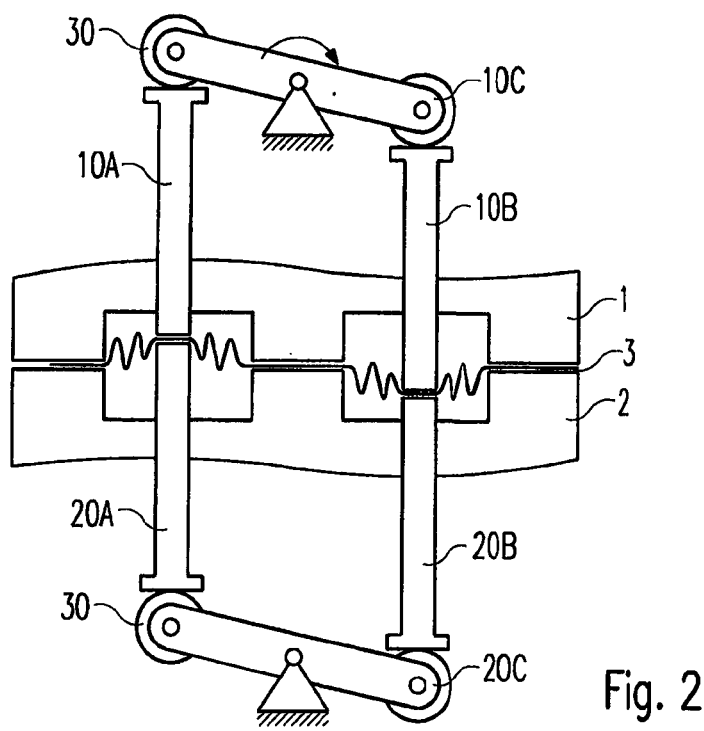
FIGS. 2 to 6: mechanical interfaces of instrument assemblies according to further embodiments of the present invention.

FIG. 2 shows a mechanical interface for an instrument assembly according to a further embodiment of the present invention. Features corresponding to those in the embodiment explained above are indicated with identical reference symbols, such that in the following, only the differences shall be addressed, and otherwise, reference is made to the overall description.

In the embodiment in FIG. 1, sliding contact occurs between the coupling means 10C, 20C and the tappets 10A, 10B, or 20A, 20B, respectively, wherein the frictional forces are a function of, among others, the lever position and the contact surfaces, in particular their geometry and surfaces. Therefore, in one embodiment of the present invention, as it is depicted by way of example in FIG. 2, a roller 30 is disposed in at least a one-sided contact with a coupling means (in FIG. 2, by way of example: 10C, 20C) and the output drive and input drive elements (in FIG. 2, by way of example: 10A, 10B, or 20A, 20B, respectively), by means of which the friction can be reduced.

Figure 3:
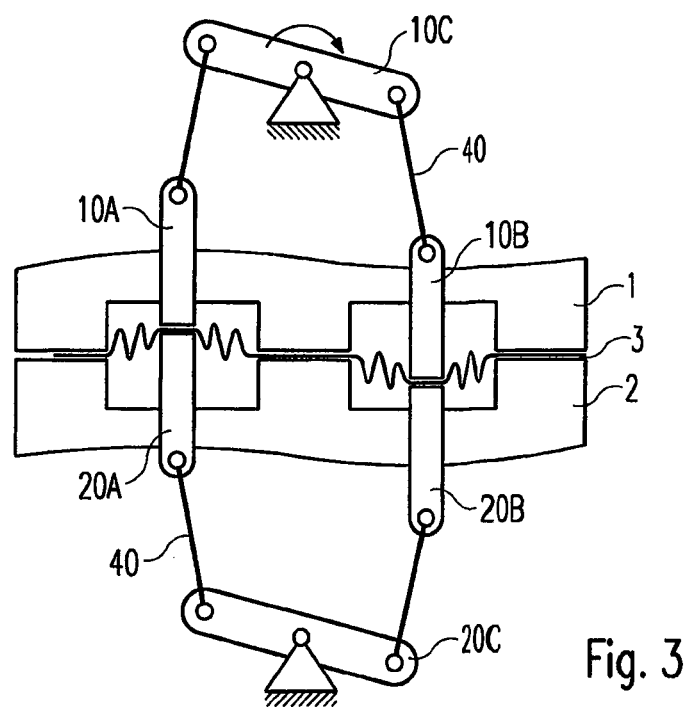

FIG. 3 shows a mechanical interface of an instrument assembly according to a further embodiment of the present invention. Features corresponding to those in the other embodiment are indicated by identical reference symbols, such that only the differences shall be addressed below, and otherwise, reference is made to the overall description.

In the embodiments in FIGS. 1 and 2, the output drive elements 10A, 10B and the coupling means 10C, as well as the input drive elements 20A, 20B and the further coupling means 20C are each connected to one another by means of a one-sided linkage having sliding (FIG. 1) or rolling (FIG. 2) contact, respectively. In one embodiment, which is shown by way of example in FIG. 3, at least one output drive element (in FIG. 3, by way of example: 10A, 10B) and one coupling means (in FIG. 3, by way of example: 10C), and/or at least one input drive element (in FIG. 3, by way of example: 20A, 20B) and one (further) coupling means (in FIG. 3, by way of example: 20C), on the contrary, are coupled to one another by at least one coupling rod (in FIG. 3, by way of example: 40), which is connected in an articulated manner to the coupling means, or element, respectively.

Figure 4:
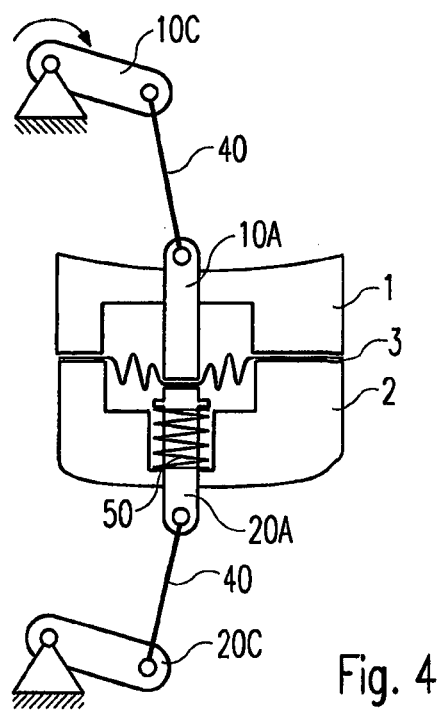

FIG. 4 shows a mechanical interface of an instrument assembly according to a further embodiment of the present invention. Features corresponding to those in the other embodiments are indicated with identical reference symbols, such that only the differences shall be addressed below, and otherwise, reference is made to the overall description.

In this embodiment, only one pair of tappets 10A, 20A for transferring forces is provided for the actuation of a degree of freedom. Instead of a further pair of output and input drive elements, the input drive element 20A is pre-tensioned against its adjustment direction by a spring 50. This returns the pair of tappets 10A, 20A against the adjustment direction, when an actuating force in an adjustment direction is removed, or, respectively, in the case of an actuating movement of the output drive element counter to this adjustment direction.

Figure 5:
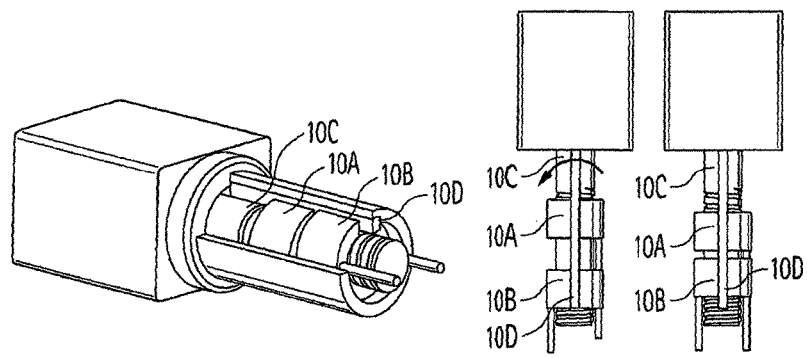

FIG. 5 shows a mechanical interface of an instrument assembly according to a further embodiment of the present invention. Features corresponding to those in the other embodiments are indicated with identical reference symbols, such that only the differences shall be addressed below, and otherwise, reference is made to the overall description.

In one embodiment, which is shown by way of example in FIG. 5, a least one coupling, in the manner of a spindle drive having sliding sleeves moved in opposite directions, is formed between an output drive element (in FIG. 5, by way of example: 10A, 10B) and a coupling means (in FIG. 5, by way of example: 10C). The coupling means, preferably designed as a winding spindle (in FIG. 5, by way of example: 10C) has, in one embodiment, one section with right-handed threads and one section with left-handed threads, on which, in each case, an output drive element sits, designed as a spindle nut (in FIG. 5, by way of example: 10A or 10B). By rotating the threaded spindle 10C, the spindle nuts 10A, 10B are moved in opposite directions. The nuts can be secured against turning by means of a guide rail 10D fixed in place in relation to the drive unit, for example.

For purposes of clarification, a perspective partial section of the interface is shown in the left side of FIG. 5, side views with different settings of the output drive elements 10A, 10B are shown in the middle and at the right, respectively.

Figure 6:
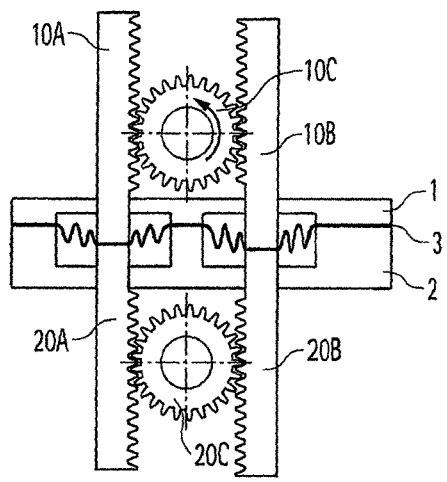

FIG. 6 shows a mechanical interface of an instrument assembly according to a further embodiment of the present invention. Features corresponding to those in the other embodiments are indicated by identical reference symbols, such that only the differences shall be addressed below, and otherwise, reference is made to the overall description.

In one embodiment, which is shown by way of example in FIG. 6, at least one output element (in FIG. 6, by way of example: 10A, 10B) and one coupling means (in FIG. 6, by way of example: 10C) and/or at least one input drive element (in FIG. 6, by way of example: 20A, 20B) and one (further) coupling means (in FIG. 6, by way of example: 20C) are coupled by a rack and pinion gearing. For this, in a further development, the coupling means (in FIG. 6, by way of example: 10C, 20C) are designed as pinions, with which the output drive elements (in FIG. 6, by way of example: 10A, 10B), or the input drive elements (in FIG. 6, by way of example: 20A, 20B) designed as racks, mesh, in each case in opposite directions, thus converting a rotational movement into a translational movement. Because they are disposed on opposite sides of the rack, they move in opposing directions. When, in an advantageous further development, the input drive elements and/or the output drive elements are pre-tensioned against their adjustment direction, or toward one another, respectively, backlash in the tooth engagements 10A-10C, 10B-10C, 20A-20C, or 20B-20C, respectively, can be reduced or eliminated thereby in an advantageous manner.

Figures 7A, 7B, 7C, 7D, 7E:
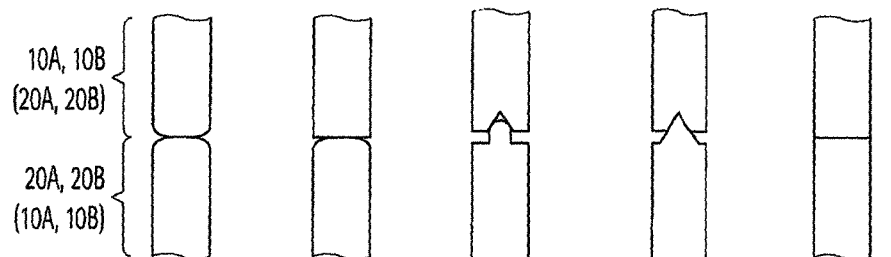
FIGS. 7A-7E: various embodiments of the front surfaces facing one another of the output drive elements and the input drive elements of the mechanical interfaces in FIGS. 1 to 6.

FIGS. 7A-7E shows various embodiments of the front surfaces of the output drive elements and the input drive elements 10A, 10B, or 20A, 20B, respectively, facing one another, in the embodiments in FIGS. 1 to 6, which are designed such that they are flat or convex and/or have a projection for engaging in a cut-out in the other front surface: FIG. 7A shows two flat front surfaces, or contact surfaces, which form a (one-sided linked) surface contact thereby, FIG. 7B shows a convex front surface and a flat front surface, which form a point contact, FIG. 7C shows a spherical projection, which engages in a conical hole or cut-out, and forms an annular contact, FIG. 7D shows a conical projection, which engages in a conical hole or cut-out, and forms a surface contact, and FIG. 7E shows two convex front surfaces, or contact surfaces, which form a point contact.

In order to ensure a transference precision and rigidity to the greatest possible extent, deviations in the position and orientation of the contact surfaces should be avoided. Possible causes of such deviations are production and assembly tolerances, as well as deviations in the positioning of the instrument in relation to the drive unit by the user. For this reason, in one embodiment of the present invention, at least one one-sided linkage has a point contact between the output drive element and the input drive element.

FIGS. 8A-8C, 9, 10 show compensation means for tolerance compensation. FIG. 8 shows a compensation for position and orientation deviations of the tappet-contact surfaces by means of flexibilities imposed thereon in a targeted manner. In one embodiment, which is indicated by way of example in FIG. 8A, a flexibility is formed by means of a flexible design of an output drive element and/or an input drive element (in FIG. 8A, by way of example: 10A or 20A). Additionally or alternatively, a flexibility can be formed by means of an elastic deformation of the sterile barrier, as is indicated by way of example in FIG. 8B. The sterile barrier is preferably produced, entirely or in part, from an elastomer.

Figures 8A, 8B:
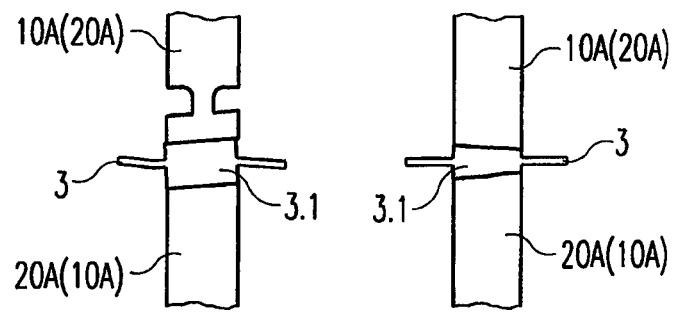
FIGS. 8A-8C, 9, 10: compensation means for tolerance compensation.
Figure 8C:
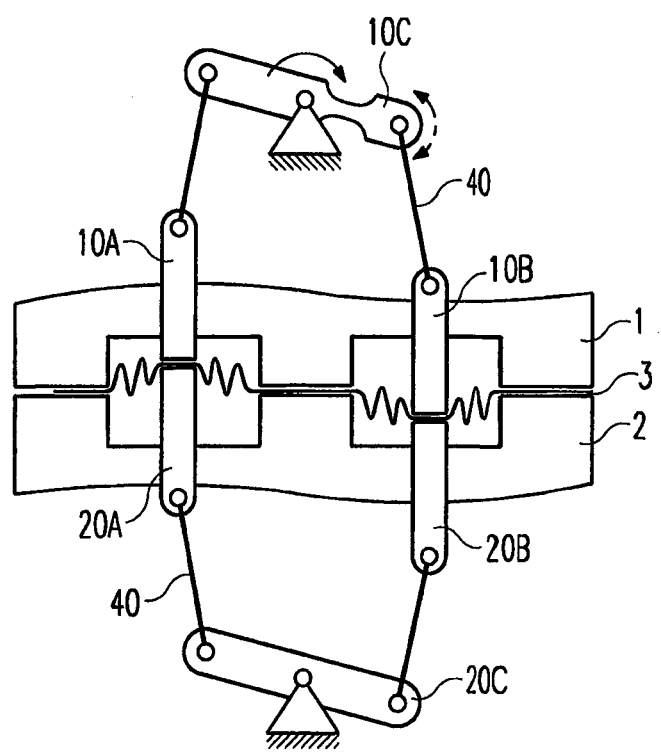

The flexible design of an output drive element and/or an input drive element, as is shown in FIGS. 8A-8C, can be advantageous with regard, in particular, to the transference behavior. In general, a flexibility in an embodiment of the present invention can have a progressive spring characteristic, in order to thus be able to compensate for smaller tolerances, and at the same time, to ensure a relatively rigid transference during larger actuations.

Additionally or alternatively, a flexibility can be provided in a coupling means, as is shown by way of example in FIG. 8C. Because of the closed kinematic chain, this concerns, in principle, a static over-determined system. In order to compensate for production and assembly tolerances in the kinematic chain, and to obtain a lack of play, length differences between the pair of tappets are compensated for by a flexible design of a coupling means.

Figure 9:
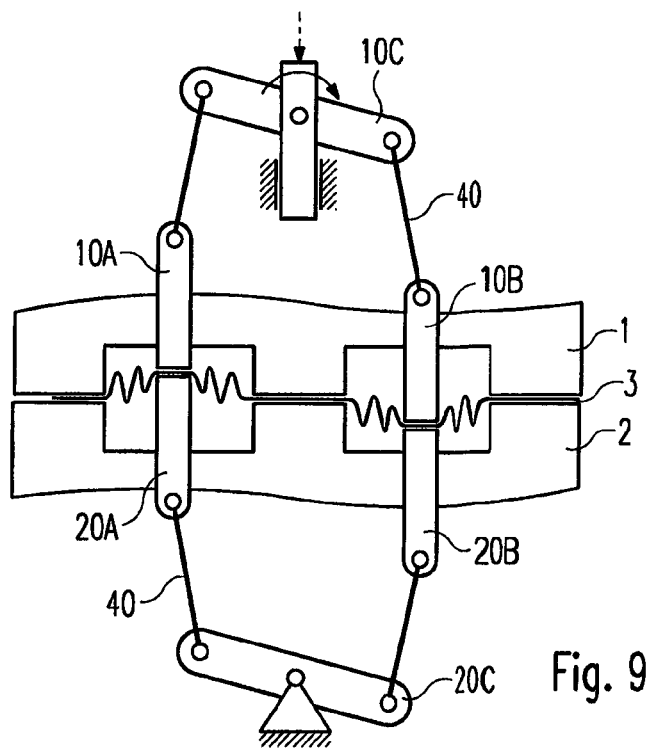

In one embodiment, which is indicated by way of example in FIG. 9, a compensating means for tolerance compensation has a bearing that can be displaced in an adjustment direction (vertical in FIG. 9) or a bearing axis of a coupling means that can be displaced in an adjustment direction (in FIG. 9, by way of example: 10C). For this purpose, in one embodiment, this is rotatably mounted in a slide, which is disposed inside the drive unit such that it can be displaced therein. This thrust bearing enables a displacement in the direction of the tappet movement. A force is applied in this direction, for example, by means of a spring or by means of a static adjustment, which pre-tensions the pair of tappets against one another in the interface (in FIG. 9, indicated by the dotted force arrow).

Figure 10:
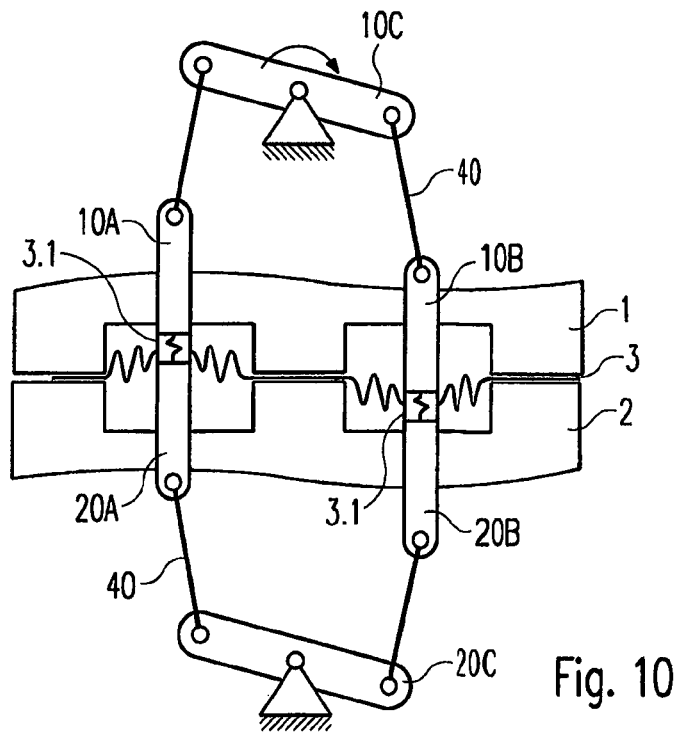

FIG. 10 shows a compensation for length tolerances between the pair of tappets by means of flexibilities in the sterile barrier, as has already been explained above in reference to FIG. 8B. In one embodiment of the present invention, which is indicated by way of example in FIG. 10, a flexible compensation element 3.1 is integrated in the sterile barrier. By compressing this element, a pre-tensioning is built up in the kinematic loop, and at the same time, length differences are compensated for by means of different compressions. In particular, in order to avoid too much flexibility, which could be detrimental with respect to the regulating behavior, the compensation element 3.1 exhibits a progressive spring behavior in a further development. This can be obtained, in particular, by means of an appropriate selection of the material and/or the geometric design of the sterile barrier.

Figure 11:
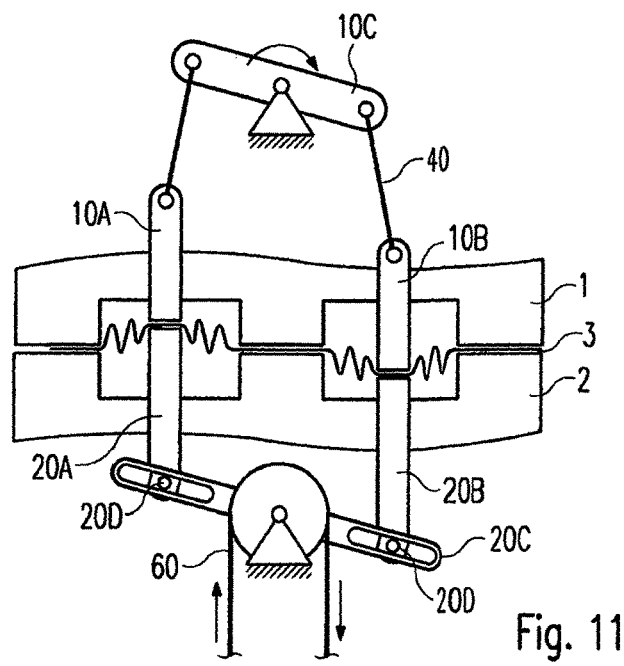

FIGS. 11 to 15 show, in particular, various advantageous couplings of an instrument shaft-side drive train on an inventive mechanical interface, as is described above in reference to FIGS. 1 to 10, but in the following in reference to the other figures. FIG. 11 shows a coupling of a pull cable 60 to the input drive element thereby. In order to actuate a degree of freedom of the instrument shaft, in particular an end effector (not depicted), in both, or opposite, directions, a kinematic loop is formed in the instrument shaft with the rotatably mounted rocker 20C between the two tappets 20A, 20B. In the embodiment shown here, the tappets are each coupled to the rocker with a rotational thrust bearing 20D. A cable pulley is permanently connected to the rocker, around which the pull cable is wound. In a further development a form-locking and/or material bonded connection between the pulley and the pull cable is also possible. With an appropriate selection of the cable pulley diameter, optionally, an adjustment of the interface stroke to the necessary cable stroke can also be carried out. In addition to the depicted cylindrical cross-section of the cable pulley, other, in particular elliptical, cross-sections are also possible.

Figure 12:
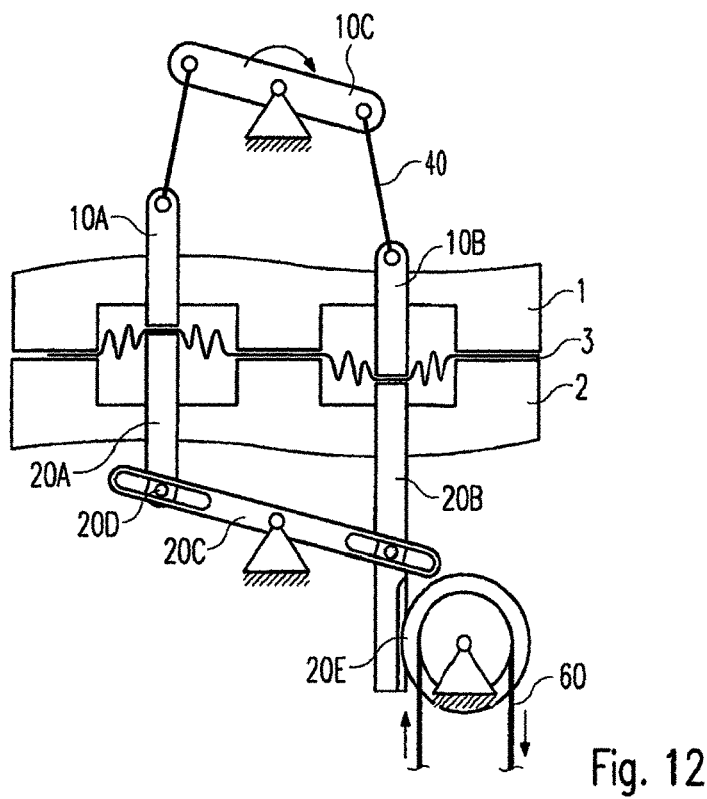
Figure 13:
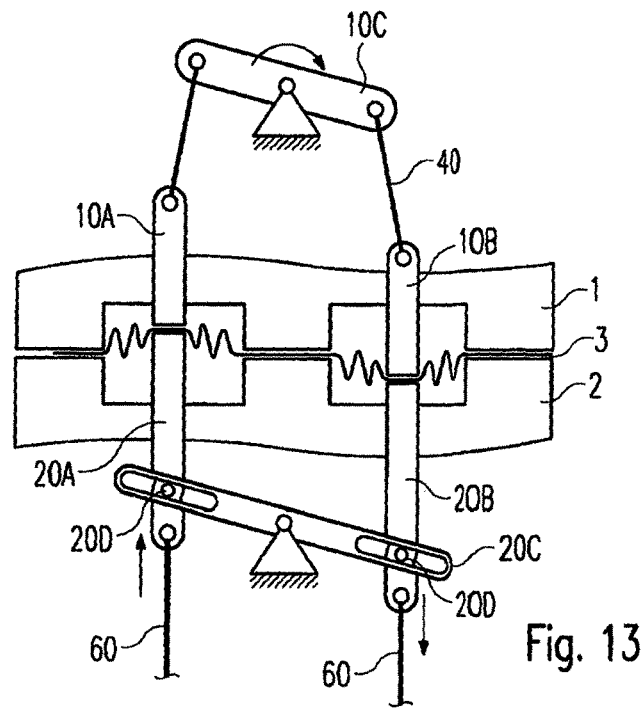

FIG. 12 shows a coupling of an instrument-side pull cable 60 on the mechanical interface according to a further embodiment. In this case, the cable pulley, which forms an element of a coupling means as set forth in the present invention, is also provided with a gear toothing 20E, which meshes with a toothed section of an instrument-side tappet (in FIG. 12, by way of example: 20B). The additional gear ratio of this gearwheel stage enables, advantageously, an even better adjustment of the tappet stroke to the cable stroke.

Figure 14:
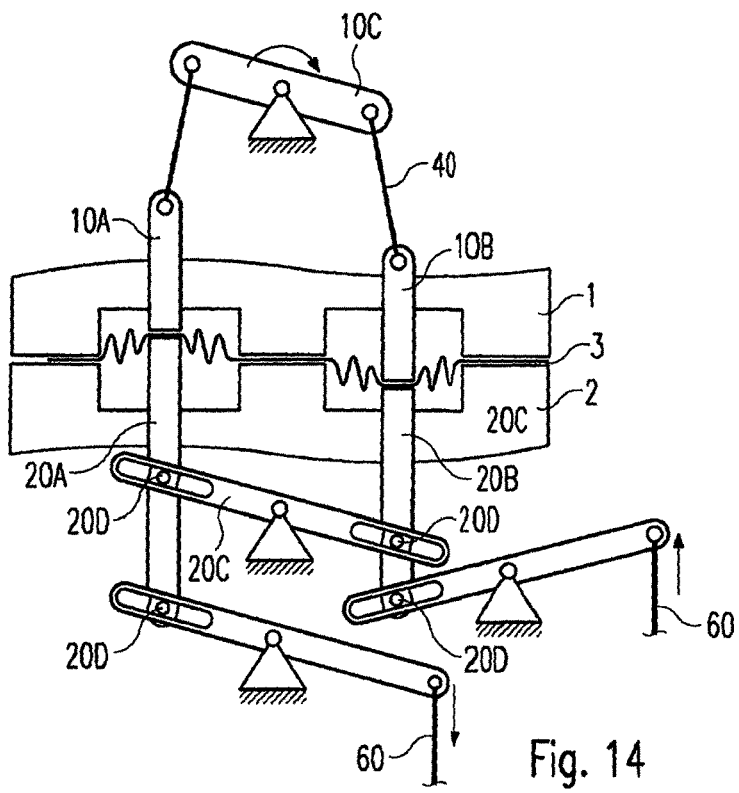

In both embodiments in FIGS. 11, 12, the pull cable 60 is continuous. In an alternative embodiment of the present invention, which is indicated by way of example in FIGS. 13, 14 and 15, a degree of freedom can also be actuated by a pull cable with distinct ends (in FIG. 13, by way of example: 60) or by push rods (not shown), the ends of which can be coupled to input drive elements (in FIG. 13, by way of example: 20A, 20B), or a coupling means coupled thereto. In one embodiment of the present invention, as is indicated by way of example in FIGS. 14, 15, the ends of the pull cable 60 are coupled via additional cable rockers thereby, to the mechanical interface, or its input drive elements 20A, 20B, respectively. The cable stroke can advantageously be adjusted via the ratios of the lever arms of each rocker. In order to avoid a change to the necessary cable length, the lever ratios of both cable rockers can be the same. In FIGS. 14, 15 the two bearing points of the cable rockers are depicted offset to one another, for better clarity. In one embodiment, these bearings for the cable rockers can be coaxial to one another. In the embodiment in FIG. 14, the closed kinematic loop between the output drive and input drive elements is formed by a further instrument-side rocker, which is coupled, in each case, to the instrument-side tappets 20A, 20B via a rotational thrust bearing 20D. In the embodiment in FIG. 15, this additional rocker is omitted, and instead, the pre-tensioning of the interface is built up via the pull cable, by means of which a closed kinematic loop already exists. In particular, in this manner, according to one embodiment of the present invention, a pre-tensioning of the mechanical interface can also be used in general for pre-tensioning an instrument shaft-side pull cable, by means of which the complexity of the instrument-side drive train is reduced. At this point, it should be expressly noted that in the embodiments shown here, the allocation of output drive and input drive elements is purely exemplary, and in particular, assemblies or features of an output drive element in one embodiment can also be combined with assemblies or features of an input drive element of another embodiment. Thus, for example in the embodiment in FIG. 14, instead of the input drive-side rotational thrust bearing 20D, analogous to the output drive side, an assembly, or coupling, respectively, with coupling rods (cf. output drive-side coupling rod 40 in FIG. 14) is also conceivable.

FIG. 16 shows a mechanical interface of the instrument assembly according to a further embodiment of the present invention. Features corresponding to those in the other embodiments are indicated with identical reference symbols, such that only the differences shall be addressed below, and otherwise, reference is made to the overall description. In this embodiment, the interface has an output drive element in the form of a pin 100 and an input drive element having a cut-out 200, wherein the pin can be radially expanded in an elastic manner in the cut-out by a clamping means. This embodiment is suited for transferring tractive and pressure forces. In the following a translational actuation or adjustment of the mechanical interface shall be explained in an exemplary manner, although the mechanical interface can also be used for transferring rotational or superimposed translational and rotational movements.

The input drive pin 100 is guided and actuated in the drive unit 1 such that its position can be adjusted in a translational manner, and inserted in an instrument shaft-side cut-out in the form of a coupling socket 200. The thin-walled sterile barrier 3 is disposed between the drive unit and the instrument shaft.

The connecting of the input drive pin 100 and the coupling socket 200 can be force-locking or form-locking, and can occur in relation to, or independently of, the instrument drive. Advantageously, components having a greater complexity and smaller tolerances can be disposed in the drive unit, such that these interfaces are also advantageous, in particular, for less expensive disposable instrument shafts. The positioning and attachment of the instrument shaft in relation to the drive unit occur in a further development by means a separate functional unit, as described below. The bearing for the coupling element is preferably selected such that, for this reason, high demands on the shape and bearing tolerances are avoided, and the connecting of output drive elements and input drive elements occurs, at least substantially, without difficulty. The input drive pin is inserted, for this reason, in a further development, in the drive unit with a pentavalent thrust bearing, i.e. only displacements along the longitudinal axis are possible. The positioning and orientation of the coupling socket in the instrument shaft exhibits radial play, i.e. the coupling socket is not distinctly guided in the radial direction. As long as the instrument shaft is not coupled to the drive unit, the radial bearing ensures that the coupling sleeve is pre-positioned with sufficient precision, and cannot be released during manipulation and cleaning thereof. Once the instrument shaft is coupled to the drive unit, this bearing no longer serves a function. At that point, the thrust bearing of the input drive pin also acts as the bearing for the instrument shaft-side input drive element. In this manner, a connection is advantageously obtained without difficulties, without placing a load on the two bearings. The bearing for the coupling socket in the instrument shaft has two stops in a further development, in the axial, or adjustment, direction. Thus, the necessary working stroke can be individually determined for each instrument shaft, and the drive unit can be used for different instrument shafts.

A radial orientation of the coupling socket 200 in relation to the input drive pin 100 occurs automatically as a result of the geometric design of the coupling element. Thus, only a joining movement toward the input drive pin is necessary. As a result, instrument shaft replacement during a surgical operation is advantageously facilitated, and can be executed quickly.

Various advantageous embodiments of input drive pins and coupling sockets are depicted in FIGS. 17A-17D, 18A-18D, in particular a flat (FIG. 17D), conical (FIG. 17C), spherical (FIG. 17B) and an elliptical (FIG. 17A) front surface of the input drive pin, can each be combined with different insertion geometries of the instrument shaft-side coupling socket, in particular a cylindrical (FIG. 18D) blind hole, in particular with one or more steps (FIG. 18C), a chamfering (FIG. 18B) or rounding (FIG. 18A).

Figures 19A, 19B, 19C, 19D:
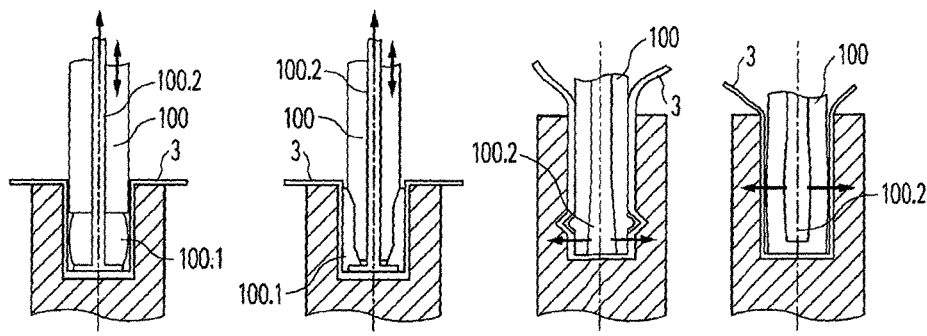

FIGS. 19A-19D show various couplings of the pin 100 and cut-out 200: in one embodiment, indicated by way of example in FIGS. 19A, 19B, and 19D, the pin and cut-out are coupled in a friction-locking manner by an elastic expansion of an input drive pin, designed in particular as a single- (FIG. 19D) or multi-piece (FIGS. 19A, 19B) pin, which can have an elastic body (in FIGS. 19A, 19B, by way of example: 100.1), the diameter of which is increased by an elastic deformation by means of a clamping means (in FIGS. 19A, 19B, 19C: 100.2). In one embodiment, indicated by way of example in FIG. 19C, the pins and cut-outs are coupled, additionally or exclusively, in a form-locking manner, through an elastic expansion of a single- or multi-piece input drive pin. In one embodiment, depicted in FIG. 19C by way of example, in combination with the form-locking, a clamping means (in FIG. 19C, by way of example: 100.2) has a conical external shape, and can be axially adjusted in the pin 100, in order to expand the pin radially from the inside. In the embodiment in FIGS. 19A, 19B, the clamping means 100.2 has a flange instead, for radially expanding the elastic pin by means of axial compression. In the embodiment in FIG. 19D, the clamping means 100.2 is designed as a hydraulic or pneumatic element, and the pin is radially expanded from the inside by pressurization thereof.

A sterile protective casing 3 is disposed between the pin and the cut-out, and enables the form-locking or friction-locking described above, due to its elasticity. As has been explained elsewhere, with this embodiment, a movement of the (non-sterile) drive unit on a (sterile) instrument shaft does not pass through a hole in the sterile barrier, but rather, is transferred via the sealed sterile barrier, facilitating the sterile manipulation thereof.

The clamping movement, or the clamping means (in FIGS. 19A-19D, by way of example: 100.2) can be actuated in relation to the instrument drive, or independently thereof.

Figures 20A, 20B:
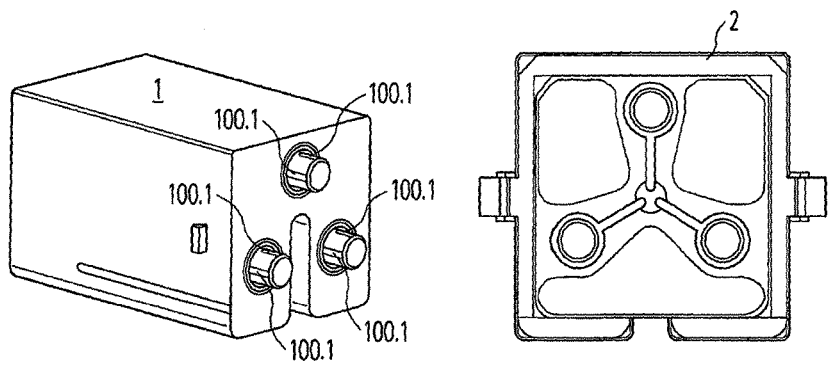
FIGS. 20A-20B: an instrument assembly according to a further embodiment of the present invention.
Figure 21:
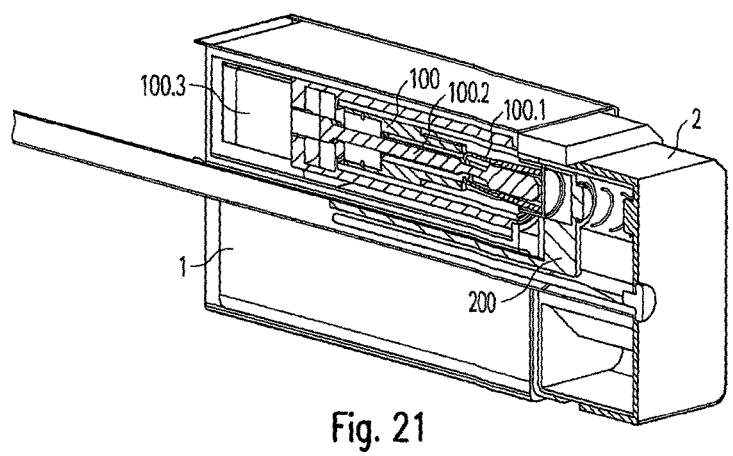
FIG. 21: an instrument assembly according to a further embodiment of the present invention.

FIG. 20A shows, by way of example, a drive unit 1 with three output drive elements in the form of pins, FIG. 20B shows an instrument shaft 2 that can be coupled thereto, having three input drive elements, which exhibit corresponding cut-outs. In one embodiment, a pin in an output drive or input drive element can be radially expandable in a non-elastic manner, and for this purpose, can exhibit one or more radially displaceably guided, preferably lamellar, separate bodies (in FIG. 20A, by way of example: 100.1), as is depicted by way of example in FIG. 20A.

FIGS. 21, 22, 23A-23C show cuts through a drive unit 1 and an instrument shaft 2 coupled thereto, having a (crank) pin interface according to a further embodiment of the present invention. Features corresponding to those in the other embodiments are indicated with identical reference symbols, such that only the differences shall be addressed below, and otherwise, reference is made to the overall description.

In particular, a clamping means drive in the form of an electric motor 100.3 and a threaded spindle 100.2 are indicated schematically, such as a cylindrical screw drive, a clamping means, a crank pin 100, and an instrument shaft-side coupling socket with a hole 200, for example. The threaded spindle 100.2, a ball or roller screw drive for example, is powered by an electric motor 100.3 in a path-controlled manner. The threaded spindle is mounted in the drive unit 1 by means of a spindle bearing. A spindle nut meshing with the threaded spindle 100.2 is non-rotatably connected to the crank pin 100. The crank pin is inserted, on its part, in a thrust bearing 100.5, which allows a translation only in the axial direction, and absorbs all radial forces and torques. For the friction-locking or form-locking (cf. FIGS. 19A-19D, in particular), the pin 100 has numerous separate bodies in the form of lamellar tension levers 100.1, which are uniformly distributed on the circumference of the crank pin. The tension levers 100.1 are rotatably mounted in the crank pins 100 at the distal ends thereof (right side in FIG. 22), and as a result, are guided such that they can be displaced radially, such that a radial deflection of the tension lever results in a force- or form-locking clamping of the crank pin in the instrument-side coupling socket. The deflection of the tension lever results, in a path-controlled manner, by means of the control contour, which can be integrated in the threaded spindle, as indicated by way of example in FIGS. 21, 22, 23A-23C.

FIGS. 23A-23C show the steps for the path-controlled coupling procedure for the output drive assembly and the input drive assembly to one another, by means of the mechanical interface, this being prior to coupling the output drive element 100, and the input drive element 200 (FIG. 23A), in which the clamping effect is obtained after inserting the input drive pin into the coupling socket (FIG. 23B) and a maintaining of the clamping is obtained over the entire adjustment range through a mechanical, positively driven, operation of the tension lever.

FIG. 23A shows the situation prior to the coupling. The drive unit 1 is covered by a sterile casing 3, and the instrument shaft is secured to the drive unit 1. The input drive pin 100 is inserted in a lower boundary layer. A compression spring 200.1 in the instrument shaft supports the coupling process, in that it ensures that the coupling socket 200 is likewise located in a lower boundary layer. FIG. 23B shows the situation immediately following the coupling. By extending the pin 100 out of the drive unit 1, it is inserted into the coupling socket of the instrument shaft. Subsequently the tension lever 100.1 is forced radially outward by the control contour on the threaded spindle 100.2, and thus establishes the friction- or form-locking connection thereby. As is shown in FIG. 23C, this mechanical connection is maintained by means of a mechanical positive guidance of the tension lever in the entire working range of the instrument shaft, with translationally adjusted or actuated pins 100 in the embodiment example (vertical in FIGS. 23A-23C).

FIGS. 24A-24B show mechanical interfaces of instrument assemblies according to further embodiments of the present invention. Features corresponding to those in the other embodiments are indicated by identical reference symbols, such that only the differences shall be addressed below, and otherwise, reference is made to the overall description.

In the embodiment in FIGS. 24A-24B, the crank pin, or the clamping means drive, respectively, is force-controlled, the clamping force, contrary to the embodiments in FIGS. 21, 22, 23A-23C, 24A-24B, is not controlled by a positive guidance of the output drive element, or pin, respectively, applied by the actuator. The coupling between the output drive element and the input drive element is established by an elastic expansion of the input drive pin 100, and can be force- or form-locking. By tightening a clamping mechanism, or means, respectively, the input drive pin is radially expanded. In the embodiment in FIGS. 24A-24B, the clamping means has a locking-ball mechanism for this, which can have, for example, in a variation that is not depicted, an expanding mandrel, an articulated lever mechanism, or a lock washer. In order to maintain the clamping force over the entire adjustment range, in one embodiment of the present invention the clamping means is designed in general such that, as is indicated in FIGS. 24A-24B by way of example, it has a kinematic dead center. This means, in the present case, in particular, that there is a kinematic range in which the clamping means remains open in a stable manner, or does not couple the output drive and input drive elements, respectively, and there is a further kinematic range, separated from the first by a dead center, in which the clamping means remains closed in a stable manner, or couples the output drive and input drive elements. In the embodiment in FIGS. 24A-24B, the clamping means has numerous locking balls 100.6 distributed for this purpose on the circumference of the input drive pin 100, and an actuating stud 100.2 having a spherical head, the diameter of which is greater than the inner ring defined by the not radially expanded locking balls. The clamping means is operated, or actuated, in that the actuating stud 100.2 is inserted into the input drive pin 100, and the locking balls 100.6 are thus pressed radially outward. As a result, a separate elastic body in the form of an extension sleeve 100.1 is expanded in terms of its diameter, which can be notched or slotted, in order to keep the actuation force as low as possible. This sleeve prevents, in an advantageous manner, point contact between the locking balls and the sterile barrier, which encases the pin 100 (not shown), and enables a uniform pressure to be exerted over the largest possible contact surface. As a result, the contact rigidity can be increased, and the surface pressure to the sterile barrier can be minimized. The actuating stud 100.2 is displaced beyond the dead center of the locking-ball mechanism, such that the locking balls are retracted slightly, radially inward, behind the spherical head of the actuating stud, in order to maintain the clamping force in a stable manner.

A spindle drive, in particular, can serve as an actuator for actuating the output drive element or the input drive element, as is explained, for example, in reference to FIG. 22, wherein the clamping mechanism, or the clamping means, can be actuated in relation to the actuator, or independently thereof. In the first case, the insertion movement of the drive unit acts on the actuating stud 100.2, as explained in reference to FIGS. 23A-23C.

FIGS. 25A-25C show the steps for the force-controlled coupling process of the output drive assembly and the input drive assembly to one another by means of the mechanical interface in FIGS. 24A-24B, in a depiction corresponding to FIGS. 23A-23C, to which supplementary reference is made. FIG. 25A shows the situation prior to the coupling. The drive unit 1 is covered by a sterile casing, and the instrument shaft is secured to the drive unit. The input drive pin 100 is inserted in a lower boundary layer. FIG. 25B shows the situation immediately following the coupling: in order to reliably insert the input drive pin into the coupling socket of the instrument shaft, the output drive element 100 is driven against an end stop in the instrument shaft, and the coupling mechanism is triggered, or the clamping means is actuated, respectively. The locking balls 100.6 are pressed radially outward by the actuating stud 100.2, and the mechanical connection of the output drive element and the input drive element is thus established. As shown in FIG. 25C, the mechanical connection is maintained in the entire working range of the instrument, because the dead center of the clamping mechanism has been overcome.

In an instrument assembly according to the present invention, the instrument shaft can have a flange, in particular, wherein the mechanical interface is disposed on a surface of this flange that faces the end effector, faces away from the end effector, or a lateral surface of this flange. In other words, the drive unit 1 can be designed as a "back-loading," "front-loading" or "side-loading" drive unit.

For clarification, advantageous joining directions for an instrument shaft onto a drive unit of an instrument assembly are schematically depicted in FIGS. 25A-26C, according to various embodiments of the present invention. According to one embodiment, which is indicated by way of example in FIG. 26A, the instrument shaft is joined to the drive unit along the insertion direction of the instrument into the patient, which is referred to for this reason, as "back-loading." In another embodiment, indicated by way of example in FIG. 26B, the instrument shaft is joined to the drive unit counter in the insertion direction of the instrument into the patient, which is referred to, accordingly, as "front-loading." In another embodiment, indicated by way of example in FIG. 26C, the instrument shaft is joined to the drive unit in a direction transverse to the insertion direction of the instrument in the patient, which is referred to as "side-loading." The instrument assembly shown in FIG. 26A-26C can relate, in particular, to one of the embodiments explained in reference to one of the other figures, such that reference is made thereto for a description thereof.

Figures 27A, 27B, 27C:
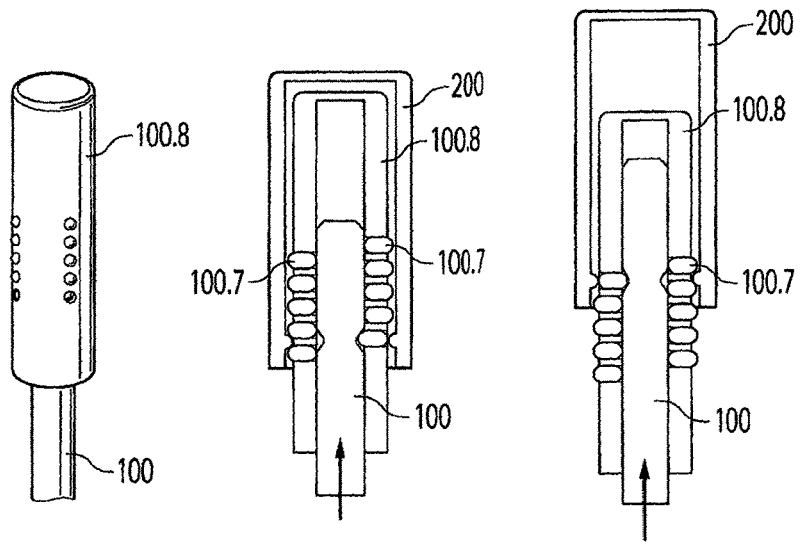
FIGS. 27A-27C, 28, 29: mechanical interfaces of instrument assemblies according to further embodiments of the present invention.

FIGS. 27A-27C show a mechanical interface of an instrument assembly according to another embodiment of the present invention, this being in a perspective view (FIG. 27A), and two sections in different stroke positions (FIGS. 27B, 27C). Features corresponding to those in other embodiments are indicated with identical reference symbols, such that only the differences shall be addressed below, and otherwise, reference is made to the overall description.

With this embodiment, a gap having a radial wave shape is formed between the pin and the cut-out, in which a radially displaceable, axially stationary, intermediate element assembly is disposed, for transferring a translational movement via a sterile barrier.

For this, the pin 100 is designed with a circumferential notching, and an instrument shaft-side coupling socket 200 is designed with a circumferential annular profile on the inside thereof. The pin and the coupling socket are designed such that, in the joined state, a preferably equidistant wave-shaped gap is formed between these components. Rod-shaped intermediate elements 100.7 of an intermediate element assembly are inserted in this gap, which support a cage sleeve 100.8 in a spatially stationary manner, and can only be displaced radially. The thin, foil-like sterile barrier (not shown) is disposed between the coupling socket and the cage sleeve. By axially displacing the pin 100 (vertically in FIGS. 27A-27C), the input drive-side part of the wave-shaped gap is pushed between the pin and the coupling socket. As a result of the kinematic constraints in the interface, the coupling socket is pushed axially, or translationally, respectively, onto the pin, as is indicated in the series of figures, FIGS. 27B-27C. In a further development, the intermediate elements of the intermediate element assembly can be designed in the manner of sleeves, on the front surfaces of which balls are rotatably disposed in order to reduce the frictional resistance.

Figure 28:
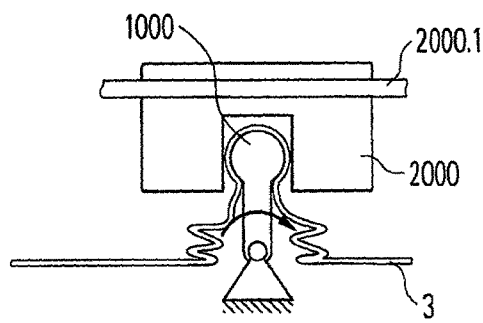
Figure 29:
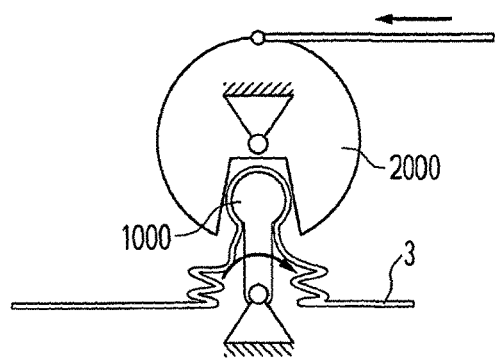

FIGS. 28, 29 show mechanical interfaces of instrument assemblies according to further embodiments of the present invention. Features corresponding to those in other embodiments are indicated with identical reference symbols, such that only the differences shall be addressed below, and otherwise, reference is made to the overall description.

In this embodiment, the mechanical interface has a tilt lever, in order to transfer, in particular, a translational input drive movement via a sterile barrier. A particular advantage of this concept is a simple design for the sterile barrier: it need only be designed for the tilting movement of the lever, and can, in a further development, be manufactured in a simple manner as a plastic molded part, from a thermoplastic elastomer or silicone, for example, in particular as a deep-drawn film. The tilting angle of the lever can be adjusted by a rotary drive, in one embodiment, in particular an electric motor, optionally with a gearing interposed therebetween. The sterile barrier can encase the entire drive unit, and can also be pulled over the lever. In a further development that is not shown, the lever (in FIGS. 28, 29, by way of example: 1000) can, in general, be extended at its end facing away from the contact, or the sterile barrier (below in FIGS. 28, 29), beyond its pivot bearing, and be coupled there to a drive, or an instrument shaft-side drive train, respectively, such as a pull cable or a rod assembly, for example.

The tilt lever (in FIGS. 28, 29 by way of example: 1000) in one embodiment is coupled, in general, in a form-locking manner with a coupling part, in particular it can be inserted in a groove of a coupling part, (in FIGS. 28, 29 by way of example: 2000) as is indicated in the embodiments in FIGS. 28, 29. The tilt lever can be coupled, in particular, with an output drive element of the output drive assembly of the drive unit, or represent such, and the coupling part, accordingly, can be coupled to an input drive element of the input drive assembly of the instrument shaft, or represent such, and the coupling part can be coupled, accordingly, to an output drive element of the output drive assembly of the drive unit, or represent such.

The coupling part 2000 can, in one embodiment, indicated by way of example in FIG. 28, can be guided by a thrust bearing 2000.1 such that it can be adjusted in a translational manner. Thus, the rotational movement of the tilt lever 1000 is tapped into, for example, in the instrument shaft, as a translational movement, or is exerted on the drive unit as a translational movement. The kinematics of this interface is nonlinear, and is therefore, in a further development, compensated for in a computer, or in the drive unit control device.

Because a tilt lever in a further development is gimbal-mounted, movements in two degrees of freedom can also be transferred. For this, the illustration in FIG. 28, by way of example, is to be regarded as a cutaway depiction in two planes that are perpendicular to one another. An interface with a tilt lever for actuating in three degrees of freedom can be formed by means of the tilt lever being able to be displaced optionally along its longitudinal axis as well (vertically in FIG. 28).

In another embodiment, indicated by way of example in FIG. 29, the coupling part, coupled to the tilt lever in a form-locking manner, can likewise be rotatably supported, or guided in a pivot bearing. This embodiment can also be expanded for actuation of two or more degrees of freedom, as is explained above in reference to FIG. 28.

The figures in FIGS. 30A-30C, 31A-31C, 32A-32B show instrument assemblies according to further embodiments of the present invention, having a sterile barrier which—at least during a surgical operation—encases a drive unit, and is disposed between the drive unit and an instrument shaft coupled thereto by means of a mechanical interface. The drive unit, instrument shaft and/or mechanical interface can, in particular, be of the type in the other embodiments and figures, such that features corresponding to those in the other embodiments are indicated with identical reference symbols, and only the differences shall be addressed below, and otherwise, reference is made to the overall description.

The sterile barrier can in general be designed, in particular as a single piece and/or as a film tube. In a further development, the sterile barrier is designed to be airtight, or encases the drive unit in an airtight manner, respectively. As is described below, in reference to FIGS. 30A-30C, 31A-31C, 32A-32B, a transference of an input drive movement, or an actuation, respectively, from an output drive element to an input drive element does not occur through an opening in the sterile barrier, but rather, is transferred via the sterile barrier that is closed in this region.

In one embodiment, which is depicted in two variants in FIGS. 30A-30C, the sterile barrier has at least one pre-tensioned cuff in the region of the mechanical interface, in particular, one each in the region of each output drive element, in an adjustment direction of the output drive and input drive assemblies. The pre-tensioned cuff is designed as an elastic bellows in a further development, in particular as an elastomer bellows, preferably as a corrugated membrane (in FIG. 30A, by way of example: 3.2) or as a corrugated bellows (in FIG. 30B, by way of example: 3.3), which is directly integrated in the sterile casing, or is an integral part thereof, which, in particular, is originally formed therein, or shaped therein. In another embodiment, depicted as a variant in FIG. 30C, the sterile barrier has at least one cuff in the region of the mechanical interface, in particular one each in the region of each output drive element, which is not pre-tensioned, in an adjustment direction of the output drive and input drive assemblies. This, at least substantially, not pre-tensioned cuff is designed, in a further development, as a preferably elastic sleeve, in particular as a thermoplastic or elastomer sleeve (in FIG. 30C, by way of example: 3.4), which is integrated directly in the sterile casing, or is designed as an integral part thereof, in particular, is originally formed therein, or shaped therein.

FIG. 30A shows one embodiment as a flat corrugated membrane 3.2, FIG. 30B as a corrugated bellows 3.3, the cross-section of which can be, in particular, cylindrical or conical. Both bellows form cuffs in the adjustment direction (vertical in FIGS. 30A-30C), in which a returning pre-tension is imposed by the pleating, or the pre-formed corrugation, which compensates for the stroke occurring when the output drive element (in FIGS. 30A-30C, by way of example: 10A, 100 or 1000) is actuated in an adjustment direction.

In another embodiment, which is depicted in three variants in FIGS. 31A-31C, the sterile barrier has at least one seal (in FIGS. 31A-31C, by way of example: 3.5) in the region of the mechanical interface, in particular one each in the region of each output drive element, which can be translationally displaced without contact. This can be designed, in a further development, indicated by way of example in FIG. 31A, as an axially displaceable gap seal. Likewise, in a further development, indicated by way of example in FIG. 31B, it can be designed as a labyrinth seal. As indicated by way of example in FIG. 31C, a seal that can be displaced translationally can preferably be telescoping, in particular in the form of a one- or multi-step telescoping sleeve (in FIG. 31C, by way of example: three-step).

FIGS. 32A-32B show a further embodiment of the sterile barrier in the region of the mechanical interfaces, in particular of at least one, preferably each, output drive element or input drive element, which is distinguished by a very simple structure and production. The sterile barrier has a sterile element extension for at least one, preferably each, output drive or input drive element, which can be releasably connected to an element base, which passes through the sterile barrier in a destructive manner. As indicated in the series of figures, FIGS. 32A-32B, an output drive element base 11 passes through the sterile barrier 3, by way of example, in a destructive manner, and the region that has passed through the barrier is releasably connected with a sterile element extension 3.6 to an output drive element, as is indicated in the other embodiments and figures, for example, by the reference symbols 10A, 10B, 100 or 1000. Likewise, conversely, an input drive base 21 can also pass through the sterile barrier 3 in a destructive manner, and can be releasably connected with its region passing through the barrier, with a sterile element extension 3.6, to an input drive element, as is indicated in the other embodiments and figures, for example, by the reference symbols 20A, 20B, 200 or 2000.

In one embodiment, indicated by way of example in FIGS. 32A-32B, the sterile barrier has, in the regions of the element bases passing through it, in each case one, preferably annular, reinforcement 3.7, formed, for example, by plastic disks glued thereto, originally formed local wall thickness reinforcements, and/or local modifications of the material. In the middle of the reinforced region, the sterile barrier can again be designed as a thin membrane. After it has been encased, the drive unit is placed on a pin of the sterile extension 3.6, as described above. For this, the thin membrane of the sterile barrier is penetrated inside the annular reinforcement. The securing of the sterile extension can, in particular, be friction-locking, material bonded, and/or form-locking, by means of a screw or bayonet connection, or it can also be obtained by means of a ball-lock bolt.

FIGS. 33A-33B show an instrument assembly according to a further embodiment of the present invention, having a sterile barrier 3, which—at least during a surgical operation—encases a drive unit 1, and is disposed between the drive unit and an instrument shaft 2 coupled thereto by means of a mechanical interface. The drive unit 1, instrument shaft 2, and/or mechanical interface 3 can, in particular, be of the types in the other embodiments and figures, such that features corresponding to those in the other embodiments are indicated by identical reference symbols, and only the differences shall be addressed below, and otherwise, reference is made to the overall description.

The instrument assembly has an attachment element in the form of a sterile adapter 4, for the releasable attachment of the instrument shaft 2 to the drive unit 1, which is to be, or is, disposed on a surface of the sterile barrier facing away from the drive unit.

The drive unit 1, which has numerous crank pins 100, by way of example in the embodiment depicted in FIGS. 33A-33B, is enclosed in the sterile casing 3. The covers for the output drive elements are integrated in the sterile casing in the embodiment depicted in FIGS. 33A-33B, by way of example as elastomer bellows, as has been explained above in reference to FIGS. 30A-30C. After the drive unit is enclosed by the sterile barrier, the sterile adapter 4 is secured from the outside onto the drive unit in its sterile packaging. The adapter 4 thus does not interact with the output drive elements 100, but rather, only makes available a mechanical interface for attaching the instrument shaft 2 to the encased drive unit 1. This separation of the mechanical coupling from the output drive and input drive elements, on one hand (by means of the mechanical interface) and the mechanical attachment of the drive unit and the instrument shaft, on the other hand (by means of the attachment element, or the adapter, respectively), facilitates the sterile manipulation of the instrument assembly. In one embodiment, indicated by way of example in FIGS. 33A-33B, the adapter 4 can be, or is, connected to the instrument shaft and the drive unit in a form- and/or friction-locking manner, by means of locking, or clip, connections, for example, wherein the sterile casing 3 is also sealed, or free of holes, respectively, between the locking projections and cut-outs on the drive unit and adapter, thus ensuring sterility.

The preceding instrument assemblies are robot-guided, or configured for attachment to a manipulator of a manipulator surgical system, respectively, in a further development. In particular, for this the drive unit 1, the instrument shaft 2, and/or an attachment element, or an adapter 4, respectively, can have a correspondingly configured attachment interface, such as cut-outs, locking mechanisms, or suchlike, corresponding thereto.

In the above, components of an inventive instrument assembly, in particular, have been described, wherein, however, methods for equipping a manipulator of a manipulator surgical system are also comprised in the invention, in which a modular, motor powered, drive unit and an instrument shaft are releasably connected to one another, and the output drive assembly and the input drive assembly are coupled to one another thereby, by means of the mechanical interface, as is shown in the various series of figures, FIG. 23A→FIG. 23B→FIG. 23C; FIG. 25A→FIG. 25B→FIG. 25C; and FIG. 32A→FIG. 32B, as well as by the assembly arrows in FIGS. 26A-26C and FIGS. 33A-33B.

FIG. 34 shows a part of a robot-guided minimally invasive surgical instrument according to one embodiment of the present invention, having a drive module 10 and an instrument shaft 20, releasably connected thereto in a manner that is not shown in detail, having an end effector in the form of a moveable clamp, having two blades 2.1, 2.2. One embodiment of the invention shall be explained below, in particular, based on the blade 2.1; the construction and function of the blade 2.2 is analogous thereto, such that reference in this respect is made thereto.

The blade 2.1 has a rotational degree of freedom $q_1$ with respect to the instrument shaft 20. In order to actuate this degree of freedom, or to open or close the blade 2.1 of the clamp, respectively, two drive trains 21, 22 of an instrument shaft-side drive train assembly are connected in an articulated manner, in opposing directions, to the blade 2.1. The drive trains 21, 22 can, for example, be push rods, or tappets, respectively, which are mounted in the instrument shaft such that they can be moved in a translational manner.

In order to actuate the push rods 21, 22 in opposing directions, the input drive module has two drive trains 11, 12, acting in opposing directions, which can be actuated in opposing directions by means of an electric motor 13 of a drive in the input drive module. The drive trains 11, 12 can likewise be push rods, or tappets, respectively, which are mounted in the input drive module such that they can be moved in a translational manner.

A flexible sterile barrier 4 is, optionally, disposed in an interface between the input drive module and the instrument shaft, by means of which the instrument shaft-side drive train assembly and the input drive module-side drive train assembly can be releasably coupled to one another.

The drive train assemblies are translationally coupled in a one-sided manner: the push rods, or tappets 11 and 21, or 12 and 22, respectively, are translationally displaceable, and can only transfer pressure forces via the sterile barrier.

In order to ensure the force connection between the push rods, or tappets 11 and 21, and 12 and 22, which can only transfer pressure forces via the sterile barrier 4, the input drive module-side drive train assembly is pre-tensioned against the interface, as indicated in FIG. 34, by means of a bearing of the electric motor 13, pre-tensioned by means of a spring 5, with the drive train assembly coupled thereto.

A first metering means, in the form of a strain meter strip 31 of a metering assembly, is disposed on the first input drive module-side drive train 11 for registering a load $F_1$ in this drive train, and a third metering means, in the form of a strain meter strip 33 of a metering assembly, is disposed opposite the first metering means.

A second metering means, in the form of a strain meter strip 32 of the metering assembly, is disposed on the second input drive module-side drive train 12 for actuating the same degree of freedom $q_1$ of the blade 2.1 of the end effector, for registering a load $F_2$ in this drive train, and a fourth metering means, in the form of a strain meter strip 34 of the metering assembly, is disposed opposite the second metering means.

As is shown in FIG. 35, the first metering means 31 in a first branch, the second metering means 32 in a second branch, the third metering means 33 in a third branch, and the fourth metering means 34 in a fourth branch, of a Wheatstone full-bridge circuit are coupled to one another with signal-based technology.

For this, the second metering means 32 is interposed in a supply voltage $U_E$ in series with the first metering means 31, the third metering means 33 is interposed in the supply voltage in parallel to the second metering means 32, and the fourth metering means 34 is interposed in the supply voltage in parallel to the first metering means 31.

Through the interconnection of the first and third, or second and fourth, metering means, respectively, to a linked output signal in the form of a bridge output voltage $U_A$, bending loads, in particular, in the drive trains 11, 12, which do not correspond to any active forces of the end effector, can be compensated for. By interconnecting the first and third, or second and fourth, metering means, respectively, in the bridge output voltage $U_A$, the shared pre-tension, in particular, of the input drive module-side drive train assembly, which acts on the opposing tappets 11, 12, and thus is not an active force actuating the blade 2.1, can be compensated for. With equalized bridges in the unloaded state, an at least substantially linear correlation is obtained, in the embodiment example, between the force actuating the blade 2.1, which has been freed of the pre-tension of the spring 5, i.e. is active, and twice the tension registered by the strain meter strip 31, thus, advantageously, an additional, signal-based reinforcement of the registered load.

As is indicated in FIG. 34, the metering means 31-34 of the metering assembly are oriented for registering axial pressure loads in the longitudinal direction of the drive trains 11, 12, and disposed in radial cut-outs in the drive trains 11, 12.

In particular, in order to control the electric motor 13 and/or a manual teleoperation means, such as a mirroring instrument, for example (not shown), the active, or generalized loads $F_1$, $F_2$ are registered by the metering means 31-34, and the drive and the teleoperation means are controlled on the basis of these registered loads. In this manner, a haptic feedback can be transmitted to the teleoperator, for example, pertaining to the clamping force exerted by the end effector on a lumen, or pertaining to, respectively, the resistance exerted by the lumen on the clamps 2.1, 2.2.

FIG. 36 shows, for purposes of a more compact depiction, both a part of a control means, as well as a method according to one embodiment of the present invention.

A control means 3, which can be implemented in a control for the robot, for example, which guides the minimally invasive surgical instrument in FIG. 34, receives the linked output signal $U_D$ from the metering assembly 31-34 (cf. FIG. 35 as well), which is, as explained above, in particular, proportional to twice the load $F_1$ in the drive train 11. The control means 3 establishes a command S based on this load, registered by the metering assembly, which it conveys, by way of example, to a motor control for the electric motor 13, or a teleoperation means in the form of a mirroring instrument (not shown), such that the motor 13 implements a desired target force in the drive train 11, or, respectively, the mirroring instrument conveys a virtual load to the teleoperator, corresponding to the actual forces $F_{E1}$, $F_{E2}$ acting on the end effector.

A method, which is executed, for example, by the control means 3 explained above, controls the drive 13, or the mirror instrument, respectively, in a corresponding manner, in that, in one step, it receives the linked output signal $U_A$ from the metering assembly 31-34, and establishes the command S, based on this load registered by the metering assembly, which controls, for example, the motor control for the electric motor 13, or the mirroring instrument, such that the motor 13 implements the desired target force in the drive train 11, or the mirroring instrument, respectively, conveys the virtual load to the teleoperator, corresponding to the actual forces $F_{E1}$, $F_{E2}$ acting on the end effector.

FIG. 37 shows a part of a robot-guided, minimally invasive surgical instrument according to one embodiment of the present invention, in a partial section. The instrument has an instrument shaft 31 and a drive unit 30 releasably connected thereto.

The instrument shaft has an interface 42 for attachment to a robot 40, which is covered by a sterile casing 41.

The instrument shaft has numerous degrees of freedom, two of which are indicated, by way of example, in the embodiment example:

The instrument shaft has a tube 54, which is mounted in relation to an instrument shaft housing 53 in a pivot bearing. Two cable pull drums 57c, 57d running in opposite directions, act in opposite directions on a gear wheel 58, and are coupled, in each case, to input drive links that shall be explained in greater detail below, in the form of input drive tappets 37, 38 (cf. FIG. 38), which in turn, are actuated by output drive links in the form of output drive tappets 34, 35 (cf. FIG. 38). The output drive and input drive tappets 34/37, or 35/38, respectively, each form a pair of tappets, which are indicated in FIG. 37 by the numerals 45a-45d. The tube 54 can be rotated in the pivot bearing 55 in both directions by means of opposing actuations of the pair of tappets 45c, 45d, and thus, this degree of freedom of the instrument shaft 31 can be actuated.

An end effector (not shown) is disposed on the end of the tube 54 that is distanced from the drive unit, which has at least one degree of freedom in relation to the tube and/or at least one functional degree of freedom, such as the opening and closing of a forceps, for example. Two cable pull drums 57a, 57b, running in opposite directions, act in opposite directions on the end effector, and are coupled to input drive links in the form of input drive tappets 37, 38 (cf. FIG. 38), which shall be explained in greater detail below, which in turn are actuated by output drive links in the form of output drive tappets 34, 35 (cf. FIG. 38). A degree of freedom of the end effector can be actuated by mean of actuation of the pair of tappets 45a, 45b in opposing directions.

The input drive tappets 37, 38 are mounted, in the embodiment example, in a translational manner, or displaceably, in an interface 56a, or 56b, respectively, of the instrument shaft 31. In a variation, which is not depicted, rotational or rotatable input drive shafts can, likewise, be coupled in a non-rotatable manner to the output drive shafts; one embodiment of the present invention, having displaceable output drive and input drive links, is thus explained, merely by way of example, without being limited thereto.

The drive unit 30 has a housing 49, in which, by way of example, two input drive modules 47a, 4b for actuating the degrees of freedom, explained above, of the instrument shaft, are disposed. The input drive modules each have a drive in the form of an electric motor 44a, or 44b, respectively, and an output drive link assembly having two translationally moveable output drive links, which form the output drive tappets of the pair of tappets 45a, 45b, or 45c, 45d, respectively.

The actuation of the input drive tappets by the output drive tappets shall be explained below in reference to FIG. 38. For this, the pairs of tappets 34/37 and 35/38 can likewise represent the aforementioned pairs of tappets 45a and 45b, or 45c and 45d.

The drive 44, which can be the drive 44a or 44b in FIG. 37, actuates, in opposing directions, the two output drive tappets 34 and 35, which are displaceably mounted in a housing for the input drive module 47, which can be the input drive module 47a or 47b in FIG. 37. The output drive link and input drive link assemblies 34, 35 and 37, 38 are coupled in a one-sided manner in the embodiment example, via an optional, flexible sterile barrier 32. The input drive tappets 37, 38 are coupled to a rocker via coupling rods, which in turn, actuates the cable pull drums 57.1, 57.2 in opposing directions, which can be the cable pull drums 57a, 57b, or 57c, 57d in FIG. 37. The coupling rods and rocker form a gearing, which is encircled in FIG. 38 with a line consisting of dots and dashes.

The input drive modules are, as indicated in FIGS. 37, 38, moveably mounted and pre-tensioned in the housing 49 for the drive unit 30, in each case in a coupling direction (horizontal in FIG. 37; vertical in FIG. 38), against an input drive link assembly 37, 38. The coupling directions for the two input drive modules 47a, 47b are parallel (cf. FIG. 37) to one another, and to the respective actuation directions in which the links can be moved for actuating the degrees of freedom of the instrument shaft.

The input drive modules can have a compression spring, which restrains the input drive module in the housing, and pre-tensions it in the coupling direction, or against the input drive link assembly, respectively. This is indicated in FIG. 37 with the numerals 46a and 46b, and in FIG. 38, collectively, with the numeral 46.

In a variation shown in FIG. 41, the input drive module has, instead, a magnet assembly for pre-tensioning the input drive module.

In the embodiment example, the magnet assembly has an electromagnet 100 on the housing 49 of the drive unit, on a side facing the instrument shaft (below in FIG. 41) and a permanent magnet 101 opposite this, which is disposed on the input drive module 47. Additionally, an electromagnet 103 is disposed on the housing on a side facing away from the instrument shaft (above in FIG. 41), and a permanent magnet 104 is disposed opposite this on the input drive module. Instead of the permanent magnets 101 and/or 104, a magnetically soft region can also be provided, which can be attracted to the electromagnets 100 or 103 (when they are supplied with current).

The activated electromagnet 100 magnetically attracts the input drive module 47 in the coupling direction (downward in FIG. 41) and thus pre-tensions the output drive link assemblies 34, 35 against the input drive link assembly (not shown in FIG. 41). Likewise, the activated electromagnet 103 can repel the permanent magnet 104 of the same pole, and thus pre-tension the input drive module 47 magnetically in the coupling direction, against the input drive link assembly.

In a not depicted variation, one of the two electromagnets 100, 103 can be omitted. Additionally or alternatively, in a variation, instead of the electromagnets 100 and/or 103, permanent magnets can also be provided. The pre-tension effect of a permanent magnet 101 can be reduced by supplying the electromagnet 103 with current, in particular, it can be eliminated. If, in a variation, a permanent magnet is disposed in place of the electromagnet 103, having the opposite pole as that of the permanent magnet 104, or attracting this magnet, respectively, or the permanent magnet 104 is replaced by a magnetically soft region of the input drive module, then, as a result, a permanent magnetic input drive module locking assembly for locking the retracted input drive module is implemented, which shall be explained in greater detail below, in reference to FIGS. 40A, 40B.

In the embodiment in FIG. 41, the magnet assembly has numerous, preferably non-magnetic, spacing elements 102, which prevent a direct contact between the permanent magnets or electromagnets 100 on the housing of the drive unit with the magnetically soft or hard region, in particular (further) permanent magnets 101 on the input drive module. Likewise, preferably non-magnetic, spacing elements 105 prevent a direct contact between the permanent magnets, or electromagnets 103 and the magnetically soft or hard region, in particular (further) permanent magnets 104.

FIG. 39 shows an input drive module and an input drive link assembly coupled thereto, according to another embodiment of the present invention corresponding to that depicted in FIG. 38. Features corresponding to those in the other embodiments are indicated with identical reference symbols, such that reference is made to their description, and only the differences shall be addressed below.

As is shown by way of example in FIG. 38, an input drive module 47 can be moveably mounted directly in the housing 49 of the drive unit 30, in particular in a form-locking manner, by means of one or more grooves and/or ribs, for example. Additionally or alternatively, as is shown, only by way of example, in the embodiment in FIG. 39, in one embodiment of the present invention, an output drive link assembly can be moveably mounted in the housing of the drive unit, wherein the drive, in particular an input drive module housing 47.1, is supported therein, moveably mounted on the output drive link assembly, and is restrained, in particular in an elastic manner and/or by means of permanent magnets and/or electromagnets, against the housing for the drive unit, and as a result, is pre-tensioned in the coupling direction. In the embodiment in FIG. 39, the output drive tappets 34, 35 are each moveably mounted in thrust bearings in the housing 49 for the drive unit. A housing 47.1 for the input drive module, in which the input drive acting on the output drive tappets 34, 35 in opposing directions is supported, is restrained by a magnet assembly or compression springs 46 against the housing 49 for the drive unit, and as a result, is pre-tensioned in the coupling direction (vertically downward in FIG. 39).

FIGS. 40A, 40B show an input drive module and an input drive link assembly coupled thereto according to another embodiment of the present invention corresponding to that in FIG. 38. Features corresponding to those in the other embodiments are indicated by identical reference symbols, such that reference is made to their description, and only the differences shall be addressed below. FIG. 40A shows the input drive module thereby, in a state in which it is coupled to the input drive link assembly, FIG. 40B shows the retracted, and locked in place, input drive module.

As explained above in reference to FIG. 41, the input drive module 47 can be retracted against the pre-tensioning by means of a selective, in particular a controlled, supplying of current to a magnet assembly having at least one electromagnet 100 and/or 103. This can, in particular, facilitate a coupling and decoupling of the drive unit to and from the instrument shaft, because the (full) pre-tensioning does not have to be overcome, in particular manually, thereby. Thus, a magnet assembly supplied with current in a corresponding manner, as has been explained in reference to FIG. 41, represents a magnetic retraction assembly for retracting the input drive module against the pre-tensioning.

In the embodiment in FIG. 40, the drive has an output drive means in the form of a rocker 59, to which the output drive tappets 34, 35 are coupled in opposing directions by means of coupling rods. In order to actuate a degree of freedom of the instrument shaft, the drive requires only a limited angular range, which thus defines an actuating range. By this means, a retraction range is delimited by a mechanical stop 60 for the rocker 59, which extends for this purpose out of a housing for the input drive module 47.1.

As long as the input drive moves the rocker within the actuation range, as indicated in FIG. 40A, the output drive tappets are actuated in opposing directions. When the end of the retraction range has been reached, the rocker 59 rests against the mechanical stop 60, as shown in FIG. 40B. By rotating the rocker 59 further into the retraction range, the input drive displaces the input drive module against the pre-tension of the spring element 46 via the rocker 59, and thus pulls the input drive module back, by means of a motor, against the pre-tensioning. In a, not shown, variation, the stop 60 does not interact with the rocker 59, but rather, with one or both of the tappets 34, 35.

As is depicted in FIG. 41, the retraction assemblies 59, 60 can also be combined with a magnetic pre-tensioning, in particular by means of a magnet assembly having permanent magnets 101 and/or 104.

In particular, in order to relieve the input drive, an input drive module locking assembly for locking the retracted input drive module in place can be provided. This has, in the embodiment in FIG. 40B, a spring-loaded and manually or automatically releasable latch 61, by means of which the output drive module, which has been retracted against the pre-tensioning, is secured in a form-locking manner.

The input drive module locking assembly can also be magnetic. When a magnet, as explained in reference to FIG. 41, in particular a permanent magnet 101, magnetically attracts a magnetically soft region or a permanent magnet 104 of the opposite pole, on the input drive module, the (more strongly pre-tensioned) input drive module can be magnetically locked in place. In one embodiment of the present invention, the retraction assembly is also designed to release the locking, or to adjust the input drive module in the coupling direction. For this, in one embodiment, a mechanical counter-stop can be provided, in general, against which the output drive means is supported, when it is adjusted in a feed range differing from the actuation and retraction range. In the embodiment in FIG. 41, a corresponding counter-stop 106 is disposed on the housing for the drive unit, and defines a feed range differing from the actuation range and the retraction range defined by the stop 60. When the feed range has been reached, the rocker 59 rests, as depicted in FIG. 41, against the mechanical counter-stop 106. By further rotating the rocker 59 into the feed range, the drive displaces the input drive module, via the rocker 59, against the locking action of the magnet assembly 103, 104 in the coupling direction (vertically downward in FIG. 41). Here as well, in a variation, the stop 60 can interact with one or both of the tappets 34, 35, instead of with the rocker 59.

As is discernable, in particular, in FIGS. 42A-42B, 43A-44B, 44A-44B, 45A-45B, and 46A-46B, the coupling direction (horizontal in the figures), in which the input drive module 47A, 47B is moveably mounted and pre-tensioned in the housing 49, forms an angle with the longitudinal axis of the instrument shaft 31 (vertical in the figures), which is substantially 90 degrees.

In the following, with reference to FIGS. 42A-42B, 43A-43B, 44A-44B, 45A-45B, 46A-46B, a mounting element for the instrument shaft, for a form-locking, releasable attachment of the drive unit shall be explained according to various embodiments of the present invention. Features corresponding to those in other embodiments are indicated by identical reference symbols, such that reference is made to their description, and only the differences shall be addressed below. The figures show, in each case, a part of the instrument shaft, with its mounting element, and the drive unit, still separated therefrom, wherein an insertion direction for the drive unit in the mounting element is indicated by a movement arrow.

The mounting element 80 in the embodiment in FIG. 42A has a chamfered insertion opening 140 for inserting the drive unit 30 in an insertion direction, wherein the insertion direction is parallel to the longitudinal axis of the instrument shaft (vertical in FIG. 42A). The insertion opening 140 is disposed on the side facing away from the instrument shaft (above in FIG. 42A).

The moveable input drive links of the input drive link assembly 45.2 of the instrument shaft, such as the input drive tappets 37, 38, by way of example, are perpendicular, as explained above in reference to FIGS. 38-41, to the longitudinal axis of the instrument shaft 31, as far as its mounting element 80, wherein the interface, or the contact plane for the input drive link assembly 45.2 is parallel to the longitudinal axis.

In the embodiment in FIG. 42B, the input drive link assembly 45.2 of the instrument shaft 31 is disposed in a recess 142. Additionally or alternatively, the output drive link assembly 45.1 of the drive unit 30, the output drive tappets 34, 35, for example, as explained above in reference to FIGS. 38-41, is disposed in a recess 143, when it is retracted by the retraction assembly against the pre-tensioning. After inserting the drive unit 30 in the mounting element 80, and unlocking the retraction assembly, or building up a pre-tension, respectively, the pre-tensioned output drive link assembly 45.1, which then protrudes out of the recess 143, makes contact with the input drive link assembly 45.2 of the instrument shaft 31.

The embodiment in FIG. 43A corresponds substantially to that in FIG. 42A. For the form-locking attachment of the drive unit 30 in the mounting element 80 of the instrument shaft 31, a bayonet coupling, having at least one projection 151 on the housing 49, is provided, which engages in a cut-out 150 in the mounting element 80 as a result of rotating the drive unit. Likewise, the projection 151, in a variation, can engage in the cut-out 150 in the mounting element 80 as a result of a displacement (horizontally, toward the left in FIG. 43A), instead of by means of a rotation, wherein this displacement preferably occurs as a result of applying the pre-tensioning force. The user thus pushes the drive unit (vertically from above in FIG. 43A) into the mounting element. Subsequently, a coupling procedure is initiated, in particular manually or automatically, in which the pre-tensioning force is applied to the interfaces. As a result, the projection 151 on the drive unit is pushed into the cut-out 150, perpendicular to the insertion direction, and thus the drive unit is locked in place in a form-locking manner.

The embodiment in FIG. 43B corresponds substantially to those in FIGS. 42A, 43A. The mounting element 80 in this embodiment has a multi-part form-locking guide for inserting the drive unit 30 in the insertion direction. The guide has numerous guide grooves 152, which interact with corresponding projections 153 on the housing 49 for the drive unit 30 in a form-locking manner, in order to attach the housing in a form-locking manner in the mounting element 80 of the instrument shaft 31. The guide grooves 152 are substantially L-shaped, such that the drive unit in turn can be secured in the mounting element in a form-locking manner by means of a rotation thereof. As with the bayonet coupling of the embodiment according to FIG. 43A, the drive unit, after it has been inserted in the mounting element, is rotated, and as a result, secured in a form-locking manner, such that it is pre-tensioned counter to the insertion direction, by means of a corresponding oversize, or an elastic spring element (not shown), in order to thus counteract, in a friction-locking manner, a reverse rotation, and thus a release of the drive unit. Likewise, in a variation such as the variation explained above in reference to FIG. 43A, the projections 153 can be displaced perpendicular to the insertion direction, as a result of a displacement in the short leg of the cut-out 152, wherein this displacement in turn, preferably occurs by applying the pre-tensioning force. The user thus pushes the drive unit (vertically from above in FIG. 43B) into the mounting element. In doing so, the projections 153 slide in the long leg of the L-shaped cut-outs 152, as far as the bend thereof. Subsequently a coupling procedure is initiated, in particular manually or automatically, in which the pre-tensioning force is applied to the interfaces. As a result, the projections 153 on the drive unit are pushed into the cut-outs 152, perpendicular to the insertion direction, and thus the drive unit is locked in place in a form-locking manner.

The embodiment in FIG. 44A corresponds substantially to that in FIG. 43B, wherein here, a guide rib 161, which extends in the insertion direction, is inserted in a complementary guide groove 160 on the mounting element 80, and will be, or is, secured therein, in a friction-locking manner, for example. In one embodiment of the present invention, as is depicted by way of example in FIG. 44A, the mounting element has, in general, in addition to the insertion opening, a further opening (left in FIG. 44A), in particular in order to improve a signal-based and/or energy-based connection (not shown) for the drive unit.

In the embodiment in FIG. 44B, the insertion direction is perpendicular to the longitudinal axis of the instrument shaft. The insertion opening is disposed on the side facing away from the instrument shaft (left in FIG. 44B).

In the embodiment in FIG. 44B, a drive unit locking assembly is provided for the form-locking locking in place of the drive unit 30 in the mounting element 80, in the form of a moveable, pre-tensioned latch 167, which catches in the drive unit 30 when it is placed in the mounting element 80. Although it is not depicted, a drive unit locking assembly of this type, or similar thereto, can also be provided in the other embodiments, in particular in addition to, or alternatively to a form-locking securing, in particular a bayonet coupling, or a friction-locking securing.

The mounting element 80 in the embodiment in FIG. 44B has one or more guide ribs 165, which engage in corresponding guide grooves 166 in the housing 49 for the drive unit 30. As is described in reference to FIG. 42B, the input drive link assembly 45.2 is disposed in a recess 164.

The embodiment in FIG. 45A corresponds substantially to that in FIG. 44B, wherein the insertion opening can be closed by a pivotable lid 170, in order to secure the drive unit 30 against the insertion direction in a form-locking manner.

In the embodiment in FIG. 45B, the mounting element 80 can be pivoted in relation to the longitudinal axis of the instrument shaft. This makes it possible, as indicated in FIG.

45B by the movement arrow, to first insert the drive unit 30 into the mounting element that has been pivoted to a mounting position (cf. FIG. 45B), and then to pivot the mounting element into a locking position, wherein the drive unit is then secured in a form-locking manner in this locking position in the mounting element.

In the embodiment in FIG. 46A, the drive unit 30 has a convergent positive displacement means for forcing the input drive link assembly of the instrument shaft into the mounting element of the instrument shaft when the drive unit is being inserted. The convergent positive displacement means in the embodiment in FIG. 46A has a convex, in particular a chamfered or elliptical, surface, which converges in a first section 180*a* in the insertion direction, and thus pushes back input drive links of the input drive link assembly 45.2 that protrude further than normal in a form-locking manner. A surface 180*b* diverging in the insertion direction, likewise convex in the embodiment in FIG. 46A, adjoins the surface 180*a* converging in the insertion direction, in order to also push back input drive links that protrude from the mounting element 80 when removing the drive unit 30.

In the embodiment in FIG. 46B, the drive unit 30 has, on the contrary, a moveable positive displacement means, in the form of numerous rotatable rollers 181*a*, 181*b*, which pushes back input drive links of the input drive link assembly 45.2 that protrude further than normal during the insertion, and thus levels the input drive link assembly. After rolling over the rollers 181*a*, 181*b*, or the convex surface 180*a*, the input drive links then project, at least substantially, to the same degree toward the mounting element on the instrument shaft.

FIG. 47 shows, schematically, a surgical instrument according to one embodiment of the present invention, having an instrument shaft 20. The instrument shaft has a rigid, articulated, or flexible tube 22, on the distal end of which an end effector 21 is disposed, having one or more functional and/or kinematic degrees of freedom. In a proximal instrument housing 23 of the instrument shaft, an input drive module 25 is releasably connected, at an interface 24, to the instrument shaft. The tube 22 can be secured to, or rotatably mounted on, the instrument housing 23, such that the tube 22 has one degree of freedom about its longitudinal axis.

FIGS. 48A, 48B show this interface in different perspectives. For a better overview, only a few components of the input drive module 25 and the instrument shaft 20 are depicted, and are thus indicated with an apostrophe ('). In particular, only one drive train for actuating a degree of freedom of the instrument shaft is shown; further drive trains have an analogous construction, and are disposed, for example, parallel to the shown drive train.

Each drive train has an actuator in the form of an electric motor-gearing unit 31', the output drive shaft of which represents an output drive link of the input drive module that can rotate without limits.

An input drive link 32' is coupled to this output drive link in a manner described below, which is inserted in a form-locking manner in a thrust bearing 34' such that it can be displaced in a displacement axis B' in the instrument shaft.

The input drive link is connected to the end effector 21 by a pulling means, or a push rod 36, (not shown) in order to actuate the input drive link, wherein the push rod is parallel to the displacement axis B'. The input drive link can be displaced between two end stops 37.1, 37.2 (cf. FIGS. 53A-53B, not shown in FIGS. 48A-48B).

A linear groove 33' is disposed on the input drive link, which is perpendicular to the displacement axis B'. A guide element 30' is disposed eccentrically on the rotatable output drive link, and inserted in the groove such that it can be displaced, when the output drive link and the input drive link are coupled to one another. The rotational axis for the rotatable output drive link is perpendicular to the displacement axis B' of the displaceably guided input drive link and the groove.

The guide element 30' has a pin, on which a roller element in the form of a ball race is mounted, in a sliding or rolling manner. In a variation, instead of this, a roller element without an outer race can also be disposed on the pin.

FIGS. 49A-49B show the steps for coupling the guide element to the groove, and FIGS. 49C-49F show the steps for the actuation of the input drive link by the output drive link.

Figure 49D:
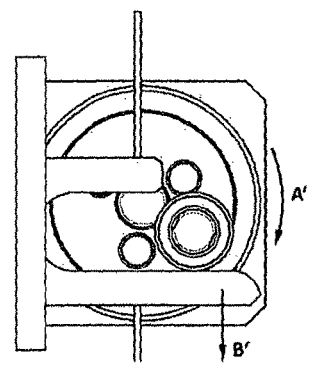
Figure 49E:
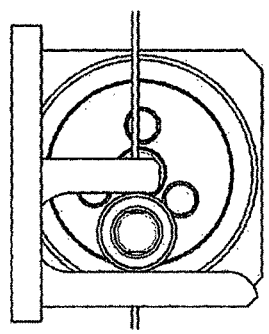
Figure 49F:
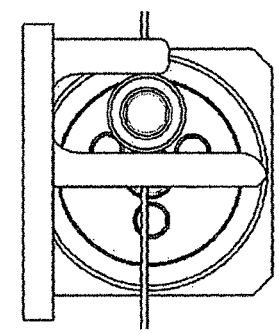

In FIG. 49A, the input drive module and the instrument shaft are connected to one another, wherein the output drive link and the input drive link 32' are not yet coupled to one another. By rotating the output drive link (cf. movement arrow A' in FIGS. 48A, 49C) the guide element 30' rotates through an opening in the, in FIGS. 49A-49F, upper, guide wall of the groove 33' into the groove (cf. movement arrow F in FIG. 49A) and thus couples—initially in a one-sided manner—the output drive link and the input drive link (FIG. 49B). When the output drive link is rotated further (cf. movement arrow A' in FIG. 49C), the guide element 30', which is now inserted in the groove 33', pushes the input drive link 32' into the thrust bearing 34' in its displacement axis B'. In FIGS. 49D-49F it is clear how the rotating of the output drive link displaces the input drive link on both sides along its displacement axis B', and can thus actuate the end effector: by rotating the output drive link and the guide element 30' eccentrically disposed thereon, in the direction of, or opposite, respectively, the movement arrow A' in FIG. 49C, the input drive link 32' can be displaced in its displacement axis B' in both directions (up or down in FIGS. 49A-49F), and thus, an intracorporeal degree of freedom of the instrument is actuated via the pulling means, or the push rod 36, respectively (cf. FIGS. 48A-48B).

In the embodiment in FIGS. 48A-48B, 49A-49F, the (upper, in the figures) guide wall of the groove has an opening for inserting the guide element by rotating its output drive link, which is formed by a shortened leg of an open, or U-shaped pair of legs, which in turn defines the groove.

FIG. 50 shows, in a manner corresponding to that of FIGS. 48A-48B, an interface of a surgical instrument according to a further embodiment of the present invention, in a partial section. As is the case in FIGS. 48A-48B, for a better overview, only some of the components of an input drive module 125 and instrument shaft 120 are depicted, in particular only one drive train for actuating a degree of freedom of the instrument shaft is shown, while further drive trains can be constructed in an analogous manner, and be disposed, for example, parallel to the shown drive train.

Each drive train has an actuator in the form, for example, of an electric motor-gearing unit 131, the output drive shaft of which represents an output drive link of the input drive module, which can rotate without limit.

An input drive link 132 is linked to this output drive link in a manner described below, which is inserted, in a form-locking manner, in a thrust bearing (not shown) in the instrument shaft that can be displaced in a displacement axis B''', and is connected to the end effector by a pulling means or a push rod, which is parallel to the displacement axis B'''.

A linear groove (cut in FIG. 50) is disposed in the input drive link, which is perpendicular to the displacement axis B''' and an axis of a guide element 130, which is disposed eccentrically on the rotatable output drive link and displaceably guided in the groove, when the output drive link and the input drive link are coupled to one another. The rotational axis of the rotatable output drive link is perpendicular to the displacement axis B''' of the displaceably guided input drive link and the groove. The eccentric guide element 130 is supported on a frame 139 of the actuator 131 via a radial bearing 140.

A tolerance element 132.3 is provided in the embodiment in FIG. 50. The tolerance element is displaceably guided on the input drive link 132 parallel to its displacement axis B''', and pre-tensioned in an elastic manner against it by means of a spring element 132.4. In this manner, the tolerance element 132.3 pre-tensions the output drive link and the input drive link in the displacement axis B''' of the input drive link, when the output drive link and the input drive link are coupled to one another.

The tolerance element has a tolerance element groove, which is parallel to the groove in the input drive link 132, and through which the guide element 130.2 passes, when the output drive element and the input drive element are coupled.

In the embodiment in FIG. 50, the guide element has a rotatably mounted roller element in the form of a ball race 130.2, which is mounted in a sliding or rolling manner, for making contact to the groove in the input drive element. A further rotatably mounted roller element in the form of a ball race 130.1, mounted in a sliding or rolling manner, is disposed axially adjacent thereto for making contact with the tolerance element groove. In a variation, instead of this, roller bearings without an outer race can also be provided.

The guide element 130 is mounted in the output drive link such that it is axially displaceable. As a result, it can be axially inserted in, or removed from, respectively, the groove in the input drive element and the tolerance element groove. It is pre-tensioned against the grooves by means of an axial spring (not shown), such that it enters these grooves automatically.

A connecting member 138 for axial displacement of guide elements is connected to the frame 139 in a non-rotatable manner. It has a chamfer in the direction of rotation, on which collar of the guide element slides up. In this manner, by rotating the output drive link in the direction indicated by a movement arrow A''' in FIG. 50, via the connecting member 138, the guide element 130.2 can be axially displaced (toward the left in FIG. 50) and thus taken out of engagement with the grooves. In a variation not shown here, the guide element can be axially displaced in opposing directions by means of the connecting member, in rotational positions that are spaced apart from one another, and thus, is not brought out of engagement, but rather, is also brought into engagement with the grooves. For this, the connecting member can have a further chamfer, corresponding to the chamfer depicted in FIG. 50, which runs in the opposite direction, and is spaced apart therefrom in the direction of rotation, which pushes the collar of the guide element axially into the groove when the output drive link is rotated in the direction opposite A'''. In this case, a pre-tensioning can be reduced or eliminated by an axial spring.

FIGS. 51A, 51B show, in a perspective view (FIG. 51A) and a partial view (FIG. 51B), an interface of a surgical instrument according to another embodiment of the present invention. This corresponds substantially to the embodiment in FIG. 50, such that reference is made to its description, and only the differences shall be addressed below.

In the embodiment in FIGS. 51A-51B, the tolerance element is designed as an integral part of the input drive link 132'', this being in a hollow chamber 333.3, in which an integral leg 333.1 can be inserted, which is supported on both sides (left, right in FIG. 51A).

In the partial section in FIG. 51B, the guide element 330 can be seen, which is guided by a roller bearing 330.2 in the groove 333.2 of the input drive link 132''. In addition, the guide element 330 is supported on the leg 333.1 of the integral tolerance element via a further roller bearing 330.1, which pre-tensions the guide element 330 and thus the output drive link, in which it is mounted, and the input drive link 132'' in a displacement axis of the input drive link (vertical in FIG. 51B).

FIG. 52 shows an interface, in a manner corresponding to that in FIG. 51B, of a surgical instrument according to another embodiment of the present invention, in a partial section. This corresponds, substantially, to the embodiment in FIG. 50, such that reference is made here to its description, and only the differences shall be addressed below.

In the embodiment in FIG. 52, an inner race 230.3 of a roller bearing without an outer race, having roller elements 130.1, 130.2, is disposed on a pin 130' of the guide element. The right-hand roller element 130.2 in FIG. 52 functions thereby as a tolerance element, which pre-tensions the guide element and thus the output drive link against the input drive link 132' in a displacement axis $B^{IV}$ of the input drive link, when the output drive link and the input drive link are coupled to one another.

For this, the left roller elements 130.1, in FIG. 52, of the guide element and the tolerance element 130.2 have chamfers in opposing directions, which are complementary to the opposing chamfers 233.1, 233.2 of the input drive element 132'. The tolerance element 130.2 is guided in an axially displaceable manner on the inner race 230.3 of the guide element, and pre-tensioned against it by means of a spring element 230.4. By means of the axial blocking of the tolerance element 130.2 by the chamfer, as a function of the spring element, it pre-tensions the output drive link and the input drive link 132' in the displacement axis $B^{IV}$.

As explained above, the left ball race 130.1 in FIG. 52, which can be mounted in a sliding manner, or can slide, respectively, radially outside on the input drive link 132' and/or radially inside on the inner race 230.3, and the right tolerance element 130.2 in FIG. 52, which can be mounted in a sliding manner, or can slide, respectively, radially outside on the input drive link 132' and/or radially inside on the inner race 230.3, represent roller bodies as set forth in the present invention, and the roller bodies 130.1, 130.2 and inner race 230.3 collectively thus form a roller bearing without an outer race, as set forth in the present invention. In addition, or alternatively, to a rotatability, or sliding support, respectively, of the roller elements 130.1, 130.2 with respect to the input drive link 132' and/or the inner race 230.3, the inner race 230.3 can be non-rotatably mounted on the pin 130', or can be mounted in a sliding manner, or can slide, thereon.

FIGS. 53A, 53B show an interface of a surgical instrument according to another embodiment of the present invention, in various positions. This corresponds substantially to the embodiments described above, such that reference is made here to their description, and only the differences shall be addressed below.

In the embodiment in FIGS. 53A-53B, the O-shaped closed groove 33'' in the input drive element 32'' is designed such that it is asymmetric to the rotational axis of the output drive link 31" (perpendicular to the image plane in FIG. 53), and the displacement axis B" of the input drive element 32", and extends substantially only as far as this rotational axis.

As a result, the output drive link 31" and the input drive link 32" are clearly coupled to one another. If one imagines, on the contrary, the groove 33" extending (toward the left in FIG. 53) beyond the rotational axis, in particular symmetrical thereto, it is clear that the guide element 30" could then engage, in each case in two rotational positions that are symmetrical to the displacement axis B", in the groove 33". As a result of an asymmetrical design of the groove 33', this can be prevented, because, as a result, the guide element 30" can engage in the groove 33" in exactly only one rotational position.

The series of figures, FIGS. 53A-53B again clearly illustrates the functional concept of the interface according to one embodiment of the invention. If the output drive element 31" rotates in the direction indicated in FIGS. 53A-53B by the movement arrow A", the input drive link 32" coupled thereto is displaced in its thrust bearing (hatched in FIGS. 53A-53B) in its displacement axis B". In order to limit this displacement, in particular when the output drive link is decoupled, two end stops 37.1, 37.2 are provided, which run on the front surfaces 32.1" or 32.2", respectively, of the input drive links.

The (full) stroke H of the input drive link is obtained, when the output drive link is decoupled, by means of the spacing of the end stops 37.1, 37.2, based on the spacings B of the front surfaces 32.1" or 32.2" to a mid-line of the groove 33". As a result, in one embodiment of the present invention, for which the depiction in FIGS. 53A-53B show only a possible embodiment, in general, a spacing B of a front surface of the input drive link from a mid-line of the groove in the input drive link is at least equal to the full stroke plus half of the groove width, having the reference symbols in FIGS. 53A-53B:

$$B \geq H + D/2$$

where
- B: spacing of a front surface of the input drive link to a mid-line of the groove;
- H: entire stroke of the input drive link; and
- D: groove width.

FIG. 54 shows an interface of a surgical instrument according to another embodiment of the present invention. This corresponds substantially to the embodiments explained above, such that reference is made here to their descriptions, and only the differences shall be addressed below.

In the embodiment in FIG. 54, a sterile barrier 35 is disposed between the guide element 30 of the output drive link 31 of the input drive module 25, which engages in the groove 33 of the input drive link 32 guided in the displacement axis B on the thrust bearing 34 of the instrument shaft 20, in order to convert a rotational movement A of the guide element 30 into a translational displacement of the input drive link 32. This can also be provided in the embodiments in FIGS. 47-53 explained above, without being shown therein.

FIGS. 55A-55E show an interface of a surgical instrument according to a further embodiment of the present invention, in a view from above, in the direction of a displacement axis (FIGS. 55A-55C), or in a perspective view (FIGS. 55D-55E), wherein the output drive link and the input drive link are not coupled to one another (FIGS. 55A-55B) or are coupled to one another (FIG. 55C). This corresponds substantially to the embodiments explained above, in particular in accordance with FIG. 48, such that reference is made here to the descriptions of the preceding embodiments, and only the differences shall be addressed below.

In the embodiment in FIGS. 55A-55E, the input drive link 32' is guided in a thrust bearing 34' with a great deal of play, in particular, in a loose manner, such that it can be displaced on the instrument shaft. In addition, it is displaceably guided in a thrust bearing 340 having less play, in particular at least substantially without play, on the actuator 31' of the input drive module, when this input drive module is connected to the instrument shaft (cf. FIG. 55C). In the connected state, the less precise guidance on the instrument shaft is thus non-functional. As a result, the more complex, precise guidance is shifted to the input drive module, and thus the instrument shaft can be, or is, designed in a simpler and/or less expensive manner, in particular such that it can more readily be sterilized and/or is a disposable article. As soon as the instrument shaft and the input drive module are connected, the input drive module assumes the—more precise—guidance of the input drive link.

LIST OF REFERENCE SYMBOLS

In the FIGS. 1 to 33:
- 1 drive unit
- 2 instrument shaft
- 3 sterile barrier
- 3.1 compensation element
- 3.2 corrugated membrane (pre-tensioned cuff)
- 3.3 corrugated bellows (pre-tensioned cuff)
- 3.4 elastomer sleeve (cuff)
- 3.5 translationally displaceable seal
- 3.6 sterile extension
- 3.7 reinforcement
- 4 adapter (attachment element)
- 10A, 10B output drive element (output drive assembly)
- 10C coupling means
- 10D guide rail
- 11 output drive element base
- 20A, 20B input drive element (input drive assembly)
- 20C coupling means
- 20D rotational thrust bearing
- 20E gear toothing
- 21 input drive element base
- 30 roller
- 40 coupling rod
- 50 spring
- 60 pull cable
- 100 pin
- 100.1 extension sleeve/tension lever (elastic/separate element)
- 100.2 threaded spindle/actuating stud (clamping means)
- 100.3 electric motor
- 100.4 spindle nut
- 100.5 thrust bearing
- 100.6 locking balls
- 100.7 intermediate element (assembly)
- 100.8 cage sleeve
- 200 coupling socket with cut-out (input drive element)
- 200.1 compression spring
- 1000 tilt lever (output drive/input drive element)
- 2000 coupling part (input drive/output drive element)
- 2000.1 thrust bearing In the FIGS. 34 to 36:
- 2.1, 2.2 blade (end effector)
- 3 control means 4 sterile barrier
5 spring
10 input drive module
11, 12 tappet ((input drive module-side) drive train (assembly))
13 electric motor (input drive)
20 instrument shaft
21, 22 tappet ((instrument shaft-side) drive train (assembly))
31-34 strain metering strip (metering means, metering assembly)
$F_{E1}$, $F_{E2}$ clamping force
$F_{S1}$, $F_{S2}$ instrument shaft tappet force
$F_1$, $F_2$ input drive module tappet force
$q_1$ (rotational) degree of freedom
S1 method step
$U_A$ bridge output voltage
$U_E$ supply voltage
In the FIGS. 37 to 46B:
30 drive unit
31 instrument shaft
32 (flexible) sterile barrier
34, 35 output drive tappet
37, 38 input drive tappet
40 robot
41 (sterile) casing
42 interface
44; 44a, 44b electric motor
45a-45d pair of tappets
45.1 output drive link assembly
45.2 input drive link assembly
46; 46a, 46b spring element (compression spring)
47; 47a, 47b input drive module
47.1 housing for the input drive module
49 housing
53 instrument shaft housing
54 tube
55 pivot bearing
56a, 56b interface
57.1, 57.2, 57a-57d cable pull drum
58 gearing wheel
59 rocker
60 (mechanical) stop
61, 167 latch
80 mounting element
100, 103 electromagnet
101, 104 permanent magnet
102 spacing element
105 spacing element
106 counter-stop
140 insertion opening
142, 143, 164 recess
150 cut-out
151, 153 projection
152, 160, 166 guide groove
161, 165 guide rib
170 lid
180a, 180b section/converging surface
181a, 181b moveable roller
In the FIGS. 47 to 55D:
20; 20'; 120 instrument shaft
21 end effector
22 tube
23 instrument housing
24 interface
25; 25'; 125 input drive module
30; 30'; 30"; 130; 330 guide element
31 output drive link
31'; 31"; 131 electric motor gearing unit (actuator)
32; 32'; 32"; 132; 132'; 132" input drive link
32.1"; 32.2" front surface
33; 33'; 33" groove
34; 34' thrust bearing
35 sterile barrier
36; 136 pull cable/push rod
37.1, 37.2 end stop
130.1 bearing race (roller body)
130.2 bearing race (tolerance element)
130' pin
132.3 tolerance element
132.4 spring element
138 connecting member
139 frame
140 radial bearing
230.3 inner race
230.4 spring element
233.1, 233.2 chamfers
330.1, 330.2 roller bearing
333.1 leg (integral tolerance element)
333.2 groove
333.3 hollow chamber
340 thrust bearing
A; A'; A"; A'" rotational movement
B; B'; B"; B'''; $B^{IV}$ displacement axis

What is claimed is:

1. A surgical instrument assembly, comprising:
a modular motor drive unit, which has an output drive assembly with at least one output drive element, and
an instrument shaft, which is releasably connected to the drive unit and has an input drive assembly with at least one input drive element,
wherein the output drive assembly and the input drive assembly are couplable to one another by a mechanical interface,
the mechanical interface comprising a pin and a cut-out,
wherein a gap is formed between the pin and the cut-out, the gap being wave-shaped in a radial direction, and having an intermediate element assembly disposed in the gap, the intermediate element assembly being radially displaceable and axially secured such that:
when the pin is displaced axially, a wave-shaped outer wall of the pin that faces the cut-out is displaced in a corresponding manner and moves the intermediate element assembly in the radial direction in a form-locking manner, which thereby causes a corresponding axial displacement of the cut-out in a form-locking manner, or
when the cut-out is displaced axially, a wave-shaped inner wall of the cut-out that faces the pin is displaced in a corresponding manner and moves the intermediate element assembly in the radial direction in a form-locking manner, which thereby cause a corresponding axial displacement of the pin in a form-locking manner.

2. The instrument assembly according to claim 1, wherein at least one of the output drive element or input drive element is guided in a translationally or rotationally adjustable manner.

3. The instrument assembly according to claim 1, wherein at least one of the output drive element or input drive element is coupled with a coupling means in such a manner that a translational or rotational movement by one of the elements and the coupling means is converted into the other of a translational or rotational movement by the other one of the elements and the coupling means.

4. The instrument assembly according to claim 3, wherein the coupling means includes at least one of:
a rotational thrust bearing or;
a gear toothing.

5. The instrument assembly according to claim 1, wherein the instrument shaft has a flange, and wherein the mechanical interface is disposed on a surface facing an end effector, a surface facing away from the end effector, or a lateral surface of the flange.

6. The instrument assembly according to claim 1, wherein at least one of the output drive assembly or the input drive assembly has at least one pair of output drive elements or input drive elements, running in opposing directions.

7. The instrument assembly according to claim 1, having a compensation means for compensating for tolerances.

8. The instrument assembly according to claim 1, wherein at least one of the at least one output drive element or the at least one input drive element is pre-tensioned counter to its adjustment direction.

9. The instrument assembly according to claim 1, wherein at least one of two front surfaces of an output drive element and an input drive element that are coupleable thereto, facing each other, is configured such that the at least one surface is at least one of:
flat;
spherical; or
has a projection for engaging in a cut-out in the other front surface.

10. The instrument assembly according to claim 1, further comprising a clamping means for radially expanding the pin of the mechanical interface, inserted in the cut-out.

11. A surgical instrument, comprising:
a modular motor drive unit, which has an output drive assembly with at least one output drive element,
an instrument shaft releasably connected to the drive unit and having an input drive assembly with at least one input drive element,
wherein the output drive assembly and the input drive assembly are couplable to one another by a mechanical interface,
the mechanical interface comprising a pin and a cut-out,
wherein a gap is formed between the pin and the cut-out, the gap being wave-shaped in a radial direction, and having an intermediate element assembly disposed in the gap, the intermediate element assembly being radially displaceable and axially secured such that:
when the pin is displaced axially, a wave-shaped outer wall of the pin that faces the cut-out is displaced in a corresponding manner and moves the intermediate element assembly in the radial direction in a form-locking manner, which thereby causes a corresponding axial displacement of the cut-out in a form-locking manner, or
when the cut-out is displaced axially, a wave-shaped inner wall of the cut-out that faces the pin is displaced in a corresponding manner and moves the intermediate element assembly in the radial direction in a form-locking manner, which thereby cause a corresponding axial displacement of the pin in a form-locking manner, and
a sterile barrier, which is provided for encasing the drive unit, the sterile barrier disposed between the drive unit and the instrument shaft and comprising at least one of:
a cuff in the region of the mechanical interface in an adjustment direction of the output drive assembly and the input drive assembly,
a seal that is translationally displaceable,
a compensation means for compensating for tolerances or
an element extension releasably connectable to either an output drive element or an input drive element, which passes through the sterile barrier in a destructive manner.

12. A surgical instrument assembly, comprising:
a modular motor drive unit, having an output drive assembly with at least one output drive element,
an instrument shaft releasably connected to the drive unit and having an input drive assembly with at least one input drive element,
wherein the output drive assembly and the input drive assembly are couplable to one another by a mechanical interface,
the mechanical interface comprising a pin and a cut-out,
wherein a gap is formed between the pin and the cut-out, the gap being wave-shaped in a radial direction, and having an intermediate element assembly disposed in the gap, the intermediate element assembly being radially displaceable and axially secured such that:
when the pin is displaced axially, a wave-shaped outer wall of the pin that faces the cut-out is displaced in a corresponding manner and moves the intermediate element assembly in the radial direction in a form-locking manner, which thereby causes a corresponding axial displacement of the cut-out in a form-locking manner, or
when the cut-out is displaced axially, a wave-shaped inner wall of the cut-out that faces the pin is displaced in a corresponding manner and moves the intermediate element assembly in the radial direction in a form-locking manner, which thereby cause a corresponding axial displacement of the pin in a form-locking manner,
a sterile barrier, which is provided for encasing the drive unit, and
an attachment element for a releasable connection with the drive unit, which is provided such that it is positionable on one of the surfaces of the sterile barrier facing away from the drive unit.

13. A manipulator surgical system having at least one manipulator and at least one manipulator-guided instrument assembly according to claim 1, the drive unit and instrument shaft of which are connectable to one another.

14. A method for equipping a manipulator of a manipulator surgical system according to claim 13, wherein a modular motor drive unit and an instrument shaft of the instrument assembly are releasably connected to one another, and the output drive assembly and the input drive assembly are coupled to one another by means of the mechanical interface.

15. The surgical instrument of claim 1, wherein the pin is expandable in the cut-out in at least one of:
an elastic manner or;
by at least one separate body.

16. The surgical instrument of claim 1, wherein the mechanical interface comprises a tilt lever.

17. The surgical instrument of claim 11, wherein the cuff is pre-tensioned.

* * * * *